(12) United States Patent
Dong et al.

(10) Patent No.: US 11,066,455 B2
(45) Date of Patent: Jul. 20, 2021

(54) TMEM100 PEPTIDES AND VARIANTS THEREOF AND THEIR USE IN TREATING OR PREVENTING DISEASES OR CONDITIONS

(71) Applicant: The Johns Hopkins University, Baltimore, MD (US)

(72) Inventors: Xinzhong Dong, Clarksville, MD (US); Hao-Jui Weng, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/119,583

(22) PCT Filed: Feb. 20, 2015

(86) PCT No.: PCT/US2015/016793
§ 371 (c)(1),
(2) Date: Aug. 17, 2016

(87) PCT Pub. No.: WO2015/127186
PCT Pub. Date: Aug. 27, 2015

(65) Prior Publication Data
US 2017/0305990 A1    Oct. 26, 2017

Related U.S. Application Data

(60) Provisional application No. 61/943,615, filed on Feb. 24, 2014.

(51) Int. Cl.
| | |
|---|---|
| *C07K 14/705* | (2006.01) |
| *A61K 38/17* | (2006.01) |
| *A01K 67/027* | (2006.01) |
| *A61K 48/00* | (2006.01) |
| *A61K 38/00* | (2006.01) |

(52) U.S. Cl.
CPC ........ *C07K 14/705* (2013.01); *A01K 67/0276* (2013.01); *A61K 38/1709* (2013.01); *A01K 2217/075* (2013.01); *A01K 2217/203* (2013.01); *A01K 2227/105* (2013.01); *A01K 2267/0356* (2013.01); *A61K 38/00* (2013.01); *A61K 48/00* (2013.01)

(58) Field of Classification Search
None
See application file for complete search history.

(56) References Cited

U.S. PATENT DOCUMENTS 4,775,622 A * 10/1988 Hitzeman ............ C07K 14/555
435/254.2
2010/0249154 A1    9/2010 Ng et al.

FOREIGN PATENT DOCUMENTS

WO    WO-2012-085662 A1    6/2012
WO    WO-2013-134860 A1    9/2013

OTHER PUBLICATIONS

Schwartz, et al. "TRPV1 and TRPA1 antagonists prevent the transition of acute to chronic inflammation and pain in chronic pancreatitis" The Journal of Neuroscience, 2013, vol. 33, No. 13, pp. 5603-5611.
Weng, et al. "TMEM100 is a regulator of TRPA1-TRPV1 Complex and Contributes to Persistent Pain" Neuron, Feb. 18, 2015, vol. 85, No. 4, pp. 833-846.
NCBI, GenBank accession No. BAA91931.1, Jan. 9, 2008, whole document.
NCBI, GenBank accession No. BC010128.2, Jul. 15, 2006, whole document.
NCBI, Reference Sequence XP_005075869.1, Jul. 17, 2013, whole document.
NCBI, GenBank accession No. AK003574.2, Oct. 6, 2010, whole document.

* cited by examiner

*Primary Examiner* — John D Ulm
(74) *Attorney, Agent, or Firm* — Mintz Levin Cohn Ferris Glovsky and Popeo, P.C.; Peter F. Corless

(57) ABSTRACT

The present invention features compositions of Tmem100 peptides and variants thereof, and their use in treating or preventing diseases or conditions.

18 Claims, 18 Drawing Sheets
Specification includes a Sequence Listing.

SEQUENCE LISTING

```
<160> NUMBER OF SEQ ID NOS: 20

<210> SEQ ID NO 1
<211> LENGTH: 134
<212> TYPE: PRT
<213> ORGANISM: Homo sapiens
```

-continued

<400> SEQUENCE: 1

Met Thr Glu Glu Pro Ile Lys Glu Ile Leu Gly Ala Pro Lys Ala His
1               5                   10                  15

Met Ala Ala Thr Met Glu Lys Ser Pro Lys Ser Glu Val Val Ile Thr
            20                  25                  30

Thr Val Pro Leu Val Ser Glu Ile Gln Leu Met Ala Ala Thr Gly Gly
        35                  40                  45

Thr Glu Leu Ser Cys Tyr Arg Cys Ile Ile Pro Phe Ala Val Val Val
    50                  55                  60

Phe Ile Ala Gly Ile Val Val Thr Ala Val Ala Tyr Ser Phe Asn Ser
65                  70                  75                  80

His Gly Ser Ile Ile Ser Ile Phe Gly Leu Val Val Leu Ser Ser Gly
                85                  90                  95

Leu Phe Leu Leu Ala Ser Ser Ala Leu Cys Trp Lys Val Arg Gln Arg
            100                 105                 110

Ser Lys Lys Ala Lys Arg Arg Glu Ser Gln Thr Ala Leu Val Ala Asn
        115                 120                 125

Gln Arg Ser Leu Phe Ala
    130

<210> SEQ ID NO 2
<211> LENGTH: 134
<212> TYPE: PRT
<213> ORGANISM: Mus musculus

<400> SEQUENCE: 2

Met Thr Glu Glu Ser Thr Lys Glu Asn Leu Gly Ala Pro Lys Ser Pro
1               5                   10                  15

Thr Pro Val Thr Met Glu Lys Asn Pro Lys Arg Glu Val Val Val Thr
            20                  25                  30

Thr Gly Pro Leu Val Ser Glu Val Gln Leu Met Ala Ala Thr Gly Gly
        35                  40                  45

Ala Glu Leu Ser Cys Tyr Arg Cys Ile Ile Pro Phe Ala Val Val Val
    50                  55                  60

Phe Ile Thr Gly Ile Val Val Thr Ala Val Ala Tyr Ser Phe Asn Ser
65                  70                  75                  80

His Gly Ser Ile Ile Ser Ile Phe Gly Leu Val Leu Leu Ser Ser Gly
                85                  90                  95

Leu Phe Leu Leu Ala Ser Ser Ala Leu Cys Trp Lys Val Arg Gln Arg
            100                 105                 110

Asn Lys Lys Val Lys Arg Arg Glu Ser Gln Thr Ala Leu Val Val Asn
        115                 120                 125

Gln Arg Cys Leu Phe Ala
    130

<210> SEQ ID NO 3
<211> LENGTH: 2269
<212> TYPE: DNA
<213> ORGANISM: Homo sapiens

<400> SEQUENCE: 3
cagttgcttc tacaaaaccc gtgaaagttc tctgtccaaa agccttgttg gtcccgcggt     60
acatgcttcc tgttcccaga gagattcacc cttgggcttt cctatcagtc ttccctaaag    120
ttggctgctc ctgtgtcctg tcacataaaa ctgtgaaccg aggtctccga cttacgtcat    180
gtcagtcaca gcagggtgag gctccacaag tgtgagttct ggcccctgct gctttccttt    240

```
caaatgcagt ttacagttta ttatggtatt ggacacccca tgctccttac tgcattggct      300
ttgggtaaga aggagtgaaa attagtgtgc gaacctgaaa acctagaatt tctgattggg      360
actgaagaaa acctttgtgc tgcagtcagt ccccgagcca gacgcctgtg actctcttca      420
catgaaaata gatgactatc acagtaaaa gcaaaattaa aaagtgactt gtgaaaaata      480
tcctccatgc tcctcttacc aagcctgcaa cttaaaacct atggtttaaa ctgtgctttc      540
aattatctgg aggaggccag cactgatgag cccatcctga gccagtcatt ttaaggccag      600
tgctacctaa ctgagacaag gctaatctgg tcgccttgct gttagaggct ctttcccaga      660
agttggacga gagggctcag gcgttgctgt ttcttgtctt ccaagtcaag tggttactct      720
ggtaatggat tgcctctctc cgagctttca ccctggtgag actgtccaga tctagtctgt      780
aaacccagct tagaagcact gttgtaaaaa tgactgaaga gcccatcaag gagatcctgg      840
gagccccaaa ggctcacatg gcagcgacga tggagaagag ccccaagagt gaagttgtga      900
tcaccacagt ccctctggtc agtgagattc agttgatggc tgctacaggg ggtaccgagc      960
tctcctgcta ccgctgcatc atcccctttg ctgtggttgt cttcatcgcc ggcatcgtgg     1020
tcaccgcggt ggcttacagc ttcaattccc atgggtctat tatctccatc tttggcctgg     1080
ttgttctgtc atctggactt tttttactag cctccagtgc cttgtgctgg aaagtgagac     1140
aaaggagcaa gaaagccaag agacgggaga gtcaaacagc tctcgtggca aatcagagaa     1200
gcttgtttgc ttgagactga atacgaccaa atgggccatt gggcctggaa acgtgctct      1260 gactttgtca cccaattcac ccagaaccat ggtgggagag aacagacttg gcgttggagc     1320
agactggaag aatgggggtg ggagggtgga ggggcttctc ctttgtgagg aatgactcat     1380
gtcttcttta cgacaaaact taaccctaag ggctacttct gagactgaaa atcagctttt     1440
ctatttacat gaaacacttt gggggtcatg ggagtgcaca gcattagaca gtatttggtt     1500
caccctgtaa agtagccaag aaaagatgag aaaaatcaag ataggcctgg cacactagac     1560
atttgcctcc aaaagaaata acctacagtc ttaagatgta tcataaaaat gttctgccaa     1620
ggatctaaat taccttgggt ttcgcatatg tctatgaaat tctgtgataa ttttttttcaa     1680 tacattgatt cactggcgtc tgttttcatt ttatactttt aataactcat cactggtggt     1740
actttatctt gaaagtaat attttttata ttttaacatt ggacagtgtt agccagttgt      1800
aatgatgtat cagaagtaaa gaaaaaccca ttaaagttat agctaataga tgctgttggg     1860
ggttaaatta atagtaaaat aatccaatat agcacttttg atgattttta tataaaagtc     1920
aactgtacat ttcattcaga ataataaata cttattgctg ctaaaacttc ttaaatggtt     1980
gtttctgcta tagttatttc tattgcagtt ccaaattgcc atcttcccctt gtctcatttg     2040 caagttctca attgtatttc tctcaaatgg acaggttcct tctttactgg aggattttttg    2100 tttttatcat attggttttt cattacttct gaatagtctt aattacgttt actaaattct     2160
aaaggatttc tgtgctatta taattaggaa atcaacgtct ttggtcagga actttataat     2220
gtgctattaa atgtatatta cattttttgtg gaaaaaaaaa aaaaaaaa                 2269
```

<210> SEQ ID NO 4
<211> LENGTH: 1764
<212> TYPE: DNA
<213> ORGANISM: Mus musculus

<400> SEQUENCE: 4

```
tctgcagctt cacactacaa aagagtgata tcgaagacta ggttagagaa aaccataaaa       60
```

-continued

```
aagaatgctt gcataaggat tttaaacggg ggaaagaaaa caggagagat ttttagtgac    120
tttttaaata attgggttat gatggattca ctcctgtaat tacagtggat ggtgtgggca    180
cggaaaaaaa aatagaaaag aaaaggaaaa cgtagagtaa aatacaacag cgagtaagga    240
atttcctttc accaaattgt ctccggtccc ttaatggtct gtaaatcttg ctgagtactt    300
tgtgtacggt ccctagcatg gtgatttgca tcccactgtc ggcctcgctg ttggccgccg    360
cttgctgctg tctcagtcca cttctggctg agaaagaggc aatccctggt ctgtcctttt    420
accaatgccc agtgggtgac aggctctttc ccagaagttg aacggagcta cgctggcaga    480
tccctctctc ccaagtcaag tggcctctct ggtaatggac tgcctttctg tgagcttgca    540
tcctgaccag gctttccaaa tctagcctgt gaagcgagat aagaaaaatc ccacagaaga    600
aaaaaaaatg accgaagaat ccacaaaaga gaacctggga gctccaaaat ctcccacacc    660
tgtgacaatg gagaaaaacc ccaagaggga agttgtggtc accacgggac ccttggtcag    720
cgaggttcag ctgatggccg ccaccggggg tgccgaactc tcctgctacc gctgcatcat    780
cccctttgcc gtggtggtct tcatcactgg gattgtggtc accgctgtgg cttacagctt    840
caattcccat ggttccatca tctccatctt cggcctggtc cttctgtcct ccggactgtt    900
tttactagcc tccagtgcct tgtgctggaa ggtgagacaa aggaacaaga aagtcaagag    960
acgcgagagt cagaccgctc ttgtggtaaa tcagaggtgc ttgtttgctt aagactgagt   1020
aagagcaaac gcgaacgctc acccgcccac actgctctaa ctcagtgaac tcattcatag   1080
gaaaccagcc cggtaccgga tgagctcaac tttcgaatga actaccaaaa tgaaaaatag   1140
ggcatagaga ggactgaaaa tgaggggtca agacggttcc cccttggtag ggaataactc   1200
atctttaacg acaaacttaa ccctaagggc tatttctaac acagacagag gaatcagctt   1260
gcttttcctg ttaaacgttt agggagtgtg ggagatgcac agcattaaat aacagttggt   1320
tccatttaga aagtacccaa gggaagaatg gacaaataat gagagccctg caagtggtg    1380 ttataaaaac gttccaccaa aagcctacat tggcttggca ttcccacgta cctaagaagt   1440
tctgttatat atatacatat atatttttc caataagttg attctttgcc cccccttttt    1500
taaaagaatt ttcactttca gtaacatcac tagaggtact ttattttgaa gaatagacta   1560
atatttttta tattttaaca atggacaatt gtagatggtt gtaatgatat gtcagaagaa   1620
aacagaaatg taggtaacac agatgacaca gggacagtta aattaatatt gaataatcc    1680 aatctagcac ctttgatggc ttttatacaa aagttcagtg tgcatttcac tcaaaataat   1740
aaatgctcat ggctgctgaa actt                                          1764
```

<210> SEQ ID NO 5
<211> LENGTH: 134
<212> TYPE: PRT
<213> ORGANISM: Homo sapiens

<400> SEQUENCE: 5

```
Met Thr Glu Glu Pro Ile Lys Glu Ile Leu Gly Ala Pro Lys Ala His
1               5                  10                  15

Met Ala Ala Thr Met Glu Lys Ser Pro Lys Ser Glu Val Val Ile Thr
            20                  25                  30

Thr Val Pro Leu Val Ser Glu Ile Gln Leu Met Ala Ala Thr Gly Gly
        35                  40                  45

Thr Glu Leu Ser Cys Tyr Arg Cys Ile Ile Pro Phe Ala Val Val Val
    50                  55                  60

Phe Ile Ala Gly Ile Val Val Thr Ala Val Ala Tyr Ser Phe Asn Ser
```

```
                65                  70                  75                  80
His Gly Ser Ile Ile Ser Ile Phe Gly Leu Val Val Leu Ser Ser Gly
                    85                  90                  95

Leu Phe Leu Leu Ala Ser Ser Ala Leu Cys Trp Lys Val Arg Gln Arg
                100                 105                 110

Ser Lys Lys Ala Gln Gln Glu Ser Gln Thr Ala Leu Val Ala Asn
            115                 120                 125

Gln Arg Ser Leu Phe Ala
        130

<210> SEQ ID NO 6
<211> LENGTH: 134
<212> TYPE: PRT
<213> ORGANISM: Mus musculus

<400> SEQUENCE: 6

Met Thr Glu Glu Ser Thr Lys Glu Asn Leu Gly Ala Pro Lys Ser Pro
1               5                   10                  15

Thr Pro Val Thr Met Glu Lys Asn Pro Lys Arg Glu Val Val Val Thr
            20                  25                  30

Thr Gly Pro Leu Val Ser Glu Val Gln Leu Met Ala Ala Thr Gly Gly
        35                  40                  45

Ala Glu Leu Ser Cys Tyr Arg Cys Ile Ile Pro Phe Ala Val Val Val
    50                  55                  60

Phe Ile Thr Gly Ile Val Val Thr Ala Val Ala Tyr Ser Phe Asn Ser
65                  70                  75                  80

His Gly Ser Ile Ile Ser Ile Phe Gly Leu Val Leu Ser Ser Gly
                    85                  90                  95

Leu Phe Leu Leu Ala Ser Ser Ala Leu Cys Trp Lys Val Arg Gln Arg
                100                 105                 110

Asn Lys Lys Val Gln Gln Glu Ser Gln Thr Ala Leu Val Val Asn
            115                 120                 125

Gln Arg Cys Leu Phe Ala
        130

<210> SEQ ID NO 7
<211> LENGTH: 28
<212> TYPE: PRT
<213> ORGANISM: Homo sapiens

<400> SEQUENCE: 7

Trp Lys Val Arg Gln Arg Ser Lys Ala Gln Gln Glu Ser Gln
1               5                   10                  15

Thr Ala Leu Val Ala Asn Gln Arg Ser Leu Phe Ala
            20                  25

<210> SEQ ID NO 8
<211> LENGTH: 28
<212> TYPE: PRT
<213> ORGANISM: Mus musculus

<400> SEQUENCE: 8

Trp Lys Val Arg Gln Arg Asn Lys Lys Val Gln Gln Glu Ser Gln
1               5                   10                  15

Thr Ala Leu Val Val Asn Gln Arg Cys Leu Phe Ala
            20                  25

<210> SEQ ID NO 9
```

```
<211> LENGTH: 405
<212> TYPE: DNA
<213> ORGANISM: Homo sapiens

<400> SEQUENCE: 9
atgactgaag agcccatcaa ggagatcctg ggagccccaa aggctcacat ggcagcgacg      60
atggagaaga gccccaagag tgaagttgtg atcaccacag tccctctggt cagtgagatt     120
cagttgatgg ctgctacagg gggtaccgag ctctcctgct accgctgcat catcccctttt    180 gctgtggttg tcttcatcgc cggcatcgtg gtcaccgcgg tggcttacag cttcaattcc     240
catgggtcta ttatctccat cttggcctg gttgttctgt catctggact ttttttacta      300
gcctccagtg ccttgtgctg gaaagtgaga caaaggagca gaaagcccca gcaacaggag     360
agtcaaacag ctctcgtggc aaatcagaga agcttgtttg cttga                     405

<210> SEQ ID NO 10
<211> LENGTH: 405
<212> TYPE: DNA
<213> ORGANISM: Mus musculus

<400> SEQUENCE: 10
atgaccgaag aatccacaaa agagaacctg ggagctccaa atctcccac acctgtgaca      60 atggagaaaa accccaagag ggaagttgtg gtcaccacgg gacccttggt cagcgaggtt    120
cagctgatgg ccgccaccgg gggtgccgaa ctctcctgct accgctgcat catcccctttt   180 gccgtggtgg tcttcatcac tgggattgtg gtcaccgctg tggcttacag cttcaattcc    240
catggttcca tcatctccat cttcggcctg gtccttctgt cctccggact gttttttacta   300 gcctccagtg ccttgtgctg gaaggtgaga caaaggaaca gaaagtcca gcaacaggag    360 agtcagaccg ctcttgtggt aaatcagagg tgcttgtttg cttaa                    405

<210> SEQ ID NO 11
<211> LENGTH: 87
<212> TYPE: DNA
<213> ORGANISM: Homo sapiens

<400> SEQUENCE: 11
tggaaagtga gacaaaggag caagaaagcc cagcaacagg agagtcaaac agctctcgtg     60
gcaaatcaga gaagcttgtt tgcttga                                          87

<210> SEQ ID NO 12
<211> LENGTH: 87
<212> TYPE: DNA
<213> ORGANISM: Mus musculus

<400> SEQUENCE: 12
tggaaggtga gacaaaggaa caagaaagtc cagcaacagg agagtcagac cgctcttgtg     60
gtaaatcaga ggtgcttgtt tgcttaa                                          87

<210> SEQ ID NO 13
<211> LENGTH: 28
<212> TYPE: PRT
<213> ORGANISM: Mus musculus

<400> SEQUENCE: 13

Trp Lys Val Arg Gln Arg Asn Lys Lys Val Lys Arg Arg Glu Ser Gln
1               5                   10                  15

Thr Ala Leu Val Val Asn Gln Arg Cys Leu Phe Ala
            20                  25
```

<210> SEQ ID NO 14
<211> LENGTH: 28
<212> TYPE: PRT
<213> ORGANISM: Mus musculus

<400> SEQUENCE: 14

Trp Lys Val Arg Gln Arg Asn Lys Lys Val Lys Arg Glu Ser Gln
1               5                   10                  15

Thr Ala Leu Val Val Asn Gln Arg Cys Leu Phe Ala
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Arg Val Leu Glu Gln Val Leu Gln Asn Trp Ser Arg Arg Ala Asn
1               5                   10                  15

Val Lys Gln Ala Gln Lys Phe Gln Val Lys Cys Thr
            20                  25

<210> SEQ ID NO 16
<211> LENGTH: 15
<212> TYPE: PRT
<213> ORGANISM: Mus musculus

<400> SEQUENCE: 16

Glu Ser Gln Thr Ala Leu Val Val Asn Gln Arg Cys Leu Phe Ala
1               5                   10                  15

<210> SEQ ID NO 17
<211> LENGTH: 18
<212> TYPE: PRT
<213> ORGANISM: Mus musculus

<400> SEQUENCE: 17

Trp Lys Val Arg Gln Arg Asn Lys Lys Val Gln Gln Gln Glu Ser Gln
1               5                   10                  15

Thr Ala

<210> SEQ ID NO 18
<211> LENGTH: 19
<212> TYPE: PRT
<213> ORGANISM: Mus musculus

<400> SEQUENCE: 18

Gln Arg Asn Lys Lys Val Gln Gln Gln Glu Ser Gln Thr Ala Leu Val
1               5                   10                  15

Val Asn Gln

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gln Arg Ala Leu Glu Gln Val Leu Gln Asn Trp Ser Arg Arg Ala Asn
1               5                   10                  15

Val Lys Gln Ala Gln Lys Phe Gln Val Lys Ser Thr
                20                  25

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 20

His His His His His His
1               5
```

TMEM100 PEPTIDES AND VARIANTS THEREOF AND THEIR USE IN TREATING OR PREVENTING DISEASES OR CONDITIONS

CROSS REFERENCE TO RELATED APPLICATIONS

This application is a national stage application, filed under 35 U.S.C. § 371, of International Application No. PCT/US2015/016793, filed on Feb. 20, 2015, which claims priority to U.S. Ser. No. 61/943,615, filed on Feb. 24, 2014. The entire contents of each of which are incorporated herein by reference in their entireties.

STATEMENT OF RIGHTS TO INVENTIONS MADE UNDER FEDERALLY SPONSORED RESEARCH

This invention was made with government support under grant number GM087369 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Jul. 31, 2018, is named 48317-441N01US_SL.txt and is 15,152 bytes in size.

BACKGROUND OF THE INVENTION

Hypersensitivity to thermal, mechanical, and chemical stimuli is one of the main symptoms of many debilitating diseases, including a variety of painful conditions (e.g., arthritis, tissue damage, post-operative state, etc.), pulmonary conditions (e.g., asthma and COPD), and lower urinary tract disorders. Neuronal plasticity within peripheral sensory ganglia plays a key role in hypersensitivity. It is recognized that a wide range of external stimuli causing hypersensitivity are detected by sensory ganglia neurons. This diverse range of stimuli reflects the heterogeneous nature of a similarly diverse set of molecules needed to distinguish them, and Transient Receptor Potential (TRP) channels play an important role in such sensory modalities. Given the central importance of ion channels in modulating membrane potential and ion flux in cells, identification of agents that can promote or inhibit particular ion channels are of great interest as research tools and as possible therapeutic agents.

One such channel is the Transient Receptor Potential A1 (TRPA1) channel. TRPA1 is a calcium permeable channel, specifically a non-selective calcium permeable cation channel. In addition to calcium ions, TRPA1 channels are permeable to other cations, for example sodium. Thus, TRPA1 channels modulate membrane potential by modulating the flux of cations such as calcium and sodium ions. TRPA1 is found in sensory neurons and functions as a signal transduction receptor linking inflammation to pain. Activation of TRPA1 can cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP (which induce vasodilation and help recruit immune cells). A variety of endogenous reactive compounds produced during inflammation activate TRPA1 (including 4-hydroxynonenal released during liposome peroxidation; cyclopentane prostaglandins synthesized by COX enzymes; hydrogen peroxide produced by oxidative stress). TRPA1 can also be activated by a variety of stimuli, including natural products, environmental irritants, amphipathic molecules and pharmacological agents. Activation of TRPA1 also sensitizes TRPA1 to cold. Furthermore, a gain-of-function mutation in TRPA1 causes familial episodic pain syndrome; patients suffering from this condition have episodic pain that are triggered by cold. Thus, TRPA1 is believed to play a role in pain, including pain related to nerve damage, cold allodynia and inflammatory pain.

Since the mis-regulation of ion channels is often associated with pathological conditions, it would be desirable to identify and make peptides or fragements thereof that can modulate one or more functions of ion channels including TRP channels. Such peptides and fragments thereof have a variety of in vitro and in vivo uses for treating and preventing conditions, such as pain and itch.

SUMMARY OF THE INVENTION

TRPA1, an ion channel expressed in pain sensing neurons, plays an essential role in pain and itch. The present invention is based upon the finding that Tmem100 (also known as Pirt2 and used interchangeably herein), a membrane protein, functions as a regulator of TRPA1. The present invention discloses a cell permeable peptide (CPP) derived from Tmem100 mutant protein (T100-Mut; also known as P2-MutCPP and used interchangeably herein) that strongly inhibits the activity of TRPA1 and blocks acute and chronic pain. Accordingly, the present invention describes therapeutic agents for pain and itch.

The invention features a method for treating or preventing a condition associated with TRPA1 function or for which reduced TRPA1 activity can reduce the severity, comprising administering an effective amount of a Tmem100 mutant polypeptide, or fragment thereof. For example, the effective amount of the Tmem100 mutant polypeptide comprises a 0.1-1,000 µl dose of 0.1-1,000 µM human T100-Mut peptide, e.g., 10 µl dose of 10-200 µM human T100-Mut peptide. Ultimately, the attending physician or veterinarian will decide the appropriate amount and dosage regimen. The Tmem100 mutant polypeptide is administered once per month, twice per month, once per week, twice per week, once per day or every 12 hours, every 8 hours, every 4 hours, every 2 hours, or every hour.

The invention features a method of preventing, treating, or alleviating symptoms of a disease or condition associated with TRPA1 function or for which reduced TRPA1 activity can reduce the severity, comprising administering to a subject in need thereof a Tmem100 mutant polypeptide, or fragment thereof.

The invention features a method of inhibiting TRPA1 function in a cell, comprising administering to the cell an effective amount of a Tmem100 mutant polypeptide, or fragment thereof, thereby inhibiting TRPA1 function in the cell.

The TRPA1 function is an association with TRPV1. The Tmem100 mutant polypeptide, or fragment thereof, enhances the association of TRPA1 with TRPV1.

The TRPA1 function is an inward TRPA1-mediated current, an outward TRPA1-mediated current, TRPA1-mediated ion flux or TRPA1-mediated neuronal hyperexcitability.

The Tmem100 mutant polypeptide comprises a polypeptide with one or more alterations in the amino acid sequence of SEQ ID NO: 1 or SEQ ID NO: 2, or fragments thereof.

The Tmem100 mutant polypeptide comprises an amino acid sequence selected from the group consisting of: SEQ ID NO: 5, SEQ ID NO: 6, SEQ ID NO: 7, SEQ ID NO: 8, SEQ ID NO: 17, or a fragment thereof.

The Tmem100 mutant polypeptide, or fragment thereof, is provided to a cell and the cell is a sensory neuron.

The cell body of the sensory neuron resides in the dorsal root ganglia (DRG).

The method is used to prevent, treat, or alleviate symptoms of pain.

The method is used to prevent, treat, or alleviate symptoms of itch. In one embodiment, the pain is acute pain or chronic pain.

The Tmem100 mutant polypeptide, or fragment thereof, is administered in combination with one or more agents.

The Tmem100 mutant polypeptide, or fragment thereof, is administered in combination with one or more of a TRPV1 inhibitor, a TRPV3 inhibitor, a TRPV4 inhibitor, or a TRPM8 inhibitor.

The invention features a pharmaceutical agents for treating or preventing a condition involving activation of TRPA1 or for which reduced TRPA1 activity can reduce the severity, comprising an effective amount of a Tmem100 mutant polypeptide, or fragment thereof.

The Tmem100 mutant polypeptide comprises a polypeptide with one or more alterations in the amino acid sequence of SEQ ID NO: 1 or SEQ ID NO: 2, or fragments thereof.

The Tmem100 mutant polypeptide comprises an amino acid sequence selected from the group consisting of: SEQ ID NO: 5, SEQ ID NO: 6, SEQ ID NO: 7 and SEQ ID NO: 8, or fragments thereof.

In another aspect, the invention features an isolated polypeptide comprising an amino acid sequence selected from the group consisting of: SEQ ID NO: 5, SEQ ID NO: 6, SEQ ID NO: 7 and SEQ ID NO: 8, or fragments thereof.

The invention features an isolated polypeptide encoded by a nucleic acid sequence comprising a nucleotide sequence selected from the group consisting of: SEQ ID NO: 9, SEQ ID NO: 10, SEQ ID NO: 11 and SEQ ID NO: 12, or fragments thereof.

The invention features an isolated nucleic acid comprising a nucleotide sequence selected from the group consisting of: SEQ ID NO: 9, SEQ ID NO: 10, SEQ ID NO: 11 and SEQ ID NO: 12, or fragments thereof.

The invention features an isolated nucleic acid comprising a nucleotide sequence which encodes a polypeptide comprising an amino acid sequence selected from the group consisting of: SEQ ID NO: 5, SEQ ID NO: 6, SEQ ID NO: 7 and SEQ ID NO: 8, or fragments thereof.

The invention features an expression vector, which replicates in at least one of a prokaryotic cell and eukaryotic cell, comprising the nucleic acid of any one of the above aspects.

The invention features a cell comprising the expression vector of claim and expressing said polypeptide.

The invention features a method of producing a polypeptide comprising culturing the cell of in a cell culture medium to express said polypeptide.

Definitions

As used herein, the singular forms "a", "an", and "the" include plural forms unless the context clearly dictates otherwise.

Unless specifically stated or obvious from context, as used herein, the term "or" is understood to be inclusive.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or characteristics of that which is recited is not changed by the presence of more than that which is recited, but excludes prior art embodiments.

As used herein, the term "administering" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenterally, intraperitoneally, intrathecal, intradermal), by topical application, or by inhalation (e.g., oral or nasal). Pharmaceutical preparations are, of course, given by forms suitable for each administration route.

As used herein, the term "agent" is meant small molecule chemical compound, antibody, nucleic acid molecule, or polypeptide, or fragments thereof. The terms "compound" and "agent" are used interchangeably to refer to the peptides or fragments thereof of the invention. The compounds of the present invention are peptides or fragments thereof. Such compounds can bind to and inhibit a function of TRPA1. Other exemplary compounds are nucleic acids, for example, TRPA1 antisense oligonucleotides or TRPA1 RNAi constructs. Such compounds can inhibit the expression of TRPA1, thereby inhibiting the activity of TRPA1. Other exemplary compounds that act as inhibitors include ribozyme. As used herein, the term "composition" is meant any compound or agent of the invention in pharmaceutical formulation and is used interchangeably with compound and agent.

As used herein, the term "analog" is meant an agent that is not identical, but has analogous functional or structural features. An exemplary analog is a peptide, peptide fragment or mutant with similar bioactive, physical, or chemical properties to agents of the invention.

As used herein, the terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

As used herein, the term "combination" embraces groups of compounds or non-drug therapies useful as part of a combination therapy.

As used herein, the term "disease" is meant any condition or disorder that damages or interferes with the normal function of a cell, tissue, or organ.

As used herein, an "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA 1 antagonist of the present invention, includes an amount of a TRPA1 antagonist effective to decrease one or more in vitro or in vivo function of a TRPA1 channel. Exemplary functions include, but are not limited to, membrane polarization (e.g., an antagonist promotes hyperpolarization of a cell), ion flux, ion concentration in a cell, outward current, and inward current. Agents that antagonize TRPA1 function include agents that antagonize an in vitro or in vivo functional activity of TRPA1. When a particular functional activity is only readily observable in an in vitro assay, the ability of an agent to inhibit TRPA1 function in that in vitro assay serves as a reasonable proxy for the activity of that agent. An effective amount is an amount sufficient to inhibit a TRPA1-mediated current and/or the amount sufficient to inhibit TRPA1 mediated ion flux.

The TRPA1 inhibitors of the present invention are characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment contains 10, 20, 30, 40, 50, 60, 70, 80, 90, or 100, 200, 300, 400, 500, 600, 700, 800, 900, or 1000 nucleotides or amino acids.

As used herein, the term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

As used herein, the term "pharmaceutically acceptable" refers to approved or approvable by a regulatory agency of the Federal or a state government or listed in the U.S. Pharmacopeia or other generally recognized pharmacopeia for use in animals, including humans.

As used herein, the term "preventing" is art-recognized, and when used in relation to a condition, such as a local recurrence (e.g., pain), a disease such as cancer, a syndrome complex such as heart failure or any other medical condition, is well understood in the art, and includes administration of an agent which reduces the frequency of, or delays the onset of, symptoms of a medical condition in a subject relative to a subject which does not receive the agent. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

"Peptides," "polypeptides," and "oligopeptides" are chains of amino acids (typically L-amino acids; however, D-amino acids are also contemplated) whose alpha carbons are linked through peptide bonds formed by a condensation reaction between the carboxyl group of the alpha carbon of one amino acid and the amino group of the alpha carbon of another amino acid. In some cases, the terminal amino acid at one end of the chain (for example, the amino terminal) has a free amino group, while the terminal amino acid at the other end of the chain (for example, the carboxy terminal) has a free carboxyl group. As such, the term "amino terminus" (abbreviated N-terminus) refers to the free alpha-amino group on the amino acid at the amino terminal end of the peptide, or to the alpha-amino group (imino group when participating in a peptide bond) of an amino acid at any other location within the peptide. The term "carboxy terminus" (abbreviated C-terminus) refers to the free carboxyl group on the amino acid at the carboxy terminal end of a peptide, or to the carboxyl group of an amino acid at any other location within the peptide.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

By "polypeptide" is meant a polymer in which the monomers are amino acid residues that are joined together through amide bonds. When the amino acids are alpha-amino acids, either the L-optical isomer or the D-optical isomer can be used, the L-isomers being preferred in nature. The term "polypeptide" or "protein" as used herein encompasses any amino acid sequence and includes, but may not be limited to, modified sequences such as glycoproteins or amidated proteins. The term "polypeptide" is specifically intended to cover naturally occurring proteins, as well as those that are recombinantly or synthetically produced. Exemplary polypeptides include gene products, naturally-occurring proteins, homologs, orthologs, paralogs, fragments, and other equivalents, variants and analogs of the foregoing.

In some cases, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal, or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used herein, the term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, and multiplying the result by 100 to yield the percentage of sequence identity. Methods to calculate sequence identity are known to those of skill in the art and described in further detail below.

As used herein, the terms "stringent conditions" or "stringent hybridization conditions" refer to conditions which promote specific hybridization between two complementary polynucleotide strands so as to form a duplex. Stringent conditions can be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it is desirable to increase the stringency of the hybridization conditions to be about equal to the Tm for a particular duplex. In certain cases, stringent hybridization conditions include a wash step of 0.2×SSC at 65° C.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) Proteins, W.H. Freeman and Company, incorporated herein by reference. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). As used herein "peptide mimetics" refers to organic compounds which are structurally similar to peptides. The peptide mimetics are typically designed from existing peptides to alter the molecule's characteristics. Improved characteristics can involve, for example, improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification. Such compounds are often developed with the aid of computerized molecular modeling.

Peptide mimetics that are structurally similar to therapeutically useful peptides may be used to produce an equivalent therapeutic or prophylactic effect. See, e.g., Avan et al., 2014 Chemical Society Reviews, 43: 3575-3594, incorporated herein by reference. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

As described herein, in some aspects, the peptides described herein are modified. For example, in some cases, the conventional peptide bond (i.e., the chemical bond formed between two molecules when the carboxyl group of one molecule reacts with the amino group of the other molecule, releasing a molecule of water (H$_2$O)) between two amino acids is changed to a different linkage to render the resulting molecule more stable in biological fluids.

In some cases, the peptide is a cyclic peptide, wherein the amino termini and carboxyl termini, amino termini and side chain, carboxyl termini and side chain, or side chain and side chain are linked with a covalent bond that generates a ring. Cyclic peptides are extremely resistant to the process of digestion, enabling them to survive in the human digestive tract. This trait makes cyclic peptides attractive for protein-based drugs are delivered orally.

In other cases, the amino acids of the peptides described herein are modified. For example, modification may involve deletion of amino acids, chemical modification of certain amino acids (for example, amidation, acetylation, phosphorylation, glycosylation, formation of pyroglutamate, oxidation/reduction of sulfa group on a methionine, or addition of similar small molecules) to certain amino acids.

In some cases, the Tmem 100 mutant polypeptides described herein comprise one or more lipid modifications. At least five different types of lipids can be covalently attached to proteins: fatty acids, isoprenoids, sterols, phospholipids, and glycosylphosphatidyl inositol (GPI) anchors. See, e.g., M. Resh, 2013 Current Biology, 23(10): pR431-pR435, incorporated herein by reference. Proteins can contain more than one type of lipid, e.g., myristate+palmitate, palmitate+cholesterol, or farnesyl+palmitate. Each type of lipid moiety is attached by a different lipid transferase and each modification confers distinct properties to the modified protein. The most common outcome of lipid modification is an increased affinity for membranes. However, attachment of myristoyl or prenyl groups can also promote intramolecular and intermolecular protein-protein interactions. Another key concept is reversibility. The covalent linkage between a protein and either thioester-linked palmitate or a GPI anchor can be broken by the actions of thioesterases and phospholipases, respectively. By contrast, neither myristate nor the isoprenoids farnesyl or geranylgeranyl are physically removed from a modified protein.

Optionally, the Tmem 100 mutant polypeptides described herein comprise any lipid modification, e.g., palmitoyl (Pal) or myristyl (Myr) groups, to make the peptides cell permeable. Suitable locations for modification with lipophilic groups include the N-terminus and/or C-terminus of the peptide; however, the peptide may be lipid modified at any amino acid position within the peptide.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

As used herein, the terms "TRPA1", "TRPA1 protein", and "TRPA1 channel" are used interchangeably throughout the application. These terms refer to an ion channel (e.g., a polypeptide) comprising the amino acid sequence set forth in GenBank Accession No. NP_015628 (human); Accession: NP_808449 (mouse); Accession: NP_997491 (rat), or an equivalent polypeptide, or a functional bioactive fragment thereof.

As used herein, the term "Tmem100" (or Pirt2) refers to a membrane protein that functions as a regulator of TRPA1. In certain cases, Tmem100 refers to a polypeptide comprising, consisting of, or consisting essentially of, the amino acid sequence set forth in SEQ ID NO: 1 (GenBank Ref N. NP_001093110; shown below) or SEQ ID NO: 2 (GenBank Ref No. NP_080709, shown below):

(Homo sapiens)
SEQ ID NO: 1
```
  1    MTEEPIKEIL  GAPKAHMAAT  MEKSPKSEVV  ITTVPLVSEI  QLMAATGGTE  LSCYRCIIPF
 61    AVVVFIAGIV  VTAVAYSFNS  HGSIISIFGL  VVLSSGLFLL  ASSALCWKVR  QRSKKAKRRE
121    SQTALVANQR  SLFA
```

(Mus musculus)
SEQ ID NO: 2
```
  1    MTEESTKENL  GAPKSPTPVT  MEKNPKREVV  VTTGPLVSEV  QLMAATGGAE  LSCYRCIIPF
 61    AVVVFITGIV  VTAVAYSFNS  HGSIISIFGL  VLLSSGLFLL  ASSALCWKVR  QRNKKVKRRE
121    SQTALVVNQR  CLFA
```

Tmem100 includes polypeptides that retain a function of Tmem100 and comprise (i) all or a portion of the amino acid sequence set forth in SEQ ID NO: 1 or SEQ ID NO: 2; (ii) the amino acid sequence set forth in SEQ ID NO: 1 or SEQ ID NO: 2 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO:1 or SEQ ID NO: 2; and (iv) functional fragments thereof. Polypeptides of the disclosure also include homologs, e.g., orthologs and paralogs, of SEQ ID NO: 1 or SEQ ID NO: 2.

The term "Tmem100 mutant" is meant to refer to polypeptide comprising one or more alterations in SEQ ID NO: 1 or SEQ ID NO: 2, or fragments thereof. An alteration can be one or more amino acid additions, deletions or substitutions.

A Tmem100 mutant comprises a polypeptide comprising, consisting of, or consisting essentially of, the amino acid sequence set forth in SEQ ID NO: 5 or SEQ ID NO: 6, or fragments thereof, as shown below:

(Homo sapiens)
SEQ ID NO: 5
MTEEPIKEILGAPKAHMAATMEKSPKSEVVITTVPLVSEIQLMAATG
GTELSCYRCIIPFAVVVFIAGIVVTAVAYSFNSHGSIISIFGLVVLS
SGLFLLASSALCWKVRQRSKKAQQQESQTALVANQRSLFA (Mus musculus)
SEQ ID NO: 6
MTEESTKENLGAPKSPTPVTMEKNPKREVVVTTGPLVSEVQLMAATG
GAELSCYRCIIPFAVVVFITGIVVTAVAYSFNSHGSIISIFGLVLLS
SGLFLLASSALCWKVRQRNKKVQQQESQTALVVNQRCLFA A Tmem100 mutant comprises a polypeptide comprising, consisting of, or consisting essentially of, the amino acid sequence set forth in SEQ ID NO: 7 or SEQ ID NO: 8, or fragments thereof, as shown below. Preferably, these Tmem 100 mutant polypeptides comprise palmitoyl (Pal) or myristyl (Myr) groups at their N-terminus to make them cell permeable:

(Homo sapiens)
SEQ ID NO: 7
WKVRQRSKKAQQQESQTALVANQRSLFA (Mus musculus)
SEQ ID NO: 8
WKVRQRNKKVQQQESQTALVVNQRCLFA The term "Tmem100" (or TMEM100) further refers to a nucleic acid encoding a polypeptide of the invention, e.g., a nucleic acid comprising a sequence consisting of, or consisting essentially of, the polynucleotide sequence set forth in SEQ ID NO: 3 (GenBank Ref. No. NM_001099640, shown below) or SEQ ID NO: 4 (GenBank Ref. No. NM_026433, shown below):

(Homo sapiens)
SEQ ID NO: 3
```
  1   cagttgcttc  tacaaaaccc  gtgaaagttc  tctgtccaaa  agccttgttg  gtcccgcggt
 61   acatgcttcc  tgttcccaga  gagattcacc  cttgggcttt  cctatcagtc  ttccctaaag
121   ttggctgctc  ctgtgtcctg  tcacataaaa  ctgtgaaccg  aggtctccga  cttacgtcat
181   gtcagtcaca  gcagggtgag  gctccacaag  tgtgagttct  ggcccctgct  gctttccttt
241   caaatgcagt  ttacagttta  ttatggtatt  ggacacccca  tgctccttac  tgcattggct
301   tgggtaaga   aggagtgaaa  attagtgtgc  gaacctgaaa  acctagaatt  tctgattggg
361   actgaagaaa  acctttgtgc  tgcagtcagt  ccccgagcca  gacgcctgtg  actctcttca
421   catgaaata   gatgactatc  cacagtaaaa  gcaaaattaa  aaagtgactt  gtgaaaaata
481   tcctccatgc  tcctcttacc  aagcctgcaa  cttaaaacct  atggtttaaa  ctgtgctttc
541   aattatctgg  aggaggccag  cactgatgag  cccatcctga  gccagtcatt  ttaaggccag
601   tgctacctaa  ctgagacaag  gctaatctgg  tcgccttgct  gttagaggct  cttttcccaga
661   agttggacga  agaggctcag  gcgttgctgt  ttcttgtctt  ccaagtcaag  tggttactct
```

-continued

```
 721  ggtaatggat tgcctctctc cgagctttca ccctggtgag actgtccaga tctagtctgt
 781  aaacccagct tagaagcact gttgtaaaaa tgactgaaga gcccatcaag gagatcctgg
 841  gagccccaaa ggctcacatg gcagcgacga tggagaagag ccccaagagt gaagttgtga
 901  tcaccacagt ccctctggtc agtgagattc agttgatggc tgctacaggg ggtaccgagc
 961  tctcctgcta ccgctgcatc atccccctttg ctgtggttgt cttcatcgcc ggcatcgtgg
1021  tcaccgcggt ggcttacagc ttcaattccc atgggtctat tatctccatc tttggcctgg
1081  ttgttctgtc atctggactt ttttttactag cctccagtgc cttgtgctgg aaagtgagac
1141  aaaggagcaa gaaagccaag agacgggaga gtcaaacagc tctcgtggca aatcagagaa
1201  gcttgtttgc ttgagactga atacgaccaa atgggccatt gggcctggaa aacgtgctct
1261  gactttgtca cccaattcac ccagaaccat ggtgggagag aacagacttg gcgttggagc
1321  agactggaag aatgggggtg ggagggtgga ggggcttctc ctttgtgagg aatgactcat
1381  gtcttcttta acgacaaaact taaccctaag ggctacttct gagactgaaa aatcagcttt
1441  ctatttacat gaaacacttt gggggtcatg ggagtgcaca gcattagaca gtatttggtt
1501  caccctgtaa agtagccaag aaaagatgag aaaaatcaag ataggcctgg cacactagac
1561  atttgcctcc aaaagaaata acctacagtc ttaagatgta tcataaaaat gttctgccaa
1621  ggatctaaat taccttgggt ttcgcatatg tctatgaaat tctgtgataa ttttttttcaa
1681  tacattgatt cactggcgtc tgttttcatt ttatactttt aataactcat cactggtggt
1741  actttatctt gaaaagtaat atttttttata ttttaacatt ggacagtgtt agccagttgt
1801  aatgatgtat cagaagtaaa gaaaaaccca ttaaagttat agctaataga tgctgttggg
1861  ggttaaatta atagtaaaat aatccaatat agcactttg atgattttta tataaaagtc
1921  aactgtacat ttcattcaga ataataaaata cttattgctg ctaaaacttc ttaaatggtt
1981  gtttctgcta tagttatttc tattgcagtt ccaaattgcc atcttccctt gtctcatttg
2041  caagttctca attgtatttc tctcaaatgg acaggttcct tctttactgg aggattttg
2101  tttttatcat attggttttt cattacttct gaatagtctt aattacgttt actaaattct
2161  aaaggatttc tgtgctatta taattaggaa atcaacgtct ttggtcagga actttataat
2221  gtgctattaa atgtatatta catttttgtg gaaaaaaaaa aaaaaaaaa
```

(Mus musculus)
SEQ ID NO: 4

```
   1  tctgcagctt cacactacaa aagagtgata tcgaagacta ggttagagaa aaccataaaa
  61  aagaatgctt gcataaggat tttaaacggg ggaaagaaaa caggagagat ttttagtgac
 121  ttttttaaata attgggttat gatggattca ctcctgtaat tacagtggat ggtgtgggca
 181  cggaaaaaaa aatagaaaag aaaaggaaaa cgtagagtaa aatacaacag cgagtaagga
 241  atttcctttc accaaattgt ctccggtccc ttaatggtct gtaaatcttg ctgagtactt
 301  tgtgtacggt ccctagcatg gtgatttgca tcccactgtc ggcctcgctg ttggccgccg
 361  cttgctgctg tctcagtcca cttctggctg agaaagaggc aatccctggt ctgtcctttt
 421  accaatgccc agtgggtgac aggctctttc ccagaagttg aacggagcta cgctggcaga
 481  tccctctctc ccaagtcaag tggcctctct ggtaatggac tgcctttctg tgagcttgca
 541  tcctgaccag gctttccaaa tctagcctgt gaagcgagat aagaaaaatc ccacagaaga
 601  aaaaaaaatg accgaagaat ccacaaaaga gaacctggga gctccaaaat ctcccacacc
 661  tgtgacaatg gagaaaaacc ccaagaggga agttgtggtc accacgggac ccttggtcag
 721  cgaggttcag ctgatggccg ccaccggggg tgccgaactc tcctgctacc gctgcatcat
```

-continued

```
 781   cccctttgcc gtggtggtct tcatcactgg gattgtggtc accgctgtgg cttacagctt
 841   caattcccat ggttccatca tctccatctt cggcctggtc cttctgtcct ccggactgtt
 901   tttactagcc tccagtgcct tgtgctggaa ggtgagacaa aggaacaaga aagtcaagag
 961   acgcgagagt cagaccgctc ttgtggtaaa tcagaggtgc ttgtttgctt aagactgagt
1021   aagagcaaac gcgaacgctc acccgcccac actgctctaa ctcagtgaac tcattcatag
1081   gaaaccagcc cggtaccgga tgagctcaac tttcgaatga actaccaaaa tgaaaaatag
1141   ggcatagaga ggactgaaaa tgaggggtca agacggttcc cccttggtag ggaataactc
1201   atctttaacg acaaacttaa ccctaagggc tatttctaac acagacagag gaatcagctt
1261   gcttttcctg ttaaacgttt agggagtgtg ggagatgcac agcattaaat aacagttggt
1321   tccatttaga aagtacccaa gggaagaatg gacaaataat gagagccctg gcaagtggtg
1381   ttataaaaac gttccaccaa aagcctacat tggcttggca ttcccacgta cctaagaagt
1441   tctgttatat atatacatat atatttttc caataagttg attctttgcc ccccccttt
1501   taaaagaatt ttcacttttca gtaacatcac tagaggtact ttattttgaa gaatagacta
1561   atattttta tattttaaca atggacaatt gtagatggtt gtaatgatat gtcagaagaa
1621   aacagaaatg taggtaacac agatgacaca gggacagtta aattaatatt gaataatcc
1681   aatctagcac ctttgatggc ttttatacaa aagttcagtg tgcatttcac tcaaaataat
1741   aaatgctcat ggctgctgaa actt
```

The term "Tmem100 mutant" refers to a nucleic acid encoding a polypeptide of the invention, e.g., a nucleic acid comprising a sequence consisting of, or consisting essentially of, the polynucleotide sequence set forth in SEQ ID NO: 9 or SEQ ID NO: 10.

(Homo sapiens)
SEQ ID NO: 9
```
atgactgaagagcccatcaaggagatcctgggagccccaaaggctca catggcagcgacgatggagaagagccccaagagtgaagttgtgatca ccacagtccctctggtcagtgagattcagttgatggctgctacaggg ggtaccgagctctcctgctaccgctgcatcatccccttgctgtggt tgtcttcatcgccggcatcgtggtcaccgcggtggcttacagcttca attcccatgggtctattatctccatctttggcctggttgttctgtca tctggacttttttttactagcctccagtgccttgtgctggaaagtgag acaaaggagcaagaaagcccagcaacaggagagtcaaacagctctcg tggcaaatcagagaagcttgtttgcttga
```

(Mus musculus)
SEQ ID NO: 10
```
atgaccgaagaatccacaaaagagaacctgggagctccaaaatctcc cacacctgtgacaatggagaaaaccccaagagggaagttgtggtca ccacgggacccttggtcagcgaggttcagctgatggccgccaccggg ggtgccgaactctcctgctaccgctgcatcatccccttgccgtggt ggtcttcatcactgggattgtggtcaccgctgtggcttacagcttca attcccatggttccatcatctccatcttcggcctggtccttctgtcc tccggactgttttttactagcctccagtgccttgtgctggaaggtgag
```

-continued

```
acaaaggaacaagaaagtccagcaacaggagagtcagaccgctcttg tggtaaatcagaggtgcttgtttgcttaa
```

The term "Tmem100 mutant" refers to a nucleic acid encoding a polypeptide of the invention, e.g., a nucleic acid comprising a sequence consisting of, or consisting essentially of, the polynucleotide sequence set forth in SEQ ID NO: 11 or SEQ ID NO: 12.

(Homo sapiens)
SEQ ID NO: 11
```
tggaaagtgagacaaaggagcaagaaagcccagcaacaggagagtca aacagctctcgtggcaaatcagagaagcttgtttgcttga
```

(Mus musculus)
SEQ ID NO: 12
```
tggaaggtgagacaaaggaacaagaaagtccagcaacaggagagtca gaccgctcttgtggtaaatcagaggtgcttgtttgcttaa
```

A nucleic acid of the disclosure can comprise all, or a portion of: the nucleotide sequence of SEQ ID NO: 3, 4, 9, 10, 11 or 12; a nucleotide sequence at least 70%, 75%, 80%, 90%, 95%, 96%, 97%, 98% or 99% identical to SEQ ID NO: 3, 4, 9, 10, 11 or 12; a nucleotide sequence that hybridizes under stringent conditions to SEQ ID NO: 3, 4, 9, 10, 11 or 12; nucleotide sequences encoding polypeptides that are functionally equivalent to polypeptides of the disclosure; nucleotide sequences encoding polypeptides at least about 70%, 75%, 80%, 85%, 90%, 95%, 98%, 99% homologous or identical with an amino acid sequence of SEQ ID NO: 3, 4, 9 or 10; nucleotide sequences encoding polypeptides having an activity of a polypeptide of the disclosure and having at least about 70%, 75%, 80%, 85%, 90%, 95%, 98%, 99% or more homology or identity with SEQ ID NO: 3, 4, 9, 10, 11 or 12; nucleotide sequences that differ by 1 to about 2, 3, 5, 7, 10, 15, 20, 30, 50, 75 or more nucleotide substitutions, additions or deletions, such as allelic variants, of SEQ ID NO: 3, 4, 9, 10, 11 or 12; nucleic acids derived from and evolutionarily related to SEQ ID NO: 3, 4, 9, 10, 11 or 12; and complements of, and nucleotide sequences resulting from the degeneracy of the genetic code, for all of the foregoing and other nucleic acids of the invention. Nucleic acids of the disclosure also include homologs, e.g., orthologs and paralogs, of SEQ ID NO: 3, 4, 9 or 10 and also variants of SEQ ID NO: 3, 4, 9, 10, 11 or 12 which have been codon optimized for expression in a particular organism (e.g., host cell). Where not explicitly stated, one of skill in the art can readily assess whether Tmem100 refers to a nucleic acid or a protein.

Tmem100 weakens the association of TRPA1 and TRPV1 and thereby releases the inhibition of TRPA1 by TRPV1. A "Tmem100 mutant" exerts the opposite effect, i.e. it enhances the association of TRPA1 and TRPV1 and inhibits TRPA1.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The term "treating" includes prophylactic and/or therapeutic treatments. The term "prophylactic or therapeutic" treatment is art-recognized and includes administration to the host of one or more of the subject agents. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any composition, agents or methods provided herein can be combined with one or more of any of the other compositions, agents and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a schematic drawing of the structure of Tmem100. Tmem100 is a two-transmembrane protein with a putative TRPA1 binding site (KRR) at its C-terminus. Both the N- and C-termini are intracellular whereas the loop region is extracellular. "PM": plasma membrane. FIG. 1B is a graph showing that Tmem100-expressing cells comprise 24% of L4-L6 DRG neurons. They are predominantly small-diameter, but medium- to large-diameter neurons are also present. The average diameter of Tmem100-expressing neurons is 15.7 µm, and the median is 14.3 µm (DRG from 3 mice). FIG. 1C shows images of double staining of Tmem100-GFP with other DRG markers. Bar: 50 µm. FIG. 1D is a table of the quantification of co-expression of Tmem100 and other DRG markers (DRG from 3 mice; data are presented as mean±SEM). FIGS. 1E and 1F are diagrams showing the relationship of Tmem100 with other DRG markers. Tmem100 is a marker for the majority of CGRP DRG neurons (FIG. 1E); most TRPA1$^+$ DRG neurons express Tmem100 (FIG. 1F).

FIG. 2A is a schematic depiction of the Tmem100 conditional KO strategy. FIG. 2B shows images of the deletion of the Tmem100 gene in conditional KO lines was verified by anti-Tmem100 immunostaining of DRG. Bar: 50 µm. FIG. 2C is a graph of the baseline mechanical sensitivity of Tmem100 CKO (Avil-Cre;Tmem100$^{fl/fl}$) mice is similar to that of the control group (Avil-Cre;Tmem100$^{+/+}$ mice). At the forces tested, there was no significant difference in the response rate among Tmem100 CKO and the control group (n=10 for CKO and 13 for control). FIG. 2D is a graph indicating that Tmem100 CKO mice showed decreased acute nocifensive behavior after 0.2% MO injection. (White bar: Avil-Cre;Tmem100$^{+/+}$; grey bar: Tmem100; black bar: Avil-Cre;Tmem100$^{fl/fl}$. Total time of licking and flinching: 86±6.2 sec in Avil-Cre;Tmem100$^{+/+}$; 86±11.1 sec in Tmem100$^{fl/fl}$; 57±9.3 sec in Tmem100 CKO; n=13 for Avil-Cre;Tmem100$^{+/+}$ and Tmem100$^{fl/fl}$; n=10 for Tmem100 CKO) *p<0.05, **p<0.01. FIG. 2E is a graph indicating that Tmem100 CKO mice showed decreased mechanical hyperalgesia after MO injection (n=11 for Avil-Cre;Tmem100$^{+/+}$; 9 for Tmem100$^{fl/fl}$; 10 for Tmem100 CKO).

FIG. 2F is a graph showing Capsaicin-induced nocifensive behaviors (0.6 µg) are similar between Tmem100 CKO and the control group (Avil-Cre;Tmem100$^{+/+}$ mice). Time of licking and flinching: 45±5.7 sec in Avil-Cre;Tmem100$^{+/+}$ v.s 53.7±8.3 sec in Tmem100 CKO; n=12 in CKO and 10 in control; p=0.40). FIGS. 2G and 2H are graphs indicating that Tmem100 CKO mice show decreased mechanical hyperalgesia but intact thermal hyperalgesia after CFA injection. One and 2 days after CFA injection, Tmem100 CKO mice had higher mechanical thresholds than both control groups, but the response to painful thermal stimuli remained unchanged. (*p<0.05; p<0.01; *p<0.001; n=16 for Avil-Cre;Tmem100$^{+/+}$; 10 for Tmem100$^{fl/fl}$; 18 for Tmem100 CKO for (FIG. 2G); n=9 for Avil-Cre;

Tmem100$^{+/+}$; 10 for Tmem100$^{fl/fl}$; 11 for Tmem100 CKO for (FIG. 2H)). FIGS. 2I and 2J are graphs indicating that nocifensive responses in the hot plate and tail immersion tests were intact in Tmem100 CKO mice. At the indicated temperatures, there was no difference in the latency between CKO and control groups (Avil-Cre;Tmem100$^{+/+}$ mice) (n=9 and 13 for control and CKO, respectively, in (FIG. 2I); n=13 and 10 for control and CKO, respectively, in (FIG. 2J)). All statistics are unpaired t-tests except for (FIG. 2C), in which two-way ANOVA with Bonferroni's post-hoc test is used. Data are presented as mean±SEM.

FIG. 3A is a graph showing that TRPA1 activity in the DRG neurons of Tmem100 CKO mice was reduced whereas TRPV1 activity was relatively unchanged. The percentage of neurons responding to 10 μM mustard oil (MO) and 250 μM cinnamaldehyde (CA) was lower in the CKO line whereas the percentage of neurons responding to 100 nM capsaicin (CAP) and 100 μM menthol were similar between the CKO and control groups. (Each reagent was tested greater than 3 times in 3 mice; greater than 300 IB4$^-$ cells were assessed in the MO, CA, and CAP group and greater than 297 cells were assessed in the MEN group. All statistics are unpaired t-tests. The error bars represent SEM; *$p<0.05$; $p<0.01$) FIG. 3B is a graph showing that the average current induced by 7 or 25 μM MO (1 min application) is lower in DRG neurons from Tmem100 CKO mice, whereas there is no significant difference when 150 μM MO is applied. The numbers in the columns represent the number of cells responding/the number of cells tested. More than 3 mice were tested from each group; all statistics are an unpaired t-tests. All error bars represent SEM; $p<0.01$). FIG. 3C shows representative traces of MO-induced currents from Avil-Cre;Tmem100$^{+/+}$ and Avil-Cre; Tmem100$^{fl/fl}$ mice. FIG. 3D is a graph indicating the average current induced by 100 nM CAP (30 sec application) is similar among DRG neurons from Tmem100 CKO and control mice. The numbers in the columns represent the number of cells responding/the number of cells tested. More than 3 mice were tested from each group; all statistics are unpaired t-tests. The error bars represent SEM. FIG. 3E shows representative traces of CAP-induced currents from Avil-Cre;Tmem100$^{+/+}$ and Avil-Cre;Tmem100$^{fl/fl}$ mice. FIG. 3F is a graph showing MO (10 μM)-gated whole-cell voltage clamp (Vh=−60 mV) current densities in TRPA1+TRPV1 (1:1)- and TRPA1+TRPV1+Tmem100 (1:1:4)-expressing CHO cells. The number of cells analyzed and those that responded are indicated within bars. The statistic is an unpaired t-test ($p<0.01$). The error bars represent SEM. FIG. 3G is a graph showing MO (10 μM)-evoked Ca$^{2+}$ influx into TRPA1+TRPV1 (1:1)- and TRPA1+TRPV1+Tmem100 (1:1:4)-expressing CHO cells. The numbers of cells responding are indicated within bars. The statistic is an unpaired t-test (*$p<0.001$). Data are presented as mean±SEM.

FIGS. 4A and 4B are graphs showing MO (10 μM)—(A) and CAP (100 nM)-induced (B) single-channel open probability (P$_o$) of the main conductance at Vh=−60 mV in CHO cells expressing TRPA1 vs. TRPA1+Tmem100 (T100) (1:4 molar ratio) and TRPA1+TRPV1 (1:1) vs. TRPA1+TRPV1+Tmem100 (1:1:4). The configuration is cell-attached patch, and the number of cells that responded among those analyzed is indicated within bars. The statistic is one-way ANOVA with Bonferroni's post-hoc test for comparison between all columns ($p<0.01$; *$p<0.001$); error bars represent SEM. FIGS. 4C and 4D show representative single-channel recording during 5 sec at Vh=−60 mV for MO-gated current (FIG. 4C) and 4 sec for CAP-gated current (FIG. 4D) in TRPA1+ TRPV1− and TRPA1+TRPV1+Tmem100-expressing CHO cells; c is the closed state, o1, o2, and o3 show open states for 3 independent channels in the patch. FIG. 4E is a table of summary of data on single-channel conductance (pS) and effects on Po changes of Tmem100 (T100) for the given agonists and genes expressed. The values of single-channel conductance were derived from FIG. 12A-12K. Data are presented as mean±SEM.

FIG. 5A-FIG. 5F demonstrate that Tmem100 decreases the interaction between TRPA1 and TRPV1 whereas the Tmem100-3Q mutant enhances it. FIG. 5A is an image of a Co-IP with Tmem100 and TRPV1 antibodies and Western blotting with TRPA1, TRPV1, and Tmem100 antibodies in mouse DRG lysates. Tmem100, TRPA1, and TRPV1 form a complex in DRG neurons. FIG. 5C is an image of a Co-IP of TRPA1 and full-length myc-Tmem100 in TRPA1-V1 co-expressing cells. Tmem100 binds TRPA1 at different dilutions. FIG. 5D is an image of a GST pull-down with different TRPs and fragments of Tmem100 and Tmem100-3Q proteins. TRPV1 is pulled down by the C-termini of both WT Tmem100 (GST-C-WT) and Tmem100-3Q (GST-C-3Q). It is also pulled down by the N-terminus of WT Tmem100 (GST-N). However, TRPA1 is pulled down only by the C-terminus of WT Tmem100, whereas the Q-Q-Q mutation abolishes this interaction. The lysates from the cells expressing unconjugated GST (GST) and each TRP serve as negative controls. FIG. 5E is a graph showing FRET results with TIRF microscopy for the effects of Tmem100 on TRPA1-V1 interactions. All groups were transfected with TRPV1-CFP and TRPA1-YFP except for the Rho-pYC (as a positive control for maximal effects of the system) and M-V1 (negative control) groups, where Rho-pYC and membrane-tethered YFP+TRPV1-CFP, respectively, were transfected instead. FRET efficiencies were highest in Tmem100-3Q-transfected cells (A1-V1-3Q), followed by the empty vector-transfected groups (A1-V1), and were lowest in cells transfected with wild-type Tmem100 (A1-V1-WT). The statistic is one-way ANOVA (*$p<0.05$; $p<0.01$, *$p<0.001$). Data are presented as mean±SEM. FIG. 5F is a table showing a summary of the data from FIG. 5E.

FIGS. 6A and 6B are graphs showing MO (10 μM)—(FIG. 6A) and CAP (100 nM)-induced (FIG. 6B) single-channel open probability (P$_o$) of the main conductance at Vh=−60 mV in CHO cells expressing TRPA1 vs. TRPA1+Tmem100-3Q (T100-3Q) (1:4 molar ratio) and TRPA1+TRPV1 (1:1) vs. TRPA1+TRPV1+Tmem100-3Q (1:1:4). The statistic is one-way ANOVA as in FIG. 4; *$p<0.05$; **$p<0.01$; NS: no significant difference. FIGS. 6C and 6D show representative single-channel recording traces at Vh=−60 mV for MO—(FIG. 6C) and CAP-gated (FIG. 6D) current in TRPV1+ TRPA1-vs. TRPV1+TRPA1+Tmem100-3Q-expressing CHO cells. Traces are 4 sec long. FIG. 6E is a table summary of data on single-channel conductance (pS) and effects on P$_o$ changes of Tmem100-3Q for the given agonists and genes expressed. The values of single-channel conductance were derived from FIG. 12. FIG. 6F is a graph showing MO (10 μM)-gated whole-cell voltage clamp (Vh=−60 mV) current densities in TRPA1+TRPV1 (1:1)- and TRPA1+TRPV1+

Tmem100-3Q (1:1:4)-expressing CHO cells. Results: 138.9±29.92 pA/pF for TRPA1+TRPV1 vs. 39.16±12.5 pA/pF for TRPA1+TRPV1+Tmem100-3Q cells. The statistic is an unpaired t-test ($p<0.01$). FIG. 6G is a graph showing MO (10 µM)-evoked $Ca^{2+}$ influx into TRPA1+ TRPV1 (1:1)- and TRPA1+TRPV1+Tmem100-3Q (1:1:4)-expressing CHO cells. Results: 463.1±26.8 nM for TRPA1+TRPV1 vs. 321±18.2 nM for TRPA1+TRPV1+Tmem100-3Q cells. The numbers of cells responding/tested are indicated within bars. The statistic is an unpaired t-test (*$p<0.001$). Data are presented as mean±SEM.

FIG. 7A shows sequences of the cell-permeable peptide T100-Mut (SEQ ID NO: 8), scrambled peptide (SEQ ID NO: 15), T100-WT (SEQ ID NO: 14), and WT (SEQ ID NO: 13) C-terminal sequence of Tmem100 (WT). Myr: myristoylation. FIG. 7B is a graph of calcium imaging data from the T100-Mut-treated (200 nM) DRG neurons. (MO: 12±1.3% in scrambled vs. 4.6±0.9% in T100-Mut-treated group; CAP: 16±1.3% in scrambled vs. 15±6.5% in T100-Mut; DRG from 3 mice). FIG. 7C is a graph of calcium imaging data from HEK293T cells expressing TRPA1 and TRPV1. Pre-treatment of T100-Mut (200 nM) reduced the percentage of cells responsive to 500 nM MO, whereas T100-WT produced no such effect (18±2.8% in scrambled, 6±2.4% in T100-Mut, and 17±0.6%, repeated 3 times, *$p<0.05$). FIG. 7D is a graph of pre-treatment with T100-Mut (5 µl of 2 mM) alleviated MO-induced acute nocifensive behavior (n=6, **$p<0.01$) and mechanical hyperalgesia (0.1±0.03 g in scrambled vs. 0.4±0.11 g in T100-Mut; n=13, *$p<0.05$). FIG. 7E is a graph of pre-treatment with T100-Mut (5 µl of 2 mM) alleviated CFA-induced mechanical hyperalgesia (0.05±0.0 g in scrambled vs. 0.43±0.1 g in T100-Mut; n=10, ***$p<0.001$) but not thermal hyperalgesia (3.9±0.6 sec in scrambled vs. 4.3±0.5 sec in T100-Mut; n=10, p=0.63). FIG. 7F is a graph showing acute nocifensive behaviors induced by intradermal capsaicin injection (0.6 µg) were similar among the T100-Mut- and scrambled peptide-treated (2 mM) WT mice (70±11 sec in scrambled vs. 65±9 sec in T100-Mut; n=8, p=0.73). FIG. 7G is a graph showing that in wild-type mice injected with paclitaxel (Taxol), mechanical hyperalgesia was observed at day 7 post-injection. Hyperalgesia was attenuated by the intradermal injection of T100-Mut (n=7 for scrambled control peptide (open bar); n=8 for T100-Mut peptide (black bar); *$p<0.05$). FIGS. 7H and 7I showing that in TRPV1$^{-/-}$ mice, T100-Mut did not perturb MO-induced acute pain (FIG. 7H) and mechanical hyperalgesia (FIG. 7I), as observed in WT mice. (n=8, p=0.91 for (FIG. 7H) and 0.64 for (FIG. 7I)). All statistics are unpaired t-tests and data are presented as mean±SEM.

FIGS. 9A, 9B and 9C are images showing Tmem100-myc signal was only visible in the plasma membrane when F11 cell lines transfected with a Tmem100-myc construct were treated with detergent (FIG. 9A). Similar results were obtained in Tmem100-transfected cell lines treated with an anti-Tmem100 antibody targeting the N-terminus (FIG. 9B). No signal was detected without detergent treatment (FIG. 9C). FIG. 9D shows images of a comparison of bright field image and c-myc staining of F11 cell lines transfected with Tmem100-myc suggested that Tmem100 primarily localizes to the plasma membrane (134 total cells were analyzed). FIG. 9E is a schematic of Tmem100 GFP knock-in strategy for creation of a Tmem100$^{+/GFP}$ mouse line. The open reading frame (CDS) of Tmem100 was replaced with a targeting construct containing farnesylated enhanced GFP and the ACE promoter-Cre recombinase-Neomycin selection cassette. FIG. 9F shows images of double staining of anti-GFP (green) and anti-Tmem100 (red) antibodies in Tmem100$^{GFP/+}$ mice confirmed GFP is a surrogate marker for Tmem100 in DRG. FIG. 9G shows images of double staining of TRPA1 and IB4 in DRG. The anti-TRPA1 antibody is specific as there is no appreciable level of background signal in DRG from TRPA1 KO mice. Moreover, TRPA1 is not expressed in IB4$^+$ neurons. FIGS. 9H and 9I show that Tmem100 is upregulated in the DRG neurons after inflammation. FIG. 9H is a graph illustrating that the percentage of Tmem100-expressing neurons in L4 DRG was increased in the CFA model at days 1 and 4 compared to L4 DRG neurons on the contralateral side (control). (DRG from 3 mice, **$p<0.01$ at day 1; *$p<0.05$ at day 4.) FIG. 9I shows images of immunofluorescent staining with anti-Tmem100 antibody in the L4 DRG at day 1. All data were analyzed using Student's unpaired t-test. All bars are presented as mean±SEM.

FIGS. 10A-10C demonstrate that TRPA1 and TRPV1 levels are not altered in DRG from Tmem100 CKO mice. FIG. 10A shows images of western blots using anti-TRPV1, -TRPA1, -Tmem100, and -actin antibodies from Avil-Cre;Tmem100$^{+/+}$ and Avil-Cre;Tmem100$^{fl/fl}$ (Tmem100 CKO) mice. FIG. 10B is a graph of pooled results of TRPA1/actin band intensities. (n=8; p=0.79; 108±21 in Avil-Cre;Tmem100$^{+/+}$ and 116±20 in Tmem100 CKO). FIG. 10C is a graph of pooled results of TRPV1/actin band intensities. (n=8; p=0.58; 38±8 in Avil-Cre;Tmem100$^{+/+}$ and 31±9 in Tmem100 CKO). FIGS. 10D-10F demonstrate that developmental and morphological defects were not observed in Tmem100 conditional knockout (Tmem100 CKO) mice. FIG. 10D is a table quantifying immunofluorescent staining of DRG markers in Avil-Cre;Tmem100$^{GFP/fl}$ mice. None of the markers tested showed evidence of cell type-specific defects in mice lacking Tmem100 in their primary sensory neurons. (n>3 for each marker; 8-week-old male). FIG. 10E shows images of double staining of GFP (green) and CGRP (red) in the lumbar spinal cord of adult mice. FIG. 10F shows images of double staining of GFP (green) and IB$_4$ (red) in the lumbar spinal cord of adult mice. FIG. 10G is a graph showing the acute pain phenotype induced by MO is dose-dependent. N=6 for 0.02%, 13 and 11 for Avil-Cre;+/+ and Avil-Cre;fl/fl for 0.2%, and 9 and 6 for Avil-Cre;+/+ and Avil-Cre;fl/fl for 2%. **$p<0.01$. All data were analyzed using Student's unpaired t-test. All bars are presented as mean±SEM. FIG. 10H and FIG. 10I are graphs showing Cold-induced activities are not altered in Tmem100-deficient mice. FIG. 10H is a graph showing the percentage of DRG neurons activated by the temperature cooling from 22.5 to 13.8° C. with bath perfusion is not significantly different from Avil-Cre;Tmem100$^{+/+}$ and Avil-Cre;Tmem100$^{fl/fl}$ groups. (N=19; 16±2 in Avil-Cre;Tmem100$^{+/+}$ and 12±4 in Avil-Cre;Tmem100$^{fl/fl}$; p=0.41). FIG. 10I is a graph showing acute pain evoked by the cold plate of zero degree is not altered in Tmem100-deficient mice. N=7. All data were analyzed using student's T-test. All bars are presented as mean±SEM.

FIGS. 11A-11C show Dose-response of MO in DRG neurons and a heterologous system. FIG. 11A is a graph of calcium imaging of Avil-Cre;Tmem100$^{+/+}$ and Avil-Cre; Tmem100$^{fl/fl}$ DRG neurons with MO of different concentrations. N=3, 6, and 9 for 5, 20, and 70 µM, respectively. ***p<0.001. Student's t-test was applied for analysis. FIG. 1B is a graph quantifying whole-cell recording of DRG neurons with different concentration of MO (N=7, 10, 12, 10, 12 and 9 for 1, 10, 25, 50, 100 and 300 µM). FIG. 11C is a graph quantifying single-channel recording of CHO cells expressing TRPA1 and TRPV1 or TRPA1 only, respectively (N=6, 7, 10, 10, 10, 9 and 9 for 0.1, 1, 10, 25, 50, 100 and 300 µM). FIGS. 11D-11F demonstrate that Tmem100 does not significantly affect TRPA1 and TRPV1 membrane trafficking. FIG. 11D is an image of biotinylation assays of CHO cells expressing myc-TRPA1, TRPV1, and either Tmem100 or Tmem100-3Q mutant. Beta1 integrin and beta-actin were used as positive controls for the biotinylated membrane and cytoplasmic fractions, respectively. FIG. 11E is a graph quantifying the level of biotinylated fraction of TRPA1. The TRPA1/beta1 integrin ratio was calculated and normalized to the ratio from the group transfected with myc-TRPA1 and TRPV1 only (marked as vector). Compared to the vector group, the results did not suggest a significant difference in wild-type (WT) Tmem100-transfected (T100) or Tmem100-3Q mutant-transfected cells (T100-3Q). However, the data suggest a trend towards decreased surface levels of TRPA1 in the presence of Tmem100 and increased surface levels of TRPA1 with Tmem100-3Q mutant co-expression. FIG. 11F is a graph quantifying the level of biotinylated portion of TRPV1. The results were analyzed in the same manner as FIG. 11E. The data suggest that WT Tmem100 and Tmem100-3Q mutant do not alter trafficking of TRPV1 to the surface (n=4 for (FIG. 11E) and (FIG. 11F); one-way ANOVA with Bonferroni post hoc was performed for Figures (FIG. 11E) and (FIG. 11F); NS: non-significant). FIG. 11G-11M demonstrate that TRPA1 activity evoked by MO and CA is also enhanced in the presence of Tmem100 in an alternative expression system: HEK293T cells. FIGS. 11G and 11H are graphs indicating that TRPV1 is required for the enhancing effect of Tmem100 on TRPA1 activity. In TRPA1-V1-expressing HEK293T cells, Tmem100 increased the percentage of cells that respond to 100 nM MO and 5 µM CA. This enhancing effect of Tmem100 was abolished when TRPV1 was replaced with TRPM8, showing no interaction between TRPA1 and TRPM8. The activation of TRPA1 was monitored with calcium imaging. Each group was tested greater than 3 times; *p<0.05; **p<0.01. The statistic is one-way ANOVA with Bonferroni's post-hoc test. All error bars represent SEM. The baseline 340/380 ratios for the cells tested were not drastically different (TRPA1+V1: 1.1±0.03; TRPA1+V1+Tmem100: 1.1±0.04; TRPA1+TRPM8+Tmem100: 0.95±0.04). FIG. 11I is a graph quantifying single-channel recording of CHO cells expressing TRPA1+TRPV1 with or without Tmem100 at a ratio of 1:1:1. Numbers of responsive cells are marked within bars. FIG. 11J is a graph indicating that Tmem100 increases the potency of TRPA1 activity in cells expressing both TRPA1 and TRPV1. In a heterologous system, Tmem100 lowered the EC$_{50}$ of CA (EC$_{50}$=21 µM in A1+V1+Tmem100 and 57 µM in A1+V1; each concentration was tested more than 3 times). *p<0.05. FIG. 11K is a graph quantifying single-channel recording of the CHO cells expressing TRPA1+TRPV1 with or without Tmem100 under different concentration of MO. N=5-8/trial. **p<0.01. FIGS. 11K and 11M are graphs quantifying calcium imaging in HEK293T cells expressing TRPA1 and TRPV1. The percentage of cells that respond to 100 nM MO and 10 µM CA was significantly lower in the Tmem100-3Q-transfected group compared with the group lacking Tmem100-3Q (repeated 3 times; *p<0.05, **p<0.01). The statistic is one-way ANOVA with Bonferroni's post-hoc test; *p<0.05, **p<0.01. All error bars represent SEM.

FIGS. 12A-12D demonstrates context-dependent regulation of Tmem100 in the TRPA1-V1 complex. FIGS. 12A and 12B are graphs quantifying MO (10 µM)—(FIG. 12A) and CAP (100 nM)-induced (FIG. 12B) single-channel activity (NP$_o$) at Vh=−60 mV in CHO cells expressing TRPA1 vs. TRPA1+Tmem100 (1:4 molar ratio) and TRPA1+TRPV1 (1:1) vs. TRPA1+TRPV1+Tmem100 (1:1:4). NP$_o$ measurements accounted for all recorded conductance, including main and sub-conductance. The configuration is cell-attached patch, and the number of patches that responded among those analyzed is indicated within bars. NP$_o$: MO 0.6±0.11 for TRPA1+TRPV1 vs. 1.05±0.14 for TRPA1+TRPV1+Tmem100 CHO cells; 1.15±0.15 for TRPA1 vs. 0.64±0.18 for TRPA1+Tmem100 CHO cells. CAP-0.81±0.12 for TRPA1+TRPV1 vs. 0.82±0.14 for TRPA1+TRPV1+Tmem100 CHO cells; 0.81±0.07 for TRPV1 vs. 0.45±0.1 for TRPV1+Tmem100 cells. The statistic is unpaired t-test and one-way ANOVA with Bonferroni's post-hoc test (*p<0.05; ***p<0.001). All error bars represent SEM. FIGS. 12C and 12D show representative single-channel recording during 5 sec at Vh=−60 mV for MO-gated current (FIG. 12C) and 4 sec for CAP-gated current (FIG. 12D) in TRPA1- and TRPA1+Tmem100-expressing CHO cells. Traces are 4 sec long, and the proteins expressed are indicated below the traces. Vertical bars to the right of the traces represent 4 pA; c is the closed state; o1, o2, and o3 show open states for 3 independent channels in the patch. FIGS. 12E-12J show characterization of single channel current-voltage relationships in the presence and absence of Tmem100 and Tmem100-3Q mutant. FIGS. 12E, 12G and 12I are graphs of mustard oil (MO; 10 µM)-gated single channel current-voltage relationship (I-V) in CHO cells expressing TRPA1, TRPA1+Tmem100 (1:4 molar ratio), TRPA1+TRPV1 (1:1), or TRPA1+TRPV1+Tmem100 (1:1:4) (FIG. 12E); TRPA1 and TRPA1+Tmem100-3Q (1:4) (FIG. 12G); TRPA1+TRPV1 (1:1) and TRPA1+TRPV1+Tmem100-3Q (1:1:4) (FIG. 12I). Configuration is cell-attached patch. TRPA1 and TRPV1 co-expression in the patches was confirm by responses to both MO and CAP. I-V is presented for main single-channel conductance. Number of cells recorded: n=5-8. FIGS. 12F, 12J and 12J are graphs of CAP (100 nM)-gated single channel I-V relationship in CHO cells expressing TRPV1, TRPV1+Tmem100 (1:4), TRPA1+TRPV1 (1:1) and TRPA1+TRPV1+Tmem100 (1:1:4) (FIG. 12F); TRPV1 and TRPV1+Tmem100-3Q (1:4) (FIG. 12H); TRPA1+TRPV1 (1:1), or TRPA1+TRPV1+Tmem100-3Q (1:1:4) (FIG. 12J). The configuration is cell-attached patch. CHO cells co-expressing TRPA1 and TRPV1 responded to both CAP and MO. I-V is presented for main single-channel conductance. Number of cells recorded: n=5-7.

FIG. 12K is a graph quantifying whole cell recording of capsaicin (100 nM)-evoked currents in MO (50 µM)-unresponsive (MO−) and -responsive (MO+) DRG neurons from Avil-Cre;Tmem100$^{+/+}$ and Avil-Cre;Tmem100$^{fl/fl}$ mice. The numbers in the boxes represent the numbers of capsaicin responsive neurons tested. All bars are presented as mean±SEM.

FIG. 13A is a graphic quantification of GST pull-down for the C-terminus and TRPV1. Increased association between TRPV1 and the C terminus in Tmem100-3Q was observed. N=4, **p<0.01. FIG. 13B is an image of GST pull-down of TRPV1 with different fragments of Tmem100 tagged with GST. TRPV1 pull-down is enhanced in the GST-C-3Q group compared to the GST-C-WT group. FIG. 13C is a graph of FRET-TIRF measurements of the interaction among TRPV1 and Tmem100 (T100). The interaction between Tmem100 and TRPV1 is not altered by the addition of TRPA1. FIG. 13D is a graph of FRET-TIRF measurements of the interaction among TRPA1 and Tmem100 (T100). The interaction between TRPA1 and Tmem100 is significantly increased with the presence of TRPV1. Similar to the experiments in FIG. 5A-5F, the Rho-pYC was used as a positive control for maximal effects of the system, and M-V1 was a negative control. *p<0.05, p<0.01, *p<0.001. All bars are presented as mean±SEM.

FIG. 14A-FIG. 14D are related to FIG. 6A-6G and demonstrate the context-dependent regulation of Tmem100-3Q in the TRPA1-V1 complex. FIGS. 14A and 14B are graphs of MO (10 μM)-(FIG. 14A) and CAP (100 nM)-induced (FIG. 14B) single-channel activity ($NP_o$) at Vh=−60 mV in CHO cells expressing TRPA1 vs. TRPA1+Tmem100-3Q (T100-3Q) (1:4 molar ratio) and TRPA1+TRPV1 (1:1) vs. TRPA1+TRPV1+Tmem100-3Q (1:1:4). $NP_o$: MO 0.55±0.09 for TRPA1+TRPV1 vs. 0.16±0.06 for TRPA1+TRPV1+Tmem100-3Q CHO cells; 0.98±0.18 for TRPA1 vs. 1.05±0.14 for TRPA1+Tmem100-3Q cells. CAP 1.04±0.23 for TRPA1+TRPV1 vs. 1.08±0.17 for TRPA1+TRPV1+Tmem100-3Q cells; 1.3±0.16 for TRPV1 vs. 0.73±0.12 for TRPV1+Tmem100-3Q cells. The statistic is unpaired t-test and one-way ANOVA with Bonferroni's post-hoc test (*p<0.05; **p<0.01; NS: no significant difference). All error bars represent SEM.

FIG. 15A is a graph of calcium imaging data from HEK293 cells expressing TRPA1 and TRPV1. Among the three shortened CPP (sequences on top), only F2 (2 μM) significantly reduced the percentage of cells responsive to CA (10 μM) compared to the scrambled (repeated 3 times). In FIG. 15A: top sequence (Tmem100): SEQ ID NO: 8; F1: SEQ ID NO: 16; F2: SEQ ID NO: 17; and F3: SEQ ID NO: 18. *p<0.05. As shown in FIG. 15B, F2 (SEQ ID NO: 17) (5 μl 100 μM; intradermal injection) is also effective in suppressing paclitaxel-induced mechanical hyperalgesia. N=5, ***p<0.01. FIGS. 15C and 15D are graphs showing open box: scrambled; black box: F2. Intrathecal injection of human T100-3Q peptide (h-T100) and HC-030031 dose-dependently inhibits neuropathic mechanical hypersensitivity in rats. FIG. 15C shows graphs quantifying that in rats with spinal nerve ligation (SNL), intrathecal injection of h-T100 (10-100 μM, 10 μl, n=7-8/dose) dose-dependently increased ipsilateral paw withdrawal thresholds (PWT) from pre-drug levels, reflecting attenuated mechanical hypersensitivity. Intrathecal injections of scrambled peptide (100 μM, 10 μl, n=6) and vehicle (n=5) had no effect. There was no significant change in the contralateral PWT after drug injection. FIG. 15D is a graph quantifying the intrathecal injection of HC-030031 (10-200 μM, 10 μl, n=6/dose), a selective TRPA1 receptor antagonist, also increased ipsilateral PWTs of SNL rats in a dose-dependent fashion. Intrathecal injection of vehicle (n=6) was not effective. Contralateral PWTs did not change significantly after drug treatment. T100-Mut peptide has a lower $EC_{50}$ for inhibiting pain (29.3 μM, 10 μl) than HC030031 (58.2 μM, 10 ill). *P<0.05, versus pre-drug. One-way repeated measures ANOVA. All bars are presented as mean±SEM.

FIG. 16A is a graph showing that in rats with spinal nerve ligation (SNL), intrathecal injection of P2-Mut (50 μM, 10 μl, n=10) increased the time that rats spent in their drug-paired chamber, with a corresponding decrease in the scramble peptide-paired chamber. The difference score (difference score="Post-conditioning time"−"Pre-conditioning time") in the P2-Mut-paired chamber was significantly greater than that in scramble-paired chambers, reflecting attenuated ongoing neuropathic pain. However, P2-Mut did not induce chamber preference in sham-operated rats (n=8). This result suggests that the drug is not rewarding in the absence of nerve injury, and the preference to the P2-Mut-paired chamber in SNL rats result from drug-induced pain relief. FIG. 16B is a graph showing that, in a separate experiment, systemic administration of gabapentin (60 mg/kg, i.p.) significantly increased the time the SNL rats spent in the gabapentin-paired chamber (n=8), with a corresponding decrease in the saline-paired chamber. However, gabapentin did not induce chamber preference in sham-operated rats (n=8). The difference scores were significantly different between gabapentin-paired and saline-paired chambers in SNL rats, but not in sham-operated rats. *p<0.05 by paired t-test.

DETAILED DESCRIPTION OF THE INVENTION

Figure 1:
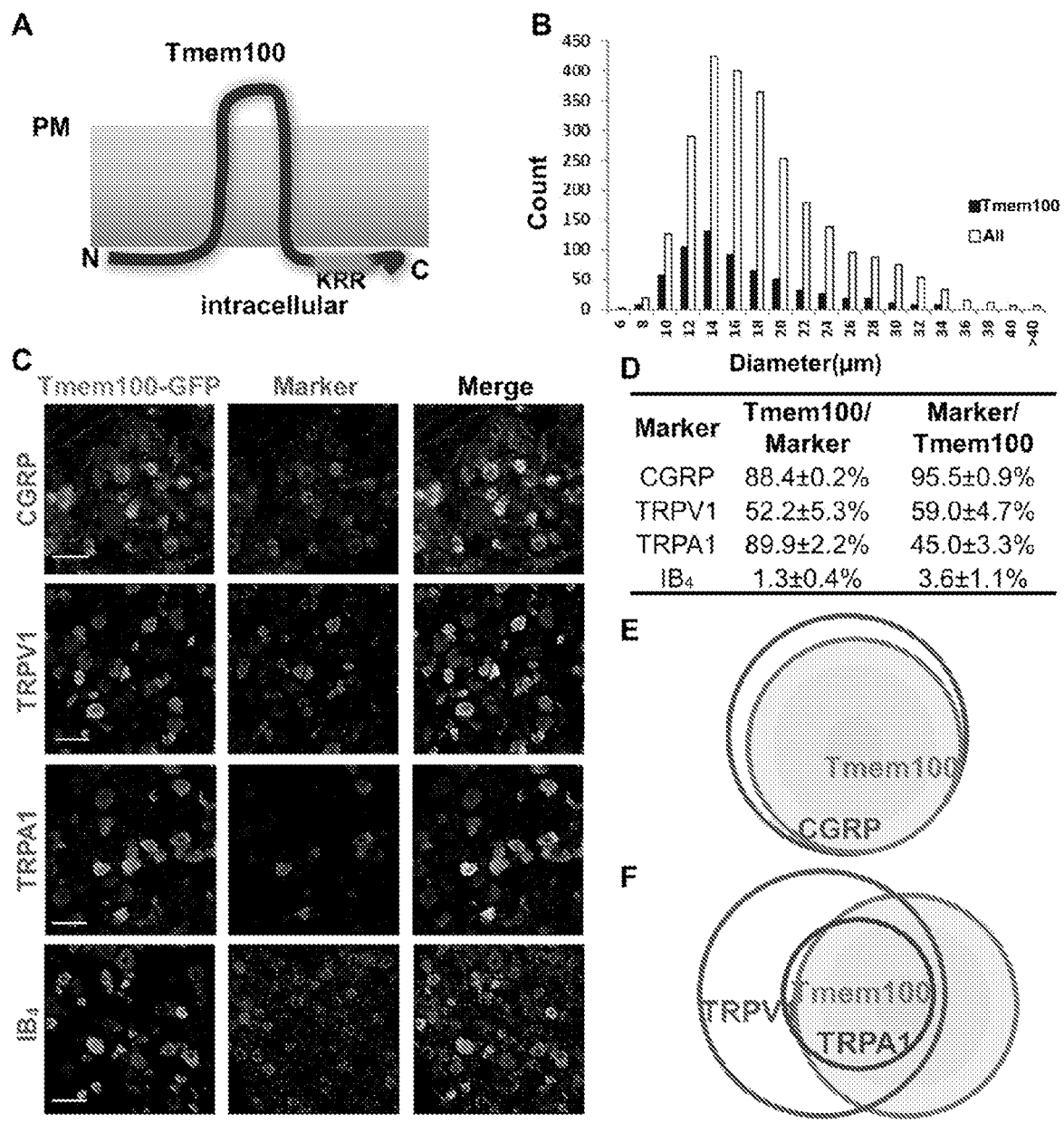
FIG. 1A-FIG. 1F demonstrate that Tmem100 is expressed in TRPA1/TRPV1 positive peptidergic DRG neurons.

TRPA1 and TRPV1 are crucial mediators of pain and have been shown to form Complexes. The present invention is based, at least in part, on the identification of Tmem100 peptides and mutants or derivatives thereof, as a potentiating modulator of TRPA1-V1 complexes.

Pain is the cardinal symptom of many debilitating diseases, causing heavy societal and health burdens worldwide. It is known that ion channels and receptors in the dorsal root ganglia (DRG) are responsible for the detection of noxious stimuli, and their plasticity contributes to the increased severity of pain (Woolf and Costigan, 1999). TRP (Transient Receptor Potential) channels are emerging targets for understanding this process and developing treatments (Venkatachalam and Montell, 2007). Their ability to form multimeric complexes (Goel et al., 2002; Hellwig et al., 2005; Hofmann et al., 2002; Schaefer, 2005; Strubing et al., 2001; Xu et al., 1997) broadens the variety and complexity of channel regulation and the potential implications for pain modulation (Jeske et al., 2011; Liu et al., 2011; Patil et al., 2011; Schmidt et al., 2009). Among TRP channels, TRPA1 and TRPV1 are essential and widely studied molecular sensors and mediators of pain signals in DRG neurons (Bautista et al., 2006; Caterina et al., 2000; Caterina et al., 1997). It is well documented that most if not all TRPA1$^+$ DRG neurons co-express TRPV1 (Bautista et al., 2006; Story et al., 2003). Although recent studies have suggested that TRPA1 and TRPV1 can form a complex in a heterologous expression system as well as sensory neurons (Fischer et al., 2014; McMahon and Wood, 2006; Salas et al., 2009; Staruschenko et al., 2010), the functional significance and modulation of the complex in the nociceptive pathway are unclear.

Tmem100 (also known as Pirt2) was identified as a candidate for the modulation of the TRPA1-V1 complex in the nociceptive pathway. Tmem100 is a 134-amino acid, two-transmembrane protein highly conserved in vertebrates (Moon et al., 2010). It is found in other organs besides the DRG, expressed in blood vessels, ventral neural tubes, and the notochord (Moon et al., 2010). Tmem100 has been shown to be involved in processes such as renal development (Georgas et al., 2009), vasculogenesis (Moon et al., 2010), and lung cancer cell invasiveness (Frullanti et al., 2012). However, prior to the invention described herein, little was known about the underlying mechanisms of these effects and the role of Tmem100 in the nervous system.

Data described herein demonstrate that Tmem100 enhances TRPA1 activity in vitro and in vivo. Interestingly, this regulation depends on the presence of TRPV1. In the DRG, Tmem100 is co-expressed with TRPA1 and TRPV1. It forms a complex with TRPA1 and TRPV1 in both DRG neurons and heterologous systems. Tmem100 selectively augments TRPA1-associated activity by increasing the open probability of the channel when TRPA1 and TRPV1 are both present in membrane patches. Tmem100 mutant mice exhibit a reduction in inflammatory mechanical hyperalgesia and TRPA1- but not TRPV1-mediated pain. Mechanistically, Tmem100 weakens the association of TRPA1 and TRPV1, thereby releasing the inhibition of TRPA1 by TRPV1 (Salas et al., 2009). A Tmem100 mutant, Tmem100-3Q, exerts the opposite effect, i.e., it enhances the association of TRPA1 and TRPV1 and strongly inhibits TRPA1. Taking advantage of this inhibition, a new strategy was developed and described herein for blocking persistent pain. A cell-permeable peptide that mimics the C-terminus of Tmem100-3Q and selectively inhibits TRPA1-mediated activity and pain in a TRPV1-dependent manner is described herein.

TRP channels have been classified into at least six groups: TRPC (short), TRPV (vanilloid), TRPM (long, melastatin), TRPP (polycystins), TRPML (mucolipins), and TRPA (ANKTM1). The TRPC group can be divided into 4 subfamilies (TRPC1, TRPC4,5, TRPC3,6,7 and TRPC2) based on sequence homology and functional similarities. Currently the TRPV family has 6 members. TRP V5 and TRP V6 are more closely related to each other than to TRPV1, TRP V2, TRPV3, or TRPV4. TRPA1 is most closely related to TRPV3, and is more closely related to TRPV1 and TRPV2 than to TRPV5 and TRPV6. The TRPM family has 8 members. Constituents include the following: the founding member TRPM1 (Melastatin or LTRPC1), TRPM3 (KIAA1 616 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMR1), TRPM5 (Mtr1 or LTRPC5), and TRPM4 (FLJ20041 or LTRPC4). The sole mammalian member of the TRPA family is ANKTM1. The TRPML family consists of the mucolipins, which include TRPML1 (mucolipins 1), TRPML2 (mucolipins 2), and TRPML3 (mucolipin3). The TRPP family consists of two groups of channels: those predicted to have six transmembrane domains and those that have 11. TRPP2 (PKD2), TRPP3 (PKD2L1), TRPP5 (PKD2L2) are all predicted to have six transmembrane domains. TRPP1 (PKD13 PC05 PKD-REJ and PKD-IL1 are all thought to have 11 transmembrane domains.

The TRP channels constitute a large and important class of channels involved in modulating cellular homeostasis. The present invention provides methods and agents that modulate at least one TRP family member. Specifically, the present invention provides methods and agents for antagonizing a function of TRPA1. Modulating a function of TRPA1 provides a means for modulating calcium homeostasis, sodium homeostasis, intracellular calcium levels, membrane polarization (resting membrane potential), and/or cation levels in a cell. Agents that can modulate one or more TRPA1 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or misregulation of TRPA1 expression or function.

The present application provides agents that can modulate TRPA1 function as well as methods employing said agents.

Preferably, the Tmem 100 mutant polypeptides described herein comprise a lipid modification, e.g., palmitoyl (Pal) or myristyl (Myr) groups, at their N-terminus to make them cell permeable.

Palmitoylation is the covalent attachment of fatty acids, such as palmitic acid, to cysteine, serine, or threonine residues of proteins, which are typically membrane proteins. Palmitoylation enhances the hydrophobicity of proteins and contributes to their membrane association. Palmitoylation also plays a significant role in subcellular trafficking of proteins between membrane compartments, as well as in modulating protein-protein interactions. In contrast to prenylation and myristoylation, palmitoylation is usually reversible (because the bond between palmitic acid and protein is often a thioester bond). The reverse reaction is catalysed by palmitoyl protein thioesterases. Because palmitoylation is a dynamic, post-translational process, it is employed by the cell to alter the subcellular localization, protein-protein interactions, or binding capacities of a protein.

Myristoylation is an irreversible, protein lipidation modification where a myristoyl group, derived from myristic acid, is covalently attached by an amide bond to the alpha-amino group of an N-terminal glycine residue. Myristic acid is a 14-carbon saturated fatty acid (14:0) with the systematic name of n-Tetradecanoic acid. This modification can be added either co-translationally or post-translationally.

N-myristoyltransferase (NMT) catalyzes the myristic acid addition reaction in the cytoplasm of cells. This lipidation event is common among many organisms including animals, plants, fungi, protozoans and viruses. Myristoylation allows for weak protein-protein and protein-lipid interactions and plays an essential role in membrane targeting, protein-protein interactions and functions widely in a variety of signal transduction pathways.

Compositions or Agents

In one aspect, the present invention provides compositions or agents and pharmaceutical compositions comprising, consisting of, or consisting essentially of particular TRPA1 inhibitory polypeptides and nucleic acids.

As used herein, the term "isolated" when used to refer to nucleic acid and polypeptide compositions refers to nucleic acids or polypeptides existing in a state other than the state in which they exist in nature. In other words, the term is used to denote some level of separation from other proteins and cellular components with which the protein is endogenously found. Isolated, when used in this context, does not necessarily mean that the protein or nucleic acid is provided in a purified form. Additionally, the term "isolated" is not intended to imply that the polypeptide or nucleic acid is isolated from an organism. Rather, the term also includes recombinantly produced nucleic acids and polypeptides.

The present invention also encompasses isolated polynucleotides that encode a polypeptide comprising Tmem100 peptide or fragment thereof or Tmem100 mutant peptide or fragment thereof. The present invention also encompasses he isolated polypeptides.

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The invention provides an isolated polypeptide comprising, consisting of, or consisting essentially of the amino acid sequence represented in SEQ ID NO: 5 or SEQ ID NO: 6, or fragments thereof.

The invention provides an isolated polypeptide comprising, consisting of, or consisting essentially of the amino acid sequence represented in SEQ ID NO: 7 or SEQ ID NO: 8, or fragments thereof.

The invention provides an isolated polypeptide encoded by a nucleic acid sequence comprising, consisting of, or consisting essentially of SEQ ID NO: 9 or SEQ ID NO: 10.

The invention provides an isolated polypeptide encoded by a nucleic acid sequence comprising, consisting of, or consisting essentially of a nucleotide sequence represented in SEQ ID NO: 11 or SEQ ID NO: 12.

The present invention further relates to variants of the polynucleotides, for example, fragments, analogs, and derivatives. The variant of the polynucleotide can be a naturally occurring allelic variant of the polynucleotide or a non-naturally occurring variant of the polynucleotide. The polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

The polynucleotides can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

The polynucleotides can comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

The present invention provides isolated nucleic acid molecules having a nucleotide sequence at least 80% identical, at least 85% identical, at least 90% identical, at least 95% identical, or at least 96%, 97%, 98% or 99% identical to a polynucleotide comprising, consisting of, or consisting essentially of the amino acid sequence represented in SEQ ID NO: 1 or SEQ ID NO: 3, or fragments thereof.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some examples, the polynucleotide variants contain alterations which produce silent substitutions, additions, or deletions, but do not alter the properties or activities of the encoded polypeptide. In some examples, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity is be measured using sequence comparison software or algorithms or by visual inspection. Various algorithms and software are known in the art that is used to obtain alignments of amino acid or nucleotide sequences. One such non-limiting example of a sequence alignment algorithm is the algorithm described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). Gapped BLAST is used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. The percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). The GAP program in the GCG software package, which incorporates the algorithm of Needleman and Wunsch (*J. Mol. Biol.* (48):444-453 (1970)) is used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). The percent identity between nucleotide or amino acid sequences is determined using the algorithm of Myers and Miller (CABIOS, 4:11-17 (1989)). For example, the percent identity is determined using the ALIGN program (version 2.0) and using a PAM120 with residue table, a gap length penalty of 12 and a gap penalty of 4. Appropriate parameters for maximal alignment by particular alignment software can be determined by one skilled in the art. In some examples, the default parameters of the alignment software are used. In some examples, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some examples, at least 95%, 96%, 97%, 98%, or 99% identical) to a reference sequence can, in certain examples, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In an example, two nucleic acids or polypeptides of the invention are substantially identical, meaning they have at least 70%, at least 75%, at least 80%, at least 85%, at least 90%, and in some examples at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 5, at least about 10, about 20, about 40-60 residues in length or any integral value therebetween, or over a longer region than 60-80 residues, at least about 90-100 residues, or the sequences are substantially identical over the full length of the sequences being compared.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

The polypeptides of the present invention can be recombinant polypeptides, natural polypeptides, or synthetic polypeptides. It will be recognized in the art that some amino acid sequences of the invention can be varied without significant effect of the structure or function of the protein.

Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some examples, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci. USA* 81:5662-5066 (1984) and U.S. Pat. No. 4,588,585.

A DNA sequence encoding a polypeptide of interest could be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

The invention provides an expression vector, which replicates in at least one of a prokaryotic cell and eukaryotic cell. The expression vector comprises any of the foregoing TRPA1 inhibitory nucleic acids. Similarly provided are cells comprising these expression vectors, which cells express the TRPA1 inhibitory protein encoded by the expressed nucleic acid.

Additionally provided are methods of producing a polypeptide. The method includes culturing one of the foregoing cells (e.g., a cell expressing a TRPA1 inhibitory polypeptide) in a suitable cell culture medium to express said polypeptide. As noted above, the invention contemplates an expression vector which comprises a coding sequence for a TRPA1 inhibitory protein, as provided herein. A "vector" is a replicon, such as plasmid, phage or cosmid, to which another DNA segment is attached. The term "vector" refers to a nucleic acid molecule capable of transporting another nucleic acid to which it has been linked. One type of vector is an episome which is a nucleic acid capable of extra-chromosomal replication. Vectors capable of autonomous replication and/or expression of nucleic acids to which they are linked is also used. Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form are not bound to the chromosome. However, the invention is intended to include such other, forms of expression vectors which serve equivalent functions and which become known in the art subsequently hereto.

A DNA or nucleic acid "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence of the present invention can include, but is not limited to, cDNA from eukaryotic mRNA, genomic DNA sequences from eukaryotic (e.g., mammalian) DNA, and synthetic DNA sequences. A polyadenylation signal and transcription termination sequence is located 3' of the coding sequence.

Nucleic acid or DNA regulatory sequences or regulatory elements are transcriptional and translational control sequences, such as promoters, enhancers, polyadenylation signals, and terminators, that provide for and/or regulate expression of a coding sequence in a host cell. Regulatory sequences for directing expression of eukaryotic ion channels and detectable markers of certain examples are art-recognized and is selected by a number of well understood criteria. Examples of regulatory sequences are described in Goeddel, Gene Expression Technology: Methods in Enzymology (Academic Press, San Diego, Calif. (1990)). For instance, any of a wide variety of expression control sequences that control the expression of a DNA sequence when operatively linked to it is used in these vectors to express DNA sequences encoding the ion channels and detectable markers. Such useful expression control sequences, include, for example, the early and late promoters of SV40, beta2 tubulin, adenovirus or cytomegalovirus immediate early promoter, the lac system, the trp system, the TAC or TRC system, T7 promoter whose expression is directed by T7 RNA polymerase, the promoter for 3-phosphoglycerate kinase or other glycolytic enzymes, the promoters of acid phosphatase, e.g., Pho5$_5$ and the promoters of the yeast α-mating factors and other sequences known to control the expression of genes of prokaryotic or eukaryotic cells or their viruses, and various combinations thereof. It should be understood that the design of the expression vector depends on such factors as the choice of the host cell to be transformed. Moreover, the vector's copy number, the ability to control that copy number and the expression of any other protein encoded by the vector, such as antibiotic markers, should also be considered.

The invention contemplates the use of any promoter that can drive the expression of a TRPA1 inhibitory protein in prokaryotic or eukaryotic cells. As used herein, the term "promoter" means a DNA sequence that regulates expression of a selected DNA sequence operably linked to the promoter, and which effects expression of the selected DNA sequence in cells. A "promoter" generally is a DNA regulatory element capable of binding RNA polymerase in a cell and initiating transcription of a coding sequence. For example, the promoter sequence is bounded at its 3' terminus by the transcription initiation site and extend upstream (5' direction) to include the minimum number of bases or elements necessary to initiate transcription at levels detectable above background. Within the promoter sequence is found a transcription initiation site, as well as protein-binding domains responsible for the binding of RNA polymerase. Eukaryotic promoters will often, but not always, contain "TATA" boxes and "CAAT" boxes. Various promoters, including inducible promoters, is used to drive the various vectors of the present invention. The term "promoter" also encompasses prokaryotic and/or eukaryotic promoters and promoter elements. The term "promoter" as used herein encompasses "cell specific" promoters, i.e., promoters, which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that, are inducible (i.e., expression levels can be controlled).

Cells expressing an expression vector are assayed to confirm expression of TRPA1 inhibitory protein. For example, protein expression is confirmed • using Western blot analysis, immunocytochemistry, or immunohistochemistry. Additionally or alternatively, TRPA1 function can be assessed using, for example, calcium imaging analysis to evaluate ion flux or electrophysiological methods (e.g., patch clamp analysis) to evaluate current.

Methods

The present invention provides, generally, methods for treating pain or itch.

In certain aspects, the invention features methods for treating or preventing a condition associated with TRPA1 function or for which reduced TRPA1 activity can reduce the severity, comprising administering an effective amount of a Tmem100 mutant polypeptide, or fragment thereof.

The present invention also provides methods of preventing, treating, or alleviating symptoms of a disease or condition associated with TRPA1 function or for which reduced TRPA1 activity can reduce the severity, comprising administering to a subject in need thereof a Tmem100 mutant polypeptide, or fragment thereof.

The present invention also provides methods of inhibiting TRPA1 function in a cell, comprising administering to the cell an effective amount of a Tmem100 mutant polypeptide, or fragment thereof, thereby inhibiting TRPA1 function in the cell.

In certain embodiment, the TRPA1 function is an association with TRPV1. Preferably, the Tmem100 mutant polypeptide, or fragment thereof, enhances the association of TRPA1 with TRPV1.

The TRPA1 function is an inward TRPA1-mediated current, an outward TRPA1-mediated current or TRPA1-mediated ion flux.

As discussed herein, the Tmem100 mutant polypeptide comprises SEQ ID NO: 1, or fragments thereof or SEQ ID NO: 3, or fragments thereof.

In other examples of the methods, the Tmem100 mutant polypeptide, or fragment thereof, is provided to a cell and the cell is a sensory neuron. The sensory neuron preferably resides in the dorsal root ganglia (DRG).

Any of the methods described herein are used to prevent, treat, or alleviate symptoms of pain or to prevent, treat, or alleviate symptoms of itch.

The Tmem100 mutant polypeptide, or fragment thereof are administered alone or in combination with one or more agents, as described in more detail below. The Tmem100 mutant polypeptide, or fragment thereof, is administered in combination with one or more of a TRPV1 inhibitor, a TRPV3 inhibitor, a TRPV4 inhibitor, or a TRPM8 inhibitor.

In addition to TRPV family members, other TRP channels have been implicated in pain reception and/or sensation. For example, certain TRPM channels including TRPM8 have been implicated in the reception and/or sensation of pain. Accordingly, in certain examples the methods of the present invention include treating pain by administering (i) a combination of a TRPA1 inhibitor as described herein and a TRPM8 inhibitor; (ii) a combination of a TRPA1 inhibitor, a TRPM8 inhibitor, and one or more of a selective TRPV1 and/or TRPV3 inhibitor; (iii) a cross-TRP inhibitor that inhibits a function of TRPA1 and TRPM8; or (iv) a pan inhibitor that inhibits a function of TRPA1, TRPM8, and one or more of TRPV1 and TRPV3.

Diseases and Disorders

The invention provides methods and compositions for inhibiting a function of a TRPA1 channel in vitro or in vivo. Exemplary functions include, but are not limited to, TRPA1-mediated current. The invention provides methods and compositions for inhibiting TRPA1-mediated neuronal hyperexcitability. The invention provides methods for preventing or treating a disease or disorder or condition by administering a composition that modulates the level and/or activity of a TRPA1 protein. The composition selectively inhibits the expression level and/or activity of a TRPA1 protein. In other words, in certain embodiment, the composition inhibits the activity of a TRPA1 protein preferentially in comparison to the activity of one or more other ion channels.

In particular examples of the methods for preventing or treating diseases and disorders provided herein, the disease or disorder can be, for example, a pain or sensitivity to touch. For example, the pain is related to a disease or disorder, e.g., cancer pain, a dermatological disease or disorder, a neurodegenerative disease or disorder, (e.g., Alzheimer's disease (AD), Parkinson's disease, Huntingdon's disease, amyotrophic lateral sclerosis (ALS)), and other brain disorders caused by trauma or other insults including aging, an inflammatory disease (e.g., asthma, chronic obstructive pulmonary disease, rheumatoid arthritis, osteoarthritis, inflammatory bowel disease, glomerulonephritis, neuroinflammatory diseases, multiple sclerosis, and disorders of the immune system), cancer (e.g. liposarcoma) or other proliferative disease, kidney disease and liver disease, a metabolic disorder such as diabetes. Further diseases and conditions include post-surgical pain, post herpetic neuralgia, incontinence, and shingles.

Compositions and methods provided herein are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer, in addition to skin cancers described above. Intracellular calcium level plays an important role in cell proliferation in cancer cells (Weiss et al. (2001) International Journal of Cancer 92 (6):877-882).

In addition, pain associated with cancer or with cancer treatment is a significant cause of chronic pain. Cancers of the bone, for example, osteosarcoma, are considered exceptionally painful, and patients with advanced bone cancer requires sedation to tolerate the intense and persistent pain. Accordingly, TRPA1 antagonists of the invention represent a significant possible therapeutic for the treatment of pain, for example, the pain associated with cancer or with cancer treatment.

Given that TRPA1 is differentially expressed in transformed cells, TRPA1 blockers also affect the proliferation of transformed cells and thus be a useful way to slow the disease (see Jaquemar et al. (1999) JBC 274(11): 7325-33). Thus TRPA1 antagonists could alleviate both the cause and symptoms of cancer pain.

Cancer treatments are not only painful, but they can even be toxic to healthy tissue. Some chemotherapeutic agents can cause painful neuropathy. Accordingly, TRPA1 antagonists of the invention represent a significant possible therapeutic for the treatment of the pain and/or inflammation associated with cancer treatments that cause neuropathy.

In other particular examples of the methods for preventing or treating diseases and disorders provided herein, the disease or disorder can be an itch. Many dermatological disorders are accompanied by itch (pruritus). Pruritus and pain share many mechanistic similarities. Both are associated with activation of C-fibers, both are potentiated by increases in temperature and inflammatory mediators and both can be quelled with opiates. Decreasing neuronal excitability, particularly C-fiber excitability alleviates pruritus associated with dialysis, dermatitis, pregnancy, poison ivy, allergy, dry skin, chemotherapy and eczema in some examples.

Compositions and methods provided herein are also used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune' system.

The compositions that inhibit TRPA1 described herein can be used in the treatment of any of the foregoing or following diseases or conditions, including in the treatment of pain associated with any of the foregoing or following diseases or conditions. When used in a method of treatment, an inhibitor can be selected and formulated based on the intended route of administration. Inhibitors can be used to treat the underlying disease or condition, or to relieve a symptom of the disease or condition. Exemplary symptoms include pain associated with a disease or condition, e.g. sensitivity to pain and touch, or pain-related diseases or disorders. Compositions and methods provided herein are used in connection with prevention or treatment of pain or sensitivity to pain and touch. Pain or sensitivity to pain and touch are indicated in a variety of diseases, disorders or conditions, including, but not limited to, diabetic neuropathy, breast pain, psoriasis, eczema, dermatitis, burn, postherpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temporomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

The compositions and methods of the invention are used in the treatment of chronic, as well as acute pain. In some examples, chronic or acute pain is the result of injury, age, or disease.

Pain can be generally categorized as chronic pain and acute pain. The two categories of pain differ in duration, as well as underlying mechanism. Chronic pain is not only persistent, but also does not generally respond well to treatment with currently available analgesics, non-steroidal anti-inflammatory drugs, and opioids.

Two broad sub-categories of chronic pain are neuropathic pain and cancer pain. Wang and Wang (2003) Advanced Drug Delivery Reviews 55: 949-965. Neuropathic pain refers to pain resulting from damage (e.g., from disease, injury, age) to the nervous system (e.g., nerves, spinal cord, CNS, PNS). In some examples, cancer-related pain is caused by tumor infiltration, nerve compression, substances secreted by tumors, or the particular treatment regimen (e.g., radiation, chemotherapeutics, surgery).

Pain is also often classified mechanistically as nociceptive, inflammatory, or neuropathic. Nociceptive pain is pain experienced following, for example, changes or extremes in temperature, exposure to acids, exposure to chemical agents, exposure to force, and exposure to pressure. Reception of painful stimuli sends impulses to the dorsal root ganglia. The response is typically a combination of a reflexive response (e.g., withdrawal from the stimuli) and an emotional reaction. Inflammation is the immune system's response to injury or disease. In response to injury or disease, macrophages, mast cells, neutrophils, and other cells of the immune system are recruited. This infiltration of cells, along with the release of cytokines and other factors (e.g., histamine, serotonin, bradykinin, prostaglandins, ATP, H+, nerve growth factor, TNFα, endothelins, interleukins), can cause fever, swelling, and pain. Current treatments for the pain of inflammation include Cox2 inhibitors and opioids. Neuropathic pain refers to pain resulting from damage (e.g., from disease, injury, age) to the nervous system—(e.g., nerves, spinal cord, CNS, PNS). Current treatment for neuropathic pain includes tricyclic antidepressants, anticonvulsants, Na+ channel blockers, NMDA receptor antagonists, and opioids. There are numerous animal models for studying pain. The various models use various-agents or procedures to simulate pain resulting from injuries, diseases, or other conditions. Blackburn-Munro (2004) Trends in Pharmacological Sciences 25: 299-305 (see, for example, Table 1). Behavioral characteristics of challenged animals can then be observed. Compounds or procedures that reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. To assess spontaneous pain, posture, gait, nocifensive signs (e.g., paw licking, excessive grooming, excessive exploratory behavior, guarding of the injured body part, and self-mutilation) can be observed. To measure evoked pain, behavioral-responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med. 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and Freund's complete adjuvant (CFA) induced hyperalgesia are models of inflammatory pain. Walker et al. (2003) Journal of Pharmacol Exp Ther 304: 56-62; McGaraughty et al. (2003) Br J Pharmacol 140: 1381-1388; Honore et al. (2005) J Pharmacol Exp Ther. Compositions that inhibit TRPA1 can be administered to carrageenan or CFA challenged animals to assess whether they diminish thermal hyperalgesia in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

The Bennett model uses prolonged ischemia of the paw to mirror chronic pain. Xanthos et al. (2004) J Pain 5: Sl. This provides an animal model for chronic pain including postoperative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compositions that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by-hemisecting the spinal cord. Wang and Wang (2003).

Additional models of neuropathic pain include peripheral nerve injury models. The term peripheral neuropathy encompasses a variety of diseases, conditions, and injuries. One of skill in the art can readily select an appropriate model in light of the particular condition or disease under investigation. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy. Wang and Wang (2003).

Cancer pain has any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. Wang and Wang (2003). An exemplary model of cancer pain caused by tumor infiltration is the cancer invasion pain model (CIP).

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC).

In addition to any of the foregoing models of chronic pain, compositions that inhibit TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain. Wang and Wang (2003).

Many individuals seeking treatment for pain suffer from visceral pain Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU. 94: 158-163). The effectiveness of a TRPA1 compound can be assessed by a decrease in writhing, gastrointestinal inflammation or bladder excitability.

The foregoing animal models are relied upon in the study of pain. The following provide additional exemplary references describing the use of these models in the study of pain: thermal injury model (Jones and Sorkin, 1998, Brain Res 810: 93-99; Nozaki-Taguchi and Yaksh, 1998, Neuroscience Lett 254: 25-28; Jun and Yaksh, 1998, Anesth Analg 86: 348-354), formalin model (Yaksh et al., 2001, J Appl Physiol 90: 2386-2402), carrageenan-model (Hargreaves et al., 1988, Pain 32:-77-88), and CFA model (Nagakura et al., 2003, J Pharmacol Exp Ther 306: 490-497).

Administration

It is preferable to administer the TRPA1 inhibitors of the invention as a pharmaceutical formulation (composition). The compositions according to the invention are formulated for administration in any convenient way for use in human or veterinary medicine. Regardless of the route of administration selected, the compositions of the present invention, which are used in a suitable hydrated form, and/or the pharmaceutical agents of the present invention, are formulated into pharmaceutically acceptable dosage forms such as described below or by other conventional methods known to those of skill in the art.

Thus, another aspect of the present invention provides pharmaceutical compositions comprising a therapeutically effective amount of one or more of the agents described herein, formulated together with one or more pharmaceutically acceptable carriers (additives) and/or diluents. As described in detail below, in some examples, the pharmaceutical compositions of the present invention are specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) for inhalation. However, in certain examples the subject agents are simply dissolved or suspended in sterile water. In certain examples, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by inhibiting TRPA1 function in at least a sub-population of cells in an animal and thereby blocking the biological consequences of that function in the treated cells, at a reasonable benefit/risk ratio applicable to any medical treatment.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to • another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations can be conveniently be presented in unit dosage form and prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations of the invention suitable for oral administration are in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. In further examples, compositions of the present invention are also administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato, or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions also comprise buffering agents in some examples. Solid compositions of a similar type also can be employed as fillers in soft and hard-filled gelatin capsules using such excipients as lactose or milk sugars, as well as high molecular weight polyethylene glycols and the like.

A tablet comprising agents of the invention can be made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the powdered compound moistened with an inert liquid diluent.

The tablets, and other solid dosage forms of the pharmaceutical compositions of the present invention, such as dragees, capsules, pills and granules, are optionally be scored or prepared with coatings and shells, such as enteric coatings and other coatings well known in the pharmaceutical-formulating art. They are also formulated so as to provide slow or controlled release of the active ingredient therein using, for example, hydroxypropylmethyl cellulose in varying proportions to provide the desired release profile, other polymer matrices, liposomes and/or microspheres. They are sterilized by, for example, filtration through a bacteria-retaining filter, or by incorporating sterilizing agents in the form of sterile solid compositions that can be dissolved in sterile water, or some other sterile injectable medium immediately before use. These compositions are also optionally contain opacifying agents and are of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Alternatively or additionally, compositions can be formulated for delivery via a catheter, stent, wire, or other intraluminal device. Delivery via such devices are especially useful for delivery to the bladder, urethra, ureter, rectum, intestine, or intrathecal delivery, for example.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compounds are mixed under sterile conditions with a pharmaceutically acceptable carrier, and with any preservatives, buffers, or propellants that are required.

The ointments, pastes, creams and gels contain, in addition to an active compound of this invention, excipients, such as animal and vegetable fats, oils, waxes, paraffins, starch, tragacanth, cellulose derivatives, polyethylene glycols, 'silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which are reconstituted into sterile injectable solutions or dispersions just prior. to use, which contain antioxidants, buffers, bacteriostats, solutes which render the formulation isotonic with the blood of the intended recipient or suspending or thickening agents.

Examples of suitable aqueous and nonaqueous carriers that are employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions also contain adjuvants such as preservatives, wetting agents, emulsifying agents or dispersing agents in some examples. Prevention of the action of microorganisms are ensured by the inclusion of various antibacterial and antifungal agents, for example, paraben, chlorobutanol, phenol sorbic acid, and the like. In some examples, it is desirable to include isotonic agents, such as sugars, sodium chloride, and the like into the compositions. In addition, prolonged absorption of the injectable pharmaceutical form is brought about by the inclusion of agents that delay absorption such as aluminum monostearate and gelatin.

In some cases, in order to prolong the effect of a drug, it is desirable to slow the absorption of the drug from subcutaneous or intramuscular injection. This is accomplished by the use of a liquid suspension of crystalline or amorphous material having poor water solubility. The rate of absorption of the drug then depends upon its rate of dissolution, which, in turn, depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compositions of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

Methods of introduction are also provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions of this invention are varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. Ultimately, the attending physician or veterinarian will decide the appropriate amount and dosage regimen.

In general, a suitable daily dose of a compound of the invention will be that amount of the compound that is the lowest dose effective to produce a therapeutic effect. Such an effective dose will generally depend upon the factors described above. Generally, intravenous, intracerebro ventricular and subcutaneous doses of the compounds of this invention for a patient will range from about 0.0001 to about 100 mg per kilogram of body weight per day.

If desired, the effective daily dose of the active composition are administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one are still detectable when the subsequent therapy is administered.

The present invention contemplates formulation of the subject compounds in any of the aforementioned pharmaceutical compositions and preparations. Furthermore, the present invention contemplates administration via any of the foregoing routes of administration.

One of skill in the art can select the appropriate formulation and route of administration based on the condition being treated and the overall health, age, and size of the patient being treated.

Combination Therapy

Another aspect of the invention provides a combination therapy wherein one or more other therapeutic agents are administered with the TRPA1 inhibitors described herein. Such combination treatment is achieved by way of the simultaneous, sequential, or separate dosing of the individual components of the treatment. In certain examples, a composition of the invention is conjointly administered with an analgesic. Suitable analgesics include, but are not limited to, opioids, glucocorticosteroids, non-steroidal antiinflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, -mefanamic acid, prednisolone, and dexamethasone. Preferred-analgesics are non-steroidal antiinflammatories and opioids (preferably morphine).

In certain examples, a composition of the invention is administered in combination with a non-steroidal anti-inflammatory. Suitable non-steroidal antiinflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

In certain examples, a composition of the invention is administered in combination with an antiviral agent. Suitable antiviral agents include, but are not limited to, amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3'-dideoxyadenosine (ddA), 2'-,3'-dideoxyguanosine (ddG), 2',3'-dideoxycytidine (ddC), 2',3'-dideoxythymidine (ddT), 2'3'-dideoxy-dideoxythyrnidine (d4T), T-deoxy-3'-thia-cytosine (3TG or lamivudime), 2t,3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2l3'-dideoxy-2I, 3l-didehydro-2'-fluorothymidine (Fd4T), 2'3'-dideoxy-2'-beta-fluoroadenosine (F-ddA), 2'3'-dideoxy-2'-beta-fluoro-inosine (F-ddI), and 2'53'-dideoxy-2'-beta-flurocytosine (F-ddC), trisodium phosphomonoformate, trifluoro thymidine, 3'azido-3' thymidine (AZT), dideoxyinosine (ddI), and idoxuridine.

In certain examples, a composition of the invention is conjointly administered with an antibacterial agent. Suitable antibacterial agents include, but are not limited to, amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, "cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxaciilin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitromrazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin. In certain examples, a compound of the invention is conjointly administered with a cough suppressant, decongestant, or expectorant.

Examples of retinoids that be administered with the subject TRPA1 inhibitors, e.g., where the TRPA1 inhibitor can be used to reduce the pain and/or inflammatory effect of the retinoid, include, but are not limited to, compounds such as retinoic acid (both cis and trans), retinol, adapalene, vitamin A and tazarotene. Retinoids are useful in treating acne, psoriasis, rosacea, wrinkles and skin cancers and cancer precursors such as melanoma and actinic keratosis.

Similarly, the subject TRPA1 inhibitors can be used in conjunction with keratolytic agents include benzoyl peroxide, alpha hydroxyacids, fruit acids, glycolic acid, salicylic acid, azelaic acid, trichloroacetic acid, lactic acid and piroctone.

The subject TRPA1 inhibitors can be used with anti-acne agents, anti-eczema agents and anti-psoratic agents. The subject TRPA1 inhibitors can also be used with skin protectants, such allantoin and esculin.

In certain examples, two or more compostions of the invention are administered in combination. When two or more compositions of the invention are conjointly administered, the two or more compositions have a similar selectivity profile and functional activity, or the two or more compounds have a different selectivity profile and functional activity. By way of example, the two or more compositions are both approximately 10, 100, or 1000 fold selective for antagonizing a function of TRPA1 over TRPV1, TRPV5, and TRPV6 (e.g., the two or more compounds have a similar selectivity profile), and further inhibit a function of TRPA1 with a similar TC50 (e.g., a similar functional activity). Alternatively, the one of the two or more compositions selectively inhibit TRPA1 while the other of the two or more compositions inhibits both TRPA1 and TRPV1 (e.g., the two or more compounds have differing selectivity profiles). Administration of combinations of two or more compounds of the invention having similar or differing properties are contemplated. In certain examples, a composition of the invention is conjointly administered with one or more additional compounds that antagonize the function of a different channel. By way of example, a composition of the invention is conjointly administered with one or more compounds that antagonize TRPV1, TRPM8, and/or TRPV3. The compound(s) that antagonize TRPV1, TPRM8, or TRPV3 are selective for TRPV1, TRPM8 or TRPV3 (e.g., inhibit TRPV1 or TRP V3 10, 100, or 1000 fold more strongly than TRPA1). Alternatively, the compound(s) that antagonize TRPV1 or TRP V3 cross react with other TRP channels.

In certain other examples, a composition of the invention is conjointly administered with one or more additional agents or therapeutic regimens appropriate for the particular injury, disease, condition, or disorder being treated.

Kits

The present invention also features kits comprising a Tmem100 mutant polypeptide, for example a Tmem100 mutant polypeptide that comprises SEQ ID NO: 1, or fragments thereof or SEQ ID NO: 3, or fragments thereof.

The kit also contains instructions for providing the Tmem100 mutant polypeptide, or fragment thereof, to a cell, for example a sensory neuron.

The kit contains instructions for use in preventing, treating, or alleviating symptoms of pain or preventing, treating, or alleviating symptoms of itch.

EXAMPLES

The discovery of Pirt provides a model for the regulation of Transient Receptor Potential (TRP) channel multi-subunit complexes. It is expressed in more than 90% of dorsal root ganglia (DRG) neurons and has been identified as a positive regulator of TRPV1 (Kim et al., 2008) and TRPM8 (Tang et al., 2013). Initially, Pirt was identified by a cDNA subtractive screen using neonatal wild-type and Ngn1−/− mouse dorsal root ganglion (DRG) to find genes specifically expressed in nociceptive neurons (Dong et al., 2001). The Pirt protein independently forms complexes with TRPV1 and TRPM8, augmenting the responses of these channels to their agonists. At the behavioral level, pain associated with these TRP channels is also reduced. Pirt −/− mice demonstrated attenuated responses to noxious stimuli such as heat, cold, and chemicals like capsaicin and icilin. Pirt −/− mice also revealed a drastic deficiency in the itch responses evoked by a wide array of pruritogens (Patel et al., 2011). Nevertheless, there is a lack of evidence showing that Pirt is able to regulate the activity of TRPA1 (Kim et al., 2008). Here studies describe other Pirt-like proteins and peptides that regulate TRPs and modify their functions in a variety of TRP channel complexes.

Using the protein sequence of Pirt, another gene has been identified, Tmem100, with the working name of Tmem100 given its similar structural and biochemical properties. Like Pirt, Tmem100 is a 134 amino-acid two-transmembrane protein with both N- and C-termini being intracellular and an amino acid sequence that is highly conserved in vertebrates (Moon et al., 2010). Thus, both Pirt and Pirt2 (i.e., Tmem 100) have similar protein size, membrane topology, and function, i.e., regulating TRP channels in DGR neurons. Unlike the restricted expression pattern of Pirt, Tmem100 is expressed more widely in other organs besides the DRG. It is expressed as early as embryonic day 9.5 (E9.5) in the dorsal aorta and from E10.5 to E12.5 in other vessels, ventral neural tubes, and the notochord (Moon et al., 2010). It is reported to be associated with renal development (Georgas et al., 2009), vasculogenesis (Moon et al., 2010; Somekawa et al., 2012), lung cancer cell invasiveness (Frullanti et al., 2012), body height in African-Americans (Carty et al., 2012), and apoptosis (Yamazaki et al., 2011). However, little is known about the underlying mechanisms of these Tmem100-associated effects and its role in the nervous system.

A large body of evidence indicates that TRP channels are capable of assembling into heterotetrameric channel complexes. This phenomenon was originally reported for TRPC channels: TRPC1 co-assembles with TRPC4 and TRPC5 in the rat brain (Strubing et al., 2001). In mammals, the formation of various TRP channel complexes containing channels from the TRPC (Goel et al., 2002; Hofmann et al., 2002; Strubing et al., 2003), TRPV (Hellwig et al., 2005; Rutter et al., 2005; Smith et al., 2002), TRPM (Chubanov et al., 2004), and TRPP (Schaefer, 2005) families have been demonstrated. Thus, TRPs are able to heteromerize within the same subfamily (e.g., TRPV1 and TRPV3) (Cheng et al., 2012) and across subfamilies (e.g., TRPV4 and TRPP2) (Kottgen et al., 2008). The subunit composition influences the biophysical and regulatory properties of the resulting channel complex (Xu et al., 1997). They have unique biophysical and pharmacological properties and are modulated via distinct pathways (Cheng et al., 2012). It was demonstrated that the TRPA1-TRPV1 (TRPA1-V1) complex is present in sensory neurons with unique biophysical properties (Salas et al., 2009; Staruschenko et al., 2010). Since TRPA1 and TRPV1 contribute significantly to peripheral and central mechanisms of pain and hypersensitivity (Julius, 2013), the TRPA1-V1 complex could be clinically important. In addition, regulation of this TRP channel complex could provide specificity in the management of pain and hypersensitivity in various pathophysiological conditions.

The present work identifies Tmem100 as a potentiating modulator of TRPA1-V1 complexes. Tmem100 is co-expressed with TRPA1 and TRPV1 in peptidergic DRG neurons. Tmem100-deficient mice show a reduction in inflammatory hypersensitivity and TRPA1- but not TRPV1-mediated pain. Single-channel recording in a heterologous system reveals that Tmem100 selectively potentiates TRPA1 activity in the TRPA1-V1 complex in a TRPV1-dependent manner. Mechanistically, Tmem100 weakens the association of TRPA1 and TRPV1 and thereby releases the inhibition of TRPA1 by TRPV1. A Tmem100 mutant, Tmem100-3Q, exerts the opposite effect, i.e. it enhances the association of TRPA1 and TRPV1 and strongly inhibits TRPA1. Strikingly, a cell permeable peptide (CPP) sharing the C-terminal sequence of Tmem100-3Q mimics its effect in the presence of TRPV1, selectively inhibiting TRPA1-mediated pain. The studies described herein unveil a context-dependent modulation of the TRPA1-V1 complex, and Tmem100-3Q CPP represents a novel therapeutic for pain management.

Figure 4:
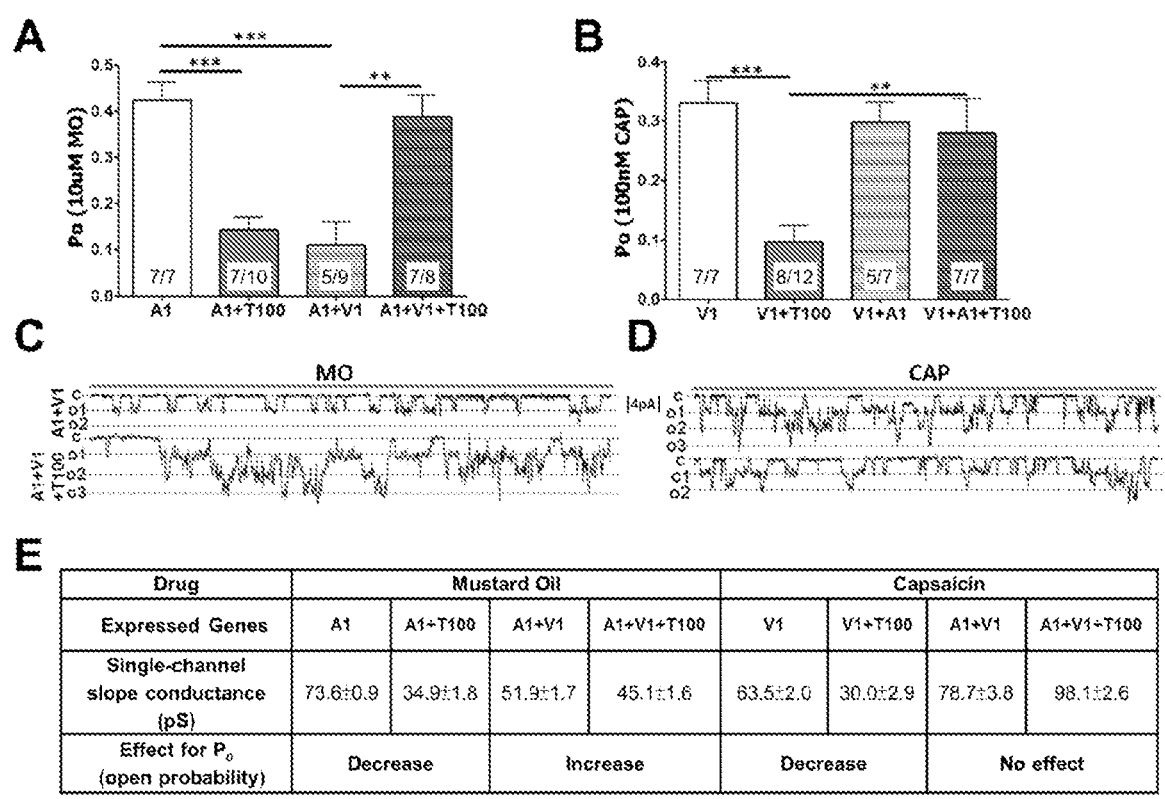
FIG. 4A-FIG. 4E demonstrate context-dependent regulation of Tmem100 in the TRPA1-V1 complex.
Figure 5:
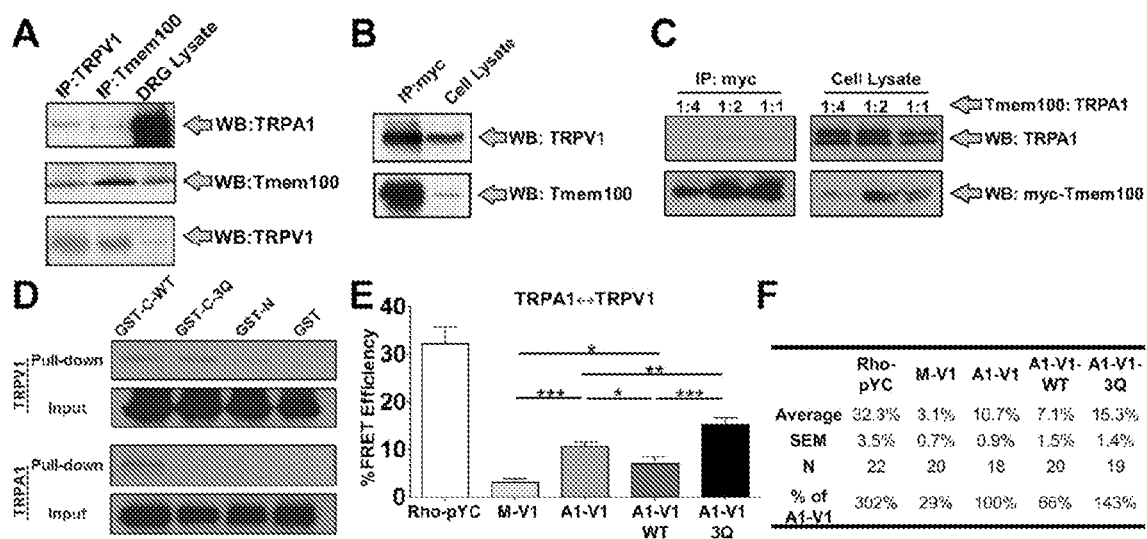
FIG. 5 is an image of a Co-IP of TRPV1 and full-length myc-Tmem100 in TRPV1-expressing cells. The results show an interaction between Tmem100 and TRPV1.
Figure 8:
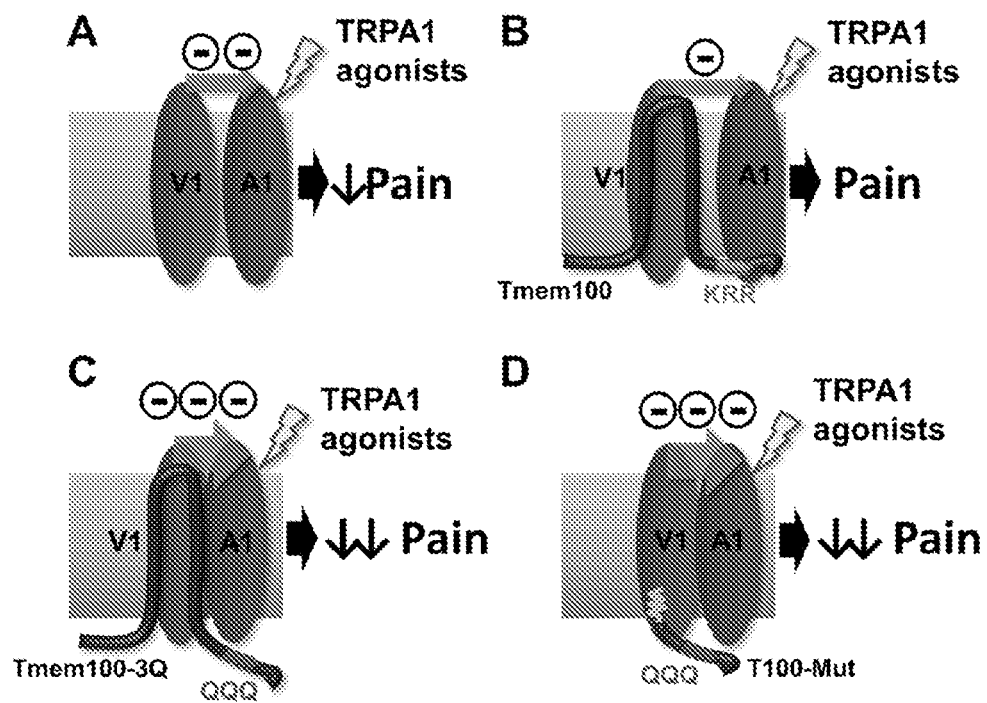
FIG. 8A-FIG. 8D illustrate a schematic model for the modulatory effects of TRPV1 on TRPA1 alone (FIG. 8A), WT Tmem100 (FIG. 8B), Tmem100-3Q (FIG. 8C), and T100-Mut CPP (FIG. 8D) (with myristoylated group inserted into the plasma membrane as shown by the orange wiggly line). The distance between TRPA1 and TRPV1 represents the degree of association (the smaller the distance, the stronger the association). The number of minus signs and the size of the green arrows represent the relative strength of inhibition of TRPA1 by TRPV1.

Studies propose a putative TRPA1-V1 complex model in which a membrane adapter protein—Tmem100—regulates the physical association between TRPA1 and TRPV1 (FIG. 8). Further studies demonstrate that TRPA1 activity is inhibited by TRPV1 when the two channels are co-expressed in the absence of Tmem100 (FIGS. 4A, 8A) (Salas et al., 2009). When Tmem100 is present, TRPA1 activity is potentiated in a TRPV1-dependent fashion (FIGS. 2A-2J; 4A-4E). The presence of Tmem100 weakens the TRPA1-V1 association by physical interaction with both channels (FIGS. 5E, 8B), which results in disinhibition of TRPA1 and a net positive effect on TRPA1-associated activity in the TRPA1-V1 complex. Moreover, Tmem100-3Q (with stronger interaction with TRPV1 and no interaction with TRPA1; FIGS. 5 and 13A-13D) exerts the opposite effect, tightening the physical association between TRPA1 and TRPV1 (FIG. 5E); TRPA1 inhibition by TRPV1 is increased (FIGS. 8C, 8D). The uniqueness of Tmem100 is that it not only provides a feasible model of regulation for TRPA1-V1 complexes but also demonstrates selectivity and context dependency.

Tmem100 preferentially augments the responses to TRPA1 agonists in the TRPA1-V1 complex whereas the responses to TRPV1 agonists remain relatively unchanged. This phenomenon is consistent from single channels all the way to the behavioral level. Electrophysiological and biochemical results indicate that Tmem100 is able to physically associate with TRPA1 and TRPV1 alone and modulate them. However, these regulatory effects are inhibitory in nature for both TRPA1 and TRPV1 homomers. Interestingly, the inhibitory effects of Tmem100 were not observed in DRG neurons and behavioral assays. One possible explanation is that most TRPA1$^+$ DRG neurons also express TRPV1; therefore, the amount of TRPA1 homomer could be minimal in DRG neurons in either normal or pathological conditions (Diogenes et al., 2007). An alternate possibility is that Tmem100 modulates channels other than the TRPA1-V1 complex and contributes to other phenotypes (Somekawa et al., 2012). Data from a heterologous expression system suggested that Tmem100 inhibit CAP-mediated responses in TRPV1$^+$/TRPA1$^-$ DRG neurons. One explanation is that Tmem100 has low expression levels in the TRPV1$^+$/TRPA1$^-$ neuronal subset (FIG. 1). Studies will test this possibility.

The discovery of Tmem100 also reconciles the inconsistent effects of TRPV1 on TRPA1-mediated currents reported in native sensory neurons versus heterologous systems (Salas et al., 2009). MO-induced currents were smaller in sensory neurons from TRPV1$^{-/-}$ mice. This is in contrast to the expected increase in currents since TRPV1 inhibits TRPA1 in heterologous systems. Data described herein provides an explanation for the underlying mechanisms. In Tmem100$^{-/-}$ DRG neurons, as seen in the heterologous system, TRPA1-mediated activity was lowered compared to Tmem100$^{+/+}$ neurons, presumably due to the inhibitory effect of TRPV1. Heterologous studies show that Tmem100 itself also inhibits TRPA1 activity in the absence of TRPV1 (compare the "A1" and "A1+T100" columns in FIGS. 4A and S4A). Since TRPA1$^+$ sensory neurons from TRPV1$^{-/-}$ mice still express Tmem100, the MO-gated currents would be inhibited by Tmem100. This inhibition is exactly what previous studies (Salas et al., 2009) and data provided herein (compare the open bars in FIGS. 7D and 7H) have found in TRPV1$^{-/-}$ DRG neurons and mice. Therefore, taking into account the modulatory action of Tmem100, the data collected from heterologous cells and native neurons are now consistent and suggest that the interaction between TRPV1 and TRPA1 leads to an inhibition of TRPA1 by TRPV1.

Several lines of evidence indicate that Tmem100 plays an important role in pain and inflammation. First, treatment with NSAIDs and immunosuppressants reduces its expression (Yamazaki et al., 2011). Second, inflammatory pain is reduced in Tmem100 sensory neuron-specific knockout mice. Third, Tmem100 is exclusively expressed in peptidergic DRG neurons, which are crucial for neurogenic inflammation (FIG. 1H). Lastly, TRPA1 and TRPV1, both key targets of Tmem100 modulation, are critical regulators of inflammatory pain (Bautista et al., 2006; Caterina et al., 2000). Thus, an approach that interferes with this pathway will provide specificity to control pain under pathological conditions and will consequently be important in pain management.

The discovery and subsequent characterization of the T100-Mut cell-permeable peptide is an avenue for the management of pain. The extent of the inhibitory effect of T100-Mut is comparable to that of other potent TRPA1 antagonists (da Costa et al., 2010; McNamara et al., 2007; Petrus et al., 2007). The major advantage of this approach is to maximize the specificity and thus minimize the possible side effects of drugs by specifically targeting the TRPA1-V1 complex instead of TRP homomers expressed in other tissues. Therefore, studies described and proposed herein on Tmem100 lead to a better understanding of the processing, modulation, and management of pain.

Example 1: Materials and Methods

Generation of Tmem100 GFP Knock-in Mouse Line

Full-length Tmem100 cDNA from mouse DRG was cloned into the pGEM T-Easy vector (Promega) and later subcloned into the expression vector pcDNA3.1. The arms of the Tmem100 targeting constructs were subcloned from ES cell genomic DNA. The gene deletion constructs eliminated exon 3, which contains the entire coding region of Tmem100. PmeI and AscI restriction sites were engineered so the EGFPf-ACN cassette could be placed in the middle of the two arms. A negative selection marker (DTA) was placed outside of the right arm to increase homologous recombination rate. Tmem100$^{GFP/+}$ mice were generated using the targeting construct by the Transgenic Core Laboratory at the Johns Hopkins University. Generation of the mutant allele and excision of the ACN cassette were verified by PCR and Southern blotting.

Generation of Tmem100 Conditional Knockout Mice

A BAC clone containing the entire Tmem100 genomic sequence was purchased from Children's Hospital Oakland Research Institute and modified by recombineering (Liu et al., 2003). The final gene targeting vector contains exon 3 and a PGK-Neo cassette flanked by two loxP sites. The two homologous arms are 1.9 and 6.0 kb in size, respectively. Tmem100$^{fl/+}$ mice were generated using the targeting construct by the Transgenic Core Laboratory at the Johns Hopkins University. Homologous recombination in ES cells was verified by PCR for both arms with a long range PCR kit (Roche, 04829034001) and sequencing. Germline transmission was confirmed by PCR. The F1 progeny were mated with FlpE mice to eliminate the PGK-Neo cassette, and the results were verified with PCR targeting the Neo cassette. For the behavioral studies, mice were crossed with WT C57/BL6 for more than 5 generations before mating to an Avil$^{+/CRE}$ line.

Western Blot of DRG Lysate

DRG from cervical to lumbar levels were collected in 300 µL PBS and 2% SDS with protease inhibitor (Sigma P8340). After sonication, the solution was centrifuged at 18,000 rcf for 5 minutes in 4 degrees. The supernatants were collected and stored at −80 degrees. For the western blots, DRG lysates were separated by SDS-PAGE (10% or 15% for Tmem100 detection) and wet transferred to PVDF membranes (GE Healthcare, RPN303F). The membranes were blocked with 5% milk in TBST for 30 minutes. The primary antibodies used were: 1:5000 anti-Tmem100, 1:1000 anti-TRPV1 (Santa Cruz, R130), and 1:1000 anti-TRPA1 (Novus, NB110-40763). Secondary antibodies for visualization included donkey anti-rabbit and anti-mouse HRP-conjugated antibodies (GE Biosciences). The intensities for the signals were analyzed using ImageJ.

Co-Immunoprecipitation (Co-IP)

DRG from all levels or CHO cells transfected with Trpv1, Trpa1, and Tmem100-myc were used. Whole cell DRG or CHO cells lysates were generated 24 h after transfection, and Co-IP with either 1 µg myc antibody (EMD Millipore) or 1 µg TRPV1 antibody (Santa Cruz, R130) as described (Akopian et al., 2007) Immunoprecipitants and cell lysate aliquots were resolved by SDS-PAGE and immunoblotted with 1:1000 anti-TRPV1 antibody (Santa Cruz, R130), 1:500 anti-Tmem100 antibody, 1:1000 anti-TRPA1 (Novus), or 1:1000 anti-myc (EMD Millipore). Secondary antibodies for visualization included donkey anti-rabbit and anti-mouse HRP-conjugated antibodies (GE Biosciences).

GST Pull-Down

The GST-N, GST-C fusion, and GST constructs (2 µg) were individually transfected with 2 µg of Trpa1, Trpv1, Trpm8, and Trpv2 constructs into HEK293T cells with Lipofectamine 2000. Twenty-four hours later, cells were washed with PBS and lysed with 500 µL IP buffer (1% Triton X-100+protease inhibitor in PBS). After sonication and centrifugation for 10 min at 13,000 rpm at 4° C., the supernatants were incubated with glutathione-agarose beads (GE bioscience). The bound proteins were eluted from the beads by heating in 2× protein sample buffer at 50° C. for 10 minutes. The samples were resolved by SDS-PAGE and immunoblotted with 1:2500 rabbit polyclonal anti-TRPV1 antibody (Santa Cruz, R130), 1:1000 rabbit anti-TRPA1 antibody (Novus), 1:5000 anti-GST antibody (Sigma A7360), or 1:10000 donkey anti-rabbit HRP-conjugated antibody (GE Bioscience NA934V).

Behavioral Assays

Hot Plate Methods

Mice were placed in a clear plexiglass cylinder on top of a temperature-controlled metal plate (Life Science Series 8, Model 39.) The latency of acute nocifensive responses was determined by the onset of hindpaw lifts and/or licking, flinching, or jumping.

Tail Immersion Test

Mice were restrained in an apparatus made of 50 mL conical tubes. Their tails were exposed in the water bath set to the designated temperatures.

Von Frey Methods

Mice were placed in a transparent plastic box (4.5×5×10 cm) on a metal mesh and acclimatized for 30 minutes prior to testing. Each mouse was tested more than 5 times at a specific force manually, and the threshold was determined by the lowest force needed to elicit responses more than 50% of the time.

Mustard Oil Injection

Mice were injected intradermally in the hind paw with 6 µL of 0.2% mustard oil (Sigma-Aldrich 377430) with Hamilton needles (80300). The mice were placed in a plexiglass cylinder, and the total time spent licking and flinching was recorded for the first 10 minutes after injection. Thirty and sixty minutes after injection, the mice were assayed with von Frey filaments for mechanical hyperalgesia.

Hargreaves Test

Mice were placed under a transparent plastic box (4.5× 5×10 cm) on a glass platform (Plantar Test Apparatus, IITC Life Science). Radiant heat was adjusted to 18% of maximal output and shone on the center of the paws. Each mouse was tested more than 3 times, with each test performed 20 minutes apart.

CFA Injection

Mice were injected with 6 μL of 50% emulsified Complete Freund's Adjuvant (Sigma, F5881) in normal saline.

Capsaicin Injection

Mice were injected with 6 μL of capsaicin (0.1 μg/μL in normal saline/10% ethanol/0.5% Tween 80) in the hindpaws. The mice were placed in a plexiglass cylinder, and the total time spent licking and flinching was recorded for the first 10 minutes after injection.

Paclitaxel Injection

Mice were injected with paclitaxel (Sigma T7191) intraperitoneally at the dose of 6 mg/kg, as previously described (Materazzi et al., 2012). Seven days after paclitaxel injection, the mice were assayed with Von Frey methods for mechanical hyperalgesia, both before and four hours after injection of cell permeable peptides.

Cold Plate Test

A metallic plate on a bed of ice was cooled in a −20° C. freezer. During the test, the plate was allowed to warm to 0° C. as measured by the temperature probe. The onset of brisk hindpaw lifts and/or flicking/licking of the hindpaw was assessed.

Rat L5 SNL

An modified L5 SNL model was produced as described in previously (He et al., 2014; Shechter et al., 2013). Male Sprague-Dawley rats (200-350 g, Harlan, Indianapolis, Ind.) were anesthetized with 2% isoflurane. The left L5 spinal nerve was ligated with a 6-0 silk suture and cut distally. The muscle layer was closed with 4-0 chromic gut suture and the skin closed with metal clips. For intrathecal catheter implantation, a small slit was cut in the atlanto-occipital membrane of rats, into which a saline-filled piece of PE-10 tubing (6-7 cm) was inserted (He et al., 2014). After completing the experiment, it was confirmed intrathecal drug delivery by injecting lidocaine (400 μg/20 μl, Hospira, Lake Forest, Ill.), which resulted in a temporary motor paralysis of the lower limbs. Hypersensitivity to punctuate mechanical stimulation was determined with the up-down method by using a series of von Frey filaments (0.38-15.1 g) applied for 4-6 seconds to the test area on the plantar surface of the hindpaw (Chaplan et al., 1994; He et al., 2014). The PWT was determined according to the formula provided by Dixon (Dixon, 1980). Rats that underwent SNL but did not develop mechanical hypersensitivity (>50% reduction of PWT from pre-SNL baseline) by day 5 post-SNL and rats that showed impaired motor function or deteriorating health after treatment were eliminated from the subsequent behavioral studies, and data were not analyzed. HC-030031 was purchased from Tocris Bioscience (Bristol, UK). Both drugs were dissolved in 10% dimethylsulfoxide (DMSO), 5% Tween 80 and 85% sterile saline solution. The final working solution which was injected by intrathecal route contained <1% DMSO. The number of animals used in each study was based on experience with similar studies and power analysis calculations. Animals were randomized to the different treatment groups and blinded the experimenter to drug treatment to reduce selection and observation bias. After the experiments were completed, no data point was excluded. STATISTICA 6.0 software (StatSoft, Inc., Tulsa, Okla.) was used to conduct all statistical analyses. The Tukey honestly significant difference (HSD) post-hoc test was used to compare specific data points. Bonferroni correction was applied for multiple comparisons. Two-tailed tests were performed, and data are expressed as mean±SEM; $P<0.05$ was considered significant in all tests.

Calcium Imaging

Calcium imaging assays were performed as previously described (Liu et al., 2009). Cells were loaded with 2 μM fura 2-acetomethoxy ester (Molecular Probes) for 30 min in the dark at room temperature or for 45 minutes at 37° C. for DRG and cell lines, respectively. After washing, cells were imaged at 340 and 380 nm excitation to detect intracellular free calcium under a fluorescent microscope (Nikon Eclipse TE2000-S) and Lambda 10B shutter (Sutter Instrument). The cells were bathed in calcium imaging buffer (pH 7.45, 130 mM NaCl, 3 mM KCl, 2.5 mM $CaCl_2$, 10 mM HEPES, 10 mM glucose, 1.2 mM $NaHCO_3$, with sucrose to increase osmolarity to 290 mOsm). The reagents and buffers were applied through a gravity perfusion system at a rate of 2 mL/s, including mustard oil (Sigma 377430), cinnamaldehyde (Sigma C80687), menthol (Sigma M2780), and capsaicin (Sigma M2028). Cells with high baseline 340/380 values (>1.5) were excluded for analysis. For DRG neurons, $IB_4$ staining was performed in the chamber with the dilution of 1:200 (Molecular Probes 121412) for 160 seconds before washing off at the end of each test. Images were processed and analyzed with NIS-Elements BR 2.30 software (Nikon). A responsive cell was defined as one that with greater than a 20% increase in the 340/380 ratio above the baseline. Intracellular calibration for calcium was performed as previously described (Akopian et al., 2007). The data was analyzed with the experimenter blinded to the genotypes or constructs transfected.

Cell Culture

DRG from 3 to 4-week old mice were collected in cold DH10 medium (90% DMEM/F-12, 10% FBS, 100 U/ml penicillin, and 100 μg/ml Streptomycin, Gibco) and treated with enzyme solution in HBSS containing collagenase (1.65 mg/mL, Worthington CLS I) and dispase (3.55 mg/mL, GIBCO 17105-041) at 37° C. for 30 minutes. After trituration and centrifugation, cells were resuspended in DH10, plated on glass coverslips coated with poly-D-lysine (0.5 mg/ml, Stoughton, Mass.) and laminin (10 μg/ml, Invitrogen), and cultured overnight in an incubator at 37° C. The neurons were tested within 24 hours. HEK293T, COS-7, and CHO cells were cultured in a medium consisting of 90% DMEM, 10% FBS, 100 U/mL penicillin, and 100 μg/ml Streptomycin. GlutaMAX (Gibco 35050-061) was also added for CHO cells. For calcium imaging, the cells were plated on glass coverslips coated with poly-D-lysine (0.5 mg/ml, Stoughton, Mass.). In the HEK cell studies the denominator is the cells expressing both TRPA1, TRPV1, and the designated constructs (i.e. Tmem100 or Tmem100-3Q mutant). mCherry:TRPV1:Tmem100 was transfected in 1:8:8 ratio into TRPA1 stable cell line (obtained from N. Tigue from GlaxoSmithKline) and used mCherry as the marker for the cells expressing the constructs 18 hours after transfection with Lipofectamine 2000. The transfection efficiency for Tmem100+TRPV1+TRPA1 triple-positive cells is 27±3%. This efficiency was determined by mCherry(+) divided by total number of cells in the bright fields.

Electrophysiology

Recordings were made in cell-attached single-channel or whole-cell voltage clamp configurations at 22-24° C. from the somata of small-to-medium mouse DRG neurons (15-35 pF) or CHO cells. For whole-cell configuration, holding potential (Vh) is −60 mV. Data were acquired and analyzed using an Axopatch 200B amplifier and pCLAMP9.0 software (Molecular Devices, Sunnyvale, Calif.). Borosilicate pipettes (Sutter, Novato, Calif.) were pulled and polished to resistances of 3-5 MΩ (in whole-cell and single-channel pipette solutions). Access resistance (Rs) was compensated (40-80%) when appropriate up to the value 7-10 MΩ for whole-cell configuration. Whole-cell recording data were filtered at 0.5 kHz and sampled at 2 kHz. Single-channels currents were filtered with an 8-pole, low pass Bessel filter at 0.1 kHz and sampled at 0.5 kHz, since dwelling time (τ) of the TRPA1 and TRPV1 single-currents were >0.5 sec. Whole-cell recorded data were rejected when Rs changed >20% during recording, leak currents were >100 pA, or input resistance was <200 MΩ. Currents were considered positive when their amplitudes were 5-fold bigger than displayed noise (in root mean square).

Single-channel unitary current (i) was determined from the best-fit Gaussian distribution of amplitude histograms. Single-channel activity was analyzed as NPo=I/i, where I is the mean total current in a patch and i is unitary current at this voltage. Open probability (Po) for main conductance is presented in figures. For single channel slope conductances, linear fitting was used separately for positive and negative holding potentials. The slope conductances presented in figures were determined from fitting negative hold potentials (from −60 to 0 mV). The single-channel recording data were analyzed with Clampfit 9 software. This has an "event detection analysis" function that analyzes current traces and determines the number of channels in the patch (N), how many sub-conductances are present, and what the main conductance is. In order to increase the accuracy of the Po measurement, only patches containing fewer than 3 channels were used. For patches containing both TRPA1 and TRPV1, only those with equal numbers of TRPA1 and TRPV1 were used. This was monitored in each recording by applying MO and then CAP.

Standard external solution (SES) for whole-cell patch recording contained (in mM): 140 NaCl, 5 KCl, 2 CaCl$_2$, 1 MgCl$_2$, 10 D-glucose and 10 HEPES, pH 7.4. Vehicle, which is 0.01% DMSO, was added to external solutions. The bath solution for single-channel recording (SES-SCh) of TRP currents consisted of (in mM): 100 K-gluconate, 4 KCl, 1 MgCl$_2$, 1 EGTA, 10 D-glucose and 10 Hepes (pH 7.3). The standard pipette solution (SIS) for the whole-cell configurations contained (in mM): 140 KCl, 1 MgCl$_2$, 1 CaCl$_2$, 10 EGTA, 10 D-glucose, 10 HEPES, pH 7.3. The pipette solution for single-channel recording (SIS-SCh) was (mM): 100 Na-gluconate, 10 NaCl, 1 MgCl$_2$, 2 CaCl$_2$, 10 D-glucose and 10 HEPES (pH 7.3). Drugs were applied using a fast, pressure-driven, computer controlled 8-channel system (ValveLink8; AutoMate Scientific, San Francisco, Calif.). The baseline activities of the cells were recorded for 1-2 min prior drug applications. The durations of drug applications are noted in legends to figures. Single-channel analyses of traces were performed from the 10th to 30th seconds after commencing drug applications.

Immunofluorescent Staining

Adult mice of 8-12 weeks old were anesthetized with pentobarbital and perfused with 20 ml 0.1 M phosphate-buffered saline (PBS; pH 7.4; 4 degrees) followed with 25 ml 4% paraformaldehyde and 14% picric acid in PBS (4 degrees). After perfusion, spinal cords and dorsal root ganglia (DRG) were dissected. DRG was post-fixed in 4% paraformaldehyde and 14% picric acid at 4 degrees for 30 mM and spinal cord was fixed for 1 hr. All tissues were cryoprotected in 20% sucrose in PBS at 4 degrees overnight, and preserved in OCT at −80 degree. Before staining, twenty nm sections were post-fixed with 4% paraformaldehyde in PBS for 10 minutes and washed with 0.1% PBST. After blocking in 10% goat serum in PBST for 1 hour at room temperature, sections were incubated with primary antibodies at 4° C. overnight. The primary antibodies used were: rabbit anti-GFP (Invitrogen, 1:1000), chicken anti-GFP (Invitrogen, 1:1000), rabbit anti-CGRP (Bachem T-4239, 1:1000), rabbit anti-NF200 (Sigma N4142, 1:1000), rabbit anti-TRPV1 (gift from Dr. Caterina, 1:1000), IB$_4$ (Molecular Probes 1-21412, 1:200), mouse anti-NeuN (Millipore MAB377, 1:300), and rabbit anti-TRPA1 (gift from Dr. Schmidt, 1:200). On the second day, the sections were incubated with secondary antibodies at room temperature for 1 hour. The secondary antibodies used were: goat anti-rabbit (Invitrogen A11036, Alexa 568-conjugated; A11034, Alexa 488-conjugated), goat anti-chicken (Invitrogen A11039, Alexa 488-conjugated), goat anti-rat (Invitrogen A11434, Alexa 555-conjugated), and goat anti-mouse IgG1 (Invitrogen A-21124, Alexa 568-conjugated; A-21121, Alexa 488 conjugated). All secondary antibodies were diluted 1:300 in the blocking solution. Sections were washed with PBST and mounted with Fluoromount-G (Southern BioTech). Images were obtained using the Zeiss LSM700 confocal microscope system.

Live Staining

F11 cell line was transfected with 0.6 μg of either pcDNA$_{3.1}$-Tmem100-myc or pcDNA$_{3.1}$-Tmem100+0.2 μg mCherry following Lipofectamine 2000 protocol. On the second day, the cells were trypsinized and plated on 150 mm coverslips coated with poly-D-lysine. The non-detergent-treated (NDT) groups were washed 3 times with buffer consisting of 1% goat serum in PBS. The detergent-treated (DT) groups were fixed with 4% PFA in PBS for 15 minutes at room temperature and washed with buffer consisting of 1% goat serum in 0.1% PBST. After washing, the coverslips were blocked in 10% goat serum in their respective washing buffers for 15 minutes at room temperature. They were incubated with primary antibodies (1:200 mouse anti-c-myc ab, 9B11, 1 mg/mL) or 1:1000 rabbit anti-Tmem100 antibody for 1 hour at room temperature and washed 3 times. They were incubated with secondary antibodies (1:1000 goat anti-mouse IgG-488 (Invitrogen) or goat anti-rabbit IgG-488 (Invitrogen)) for 30 min at room temperature.

Total Internal Reflection Fluorescence (TIRF) Microscopy and Förster Resonance Energy Transfer (FRET)

Expression vectors of pEYFP-TRPA1 (YFP on C-terminal part), pECFP-TRPV1 (CFP on C-terminal part), and pEYFP-N1 were transfected into COS-7 cells with FuGENE HD (Promega E2311), as previously described (Staruschenko et al., 2010). COS-7 cells were chosen since they have flat morphology and thus suitable for TIRF-FRET analysis. Moreover, previously it has been shown that CHO and COS cells express TRPA1 and TRPV1 to the same level (Staruschenko et al., 2010). Data from fixed cells were collected in separate facilities at University of Texas Health Science Center, San Antonio, and the Johns Hopkins University, respectively. Each group was co-transfected with full-length pcDNA$_{3.1}$-Tmem100, pcDNA$_{3.1}$-Tmem100-3Q, or pcDNA$_{3.1}$-myc/His and plated on glass-bottom dishes (MatTek, P35G-1.0-14-C). FRET was essentially performed as previously described (Staruschenko et al., 2010). Briefly, two days after transfection, the cells were fixed for 15 min with 4% paraformaldehyde in PBS and then imaged at the room temperature using total internal reflection fluorescence (TIRF) (also called evanescent-field) microscopy on an inverted Nikon Eclipse TE200U microscope equipped with a plain Apo TIRF 60× oil-immersion, high-resolution (1.45 NA) objective. The CFP and YFP fluorophores were excited with a 442-nm Melles Griot dual-pulsed solid state and 514-nm argon ion laser, respectively, with an acoustic optic tunable filter used to select excitation wavelengths (Prairie Technology, Middleton, Wis.). Emissions from CFP and YFP passed through an image splitting device (Dual-View, Optical Insights, Tucson, Ariz.) using a 505-nm dichroic filter to split emissions, which then passed through 470±15 and 550±25 nm emission filters, respectively. Fluorescence images were collected and processed with a 16-bit, cooled charge-coupled device camera (Cascade 512F; Roper Scientific Inc.) interfaced to a PC running Metamorph software.

Each cell was photobleached by argon-ion laser (514 nm) at full power for 2 min. It was demonstrated previously preferential photo-bleaching of membrane proteins in and near the plasma membrane abutting the coverglass versus total cellular pools of the channel with TIRF illumination (Staruschenko et al., 2010). The % FRET efficiency was calculated as the percent increase in CFP after photobleaching:

$$\% \; FRET = (CFPpost - CFPpre)/CFPpost$$

where CFPpost and CFPpre are the mean grey values of CFP emission in the cells after and before photobleaching subtracted by its background, respectively. All images were analyzed in ImageJ.

Cell Permeable Peptides

The sequence from the last 28 amino acids of the C-terminus of the Tmem100-3Q mutant protein was synthesized and myristoylated at its N-terminus (myr-WKVRQRNKKVQQQESQTALVVNQRCLFA-COOH) (SEQ ID NO: 8) by Twentyfirst Century Biochemicals. The scrambled peptide was synthesized with the same composition and did not resemble any known protein (myr-QRVLEQVLQNWSRRANVKQAQKFQVKCT-COOH) (SEQ ID NO: 15). For the calcium imaging assay, the peptides were added to the calcium imaging buffer with a final concentration of 200 nM and incubated for at least 30 mM at room temperature. For the mice behavioral assays, the peptides (5 µL, 2 mM) were injected subcutaneously in the hindpaw at least 30 minutes before testing. For the rat behavior assays, human T100-3Q (h-T100), a palmitoylated cell permeable peptide mutated based on the C terminus of human sequence in Tmem100, was applied. The sequence is Palmitoyl-WKVRQRSKKAQQQESQTALVANQRSLFA-COOH (SEQ ID NO: 7).

Statistical Analysis

Error bars are presented as mean±SEM. Numerical data in the text is presented as mean±SEM. n represents the number of mice, individual responding cells or individual tests analyzed. Statistical comparisons between two groups were conducted by two-tailed, unpaired Student's t test. Multiple groups were compared and analyzed by using one-way ANOVA and Bonferroni's post-hoc test (where each column was compared to all other columns). Differences between groups with genotype and time as factors were accessed by two-way ANOVA with Bonferroni's multiple comparison post-hoc tests. Power analysis was used to justify the sample size. Differences were considered as statistically significant for $p < 0.05$. Representative data are from experiments that were replicated biologically at least three times with similar results.

Figure 9:
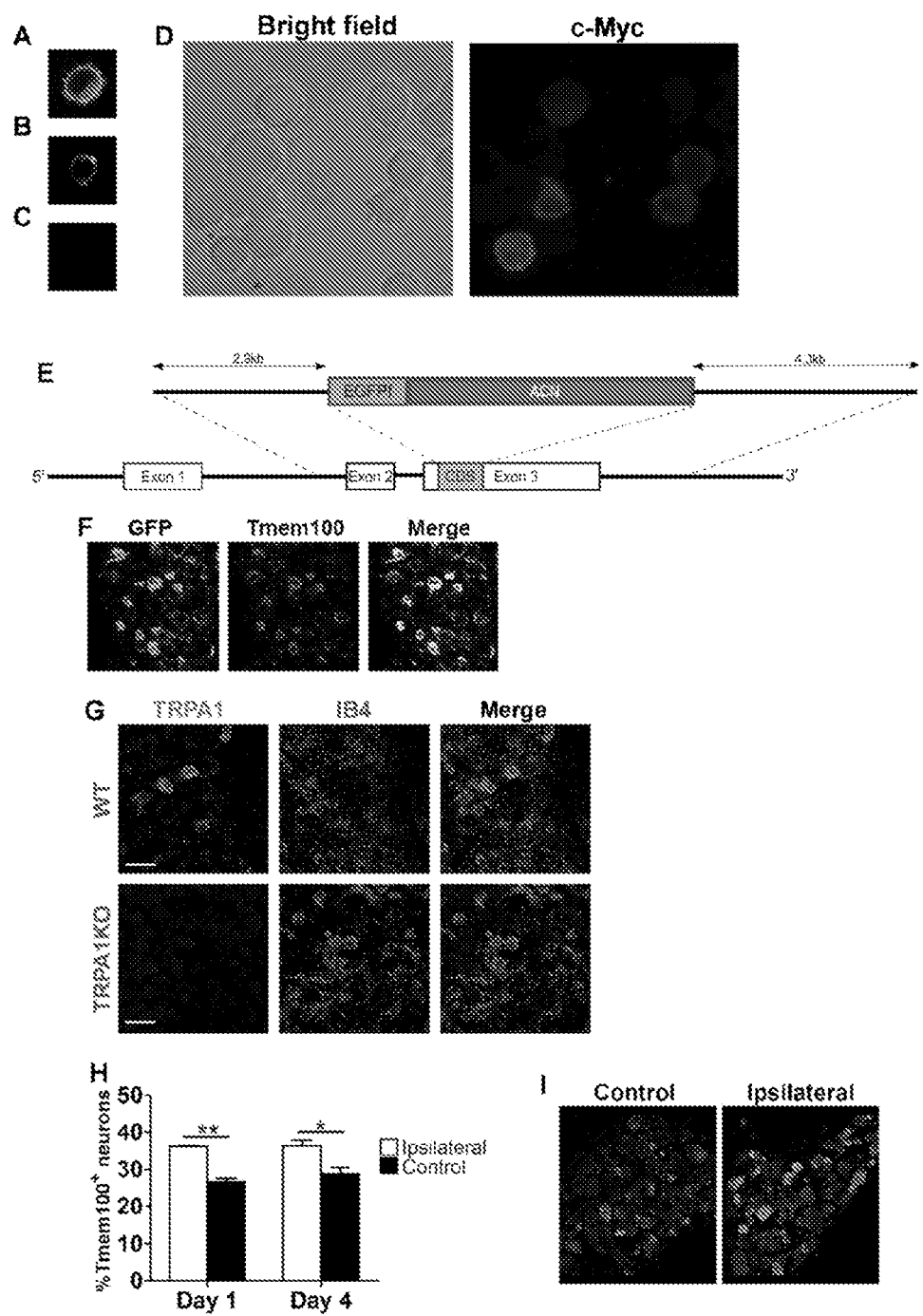
FIG. 9A-FIG. 9I are related to FIG. 1A-FIG. 1F.

Example 2: Tmem100 Encodes a Two-Transmembrane Protein Expressed in Peptidergic DRG Neurons Topology of Tmem100 was invested to understand its cellular localization and distribution. Protein structure analysis (PredictProtein, Columbia University, and SOSUI, Nagoya University, Japan) indicates that Tmem100 is a two-transmembrane protein (FIG. 1A). Tmem100-myc construct was transfected with c-myc at the C-terminus into the F11 cell line and stained with anti-myc antibody. Tmem100 was visualized at the plasma membrane only after membrane permeabilization (FIGS. 9A,C). Similar results were obtained with anti-Tmem100 antibody against the N-terminus (FIG. 9B). Staining also showed that the signal was primarily located in the plasma membrane (FIG. 9D). The data indicate that Tmem100 is a two-transmembrane protein largely localized to the plasma membrane with intracellular localization of both N- and C-termini.

To characterize Tmem100-expressing DRG neurons, a knock-in line was generated in which the open reading frame of Tmem100 was replaced with GFP (Tmem100$^{GFP/+}$; FIGS. 9E,F). Anti-Tmem100 antibody labelling confirmed that GFP is specifically expressed in Tmem100$^+$ DRG neurons in the Tmem100$^{GFP/+}$ mouse line (FIG. 9F). Using GFP as a marker, it was found that Tmem100 was expressed in 24% of lumbar DRG neurons (mainly small and medium in size) (FIG. 1B). Different DRG neuron markers were double stained with GFP in the Tmem100$^{GFP/+}$ line (FIGS. 1C,D, and 9G). Ninety-five percent of Tmem100$^+$ neurons express CGRP, and 88.4% of CGRP neurons express Tmem100. Both TRPA1 and TRPV1 are co-expressed in a subset of Tmem100$^+$ neurons. In contrast, Tmem100$^+$ neurons were rarely positive for IB$_4$ (FIGS. 1C,D, and 11). These results suggest that Tmem100 is primarily expressed in peptidergic DRG neurons (FIG. 1E), many of which are TRPV1 and TRPA1 double-positive (FIG. 1F) (Bautista et al., 2006; Story et al., 2003). A recent study has shown that TRPA1 is functionally expressed in IB4$^+$ non-peptidergic neurons (Barabas et al., 2012). The culture conditions of dissociated DRG neurons can influence the expression of TRPA1. On the other hand, the sensitivity of anti-TRPA1 antibody misses the expression of TRPA1 in IB4$^+$ neurons. Moreover, it was found that a significant increase in the number of Tmem100-expressing neurons in the DRG under inflammatory conditions induced by complete Freund's Adjuvant (CFA) injection (FIG. 9H,I). Collectively, the expression data suggest that Tmem100 is involved in the modulation of pain.

Figure 2:
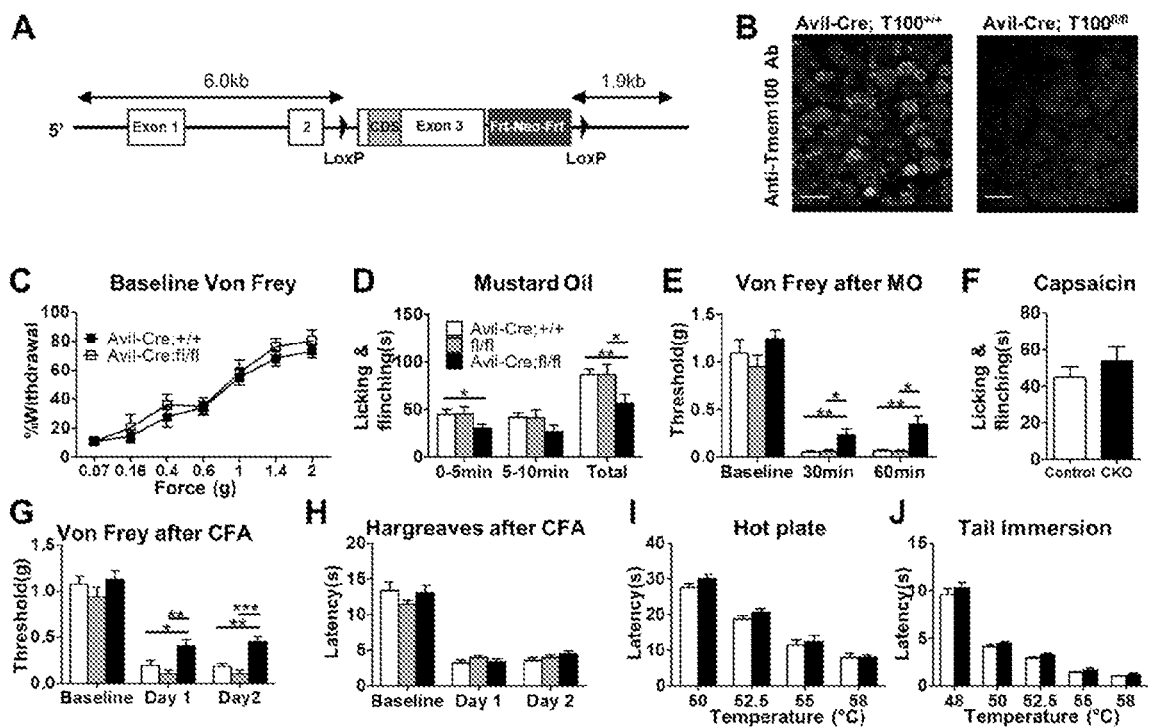
FIG. 2A-FIG. 2J demonstrate that Tmem100 CKO mice show selective deficits in TRPA1-associated behaviors while TRPV1-associated behaviors are unaffected.
Figure 10:
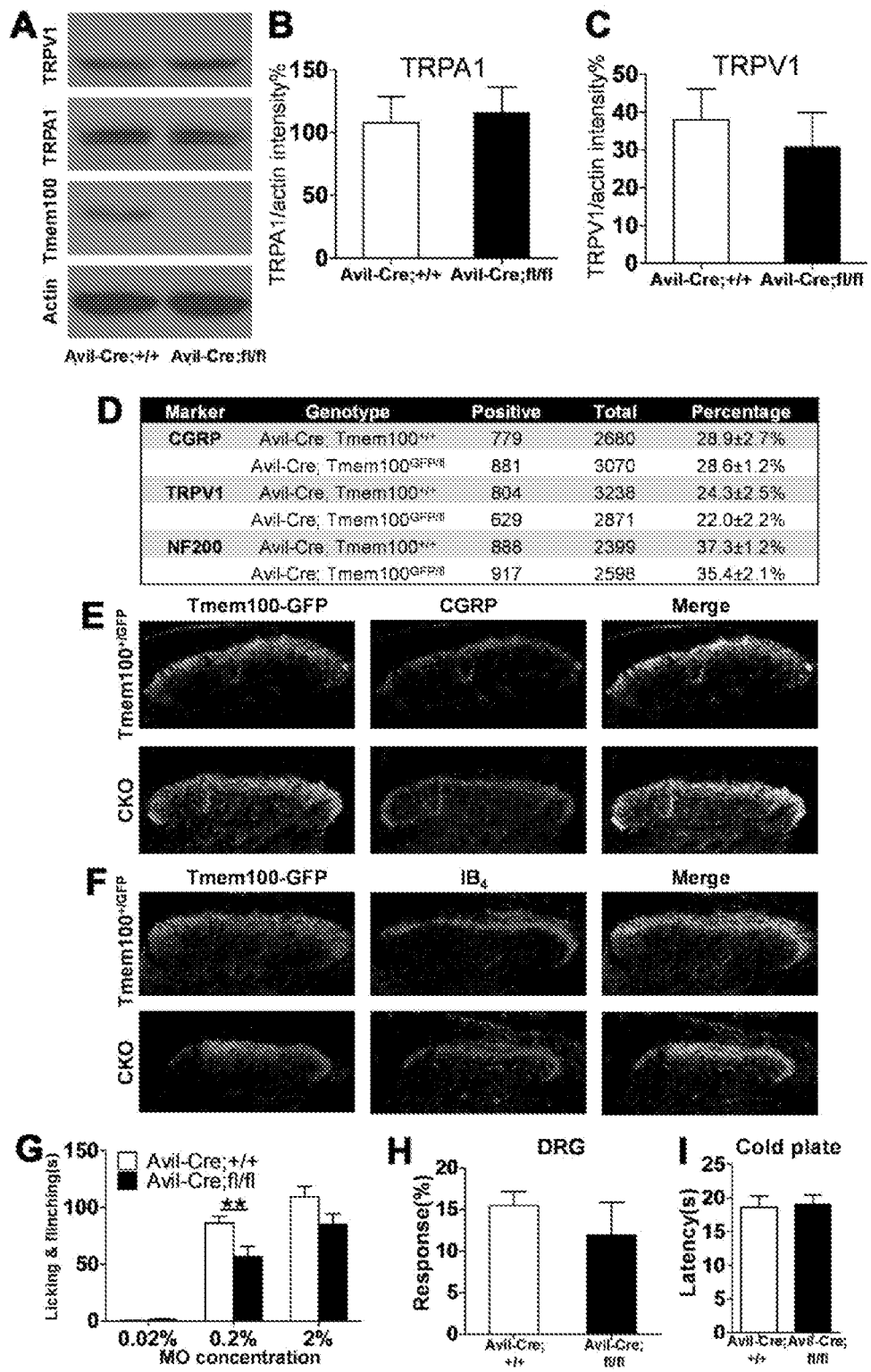
FIG. 10A-FIG. 10I are related to FIG. 2A-FIG. 2J.

Example 3: Selective Elimination of Tmem100 in Sensory Neurons Leads to a Reduction of Mechanical Hyperalgesia and TRPA1-Associated Nociception Conditional knockout mice were generated to study the function of Tmem100 in the nociceptive pathway (Tmem100$^{fl/fl}$; FIG. 2A) because a global knockout of Tmem100 is lethal at E10.5 (Moon et al., 2010). Tmem 100$^{fl/fl}$ mice were mated with male Advillin$^{+/CRE}$ (Avil-Cre) mice to selectively eliminate Tmem100 in primary sensory neurons of the DRG (Hasegawa et al., 2007). These mice were viable, and there were no obvious differences in gross appearance and behavior among wild-type (WT), Avil-Cre; Tmem100$^{+/+}$, Tmem100$^{fl/fl}$, and Avil-Cre;Tmem100$^{fl/fl}$ mice. The deletion of Tmem100 protein in the DRG was verified by immunofluorescent staining and Western blotting with a rabbit anti-Tmem100 antibody (FIGS. 2B and 10A). No significant changes in TRPA1 and TRPV1 expression were observed in the DRG when Tmem100 was eliminated (FIGS. 10A-C). Moreover, developmental and morphological phenotypes were evaluated in the DRG and spinal cord from Avil-Cre;Tmem100$^{GFP/fl}$ lines, and the results did not suggest any related defects (FIGS. 10D-F).

Next it was determined whether Tmem100 plays a role in nociception and hyperalgesia/allodynia by performing behavioral tests on Tmem100 DRG conditional knockout mice, i.e., Avil-Cre;Tmem100$^{fl/fl}$ (Tmem100 CKO). These mice exhibited normal mechanical sensitivity under naive conditions (FIG. 2C). However, Tmem100 CKO mice exhibited reduced acute nocifensive behaviors induced by mustard oil (MO; an agonist of TRPA1 (Bautista et al., 2006; Kwan et al., 2006)) compared to Avil-Cre;Tmem100$^{+/+}$ and Tmem100$^{fl/fl}$ controls (FIGS. 2D and 10G). TRPA1-dependent mechanical hyperalgesia generated by injection of MO into mouse hindpaws (Bautista et al., 2006) was also significantly decreased in Tmem100 CKO mice (FIG. 2E). The average threshold for mechanically induced pain was reduced to 0.06 g in both control groups and was significantly higher (0.34 g) in Tmem100 CKO mice. In the inflammatory pain model generated by injection of CFA into the hindpaws, Tmem100 CKO mice also showed attenuated mechanical hyperalgesia (FIG. 2G), consistent with a previous report on the involvement of TRPA1 in inflammatory mechanical hyperalgesia (Petrus et al., 2007). The mechanical nociceptive threshold was reduced to 0.18 g and 0.11 g in Avil-Cre;Tmem100$^{+/+}$ and Tmem100$^{fl/fl}$ mice, respectively, but was 0.43 g in Tmem100 CKO mice at day 2. These data show that deletion of Tmem100 in the DRG leads to a substantial reduction of inflammatory mechanical hyperalgesia and acute TRPA1-associated nociception.

Interestingly, TRPV1-associated acute nociceptive behavior and hyperalgesia remained relatively unperturbed in Tmem100 CKO mice. Tmem100 CKO mice did not show any significant deficits in capsaicin-induced acute nocifensive behavior in the hindpaw (FIG. 2F). Tail immersion and hot plate tests also failed to reveal any deficits in the mutant mice (FIGS. 2I and 2J). Furthermore, CFA-induced thermal hyperalgesia, which is almost completely reversed after TRPV1 deletion but unaltered after pharmacological blockade of TRPA1 (Caterina et al., 2000; Petrus et al., 2007), was also unchanged in Tmem100 CKO mice (FIG. 2H). Cold-induced pain was also tested in these animals, and the results suggest that this modality is not affected by the elimination of Tmem100 (FIGS. 10H,I).

Figure 3:
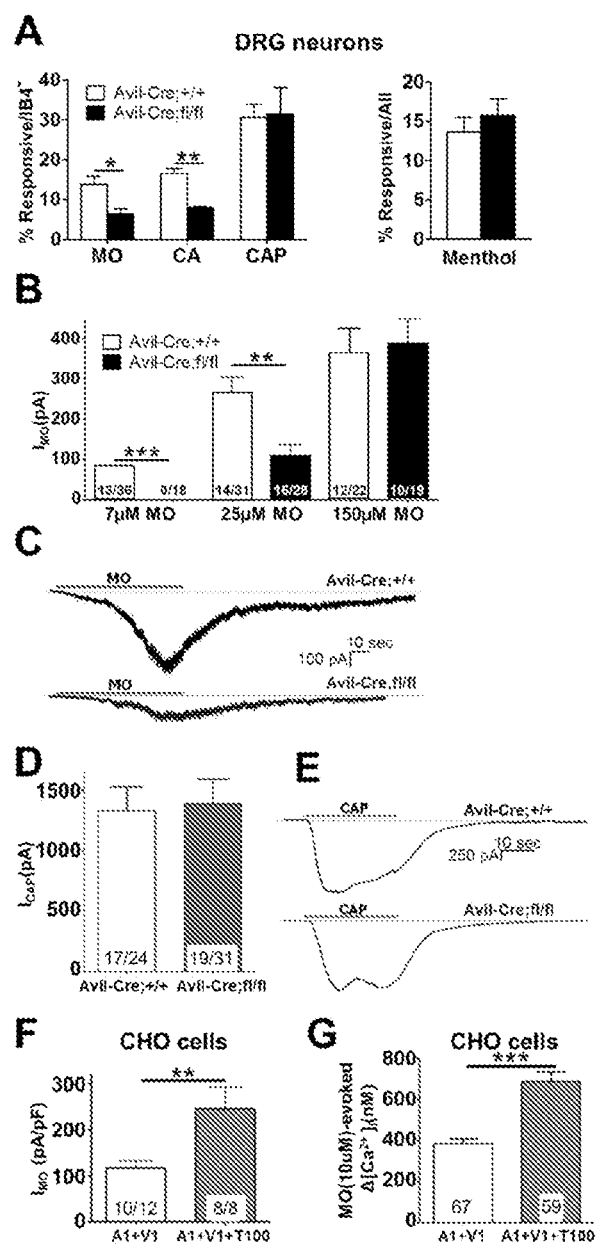
FIG. 3A-FIG. 3G indicate that Tmem100 enhances TRPA1-mediated responses in a TRPV1-dependent manner.
Figure 11:
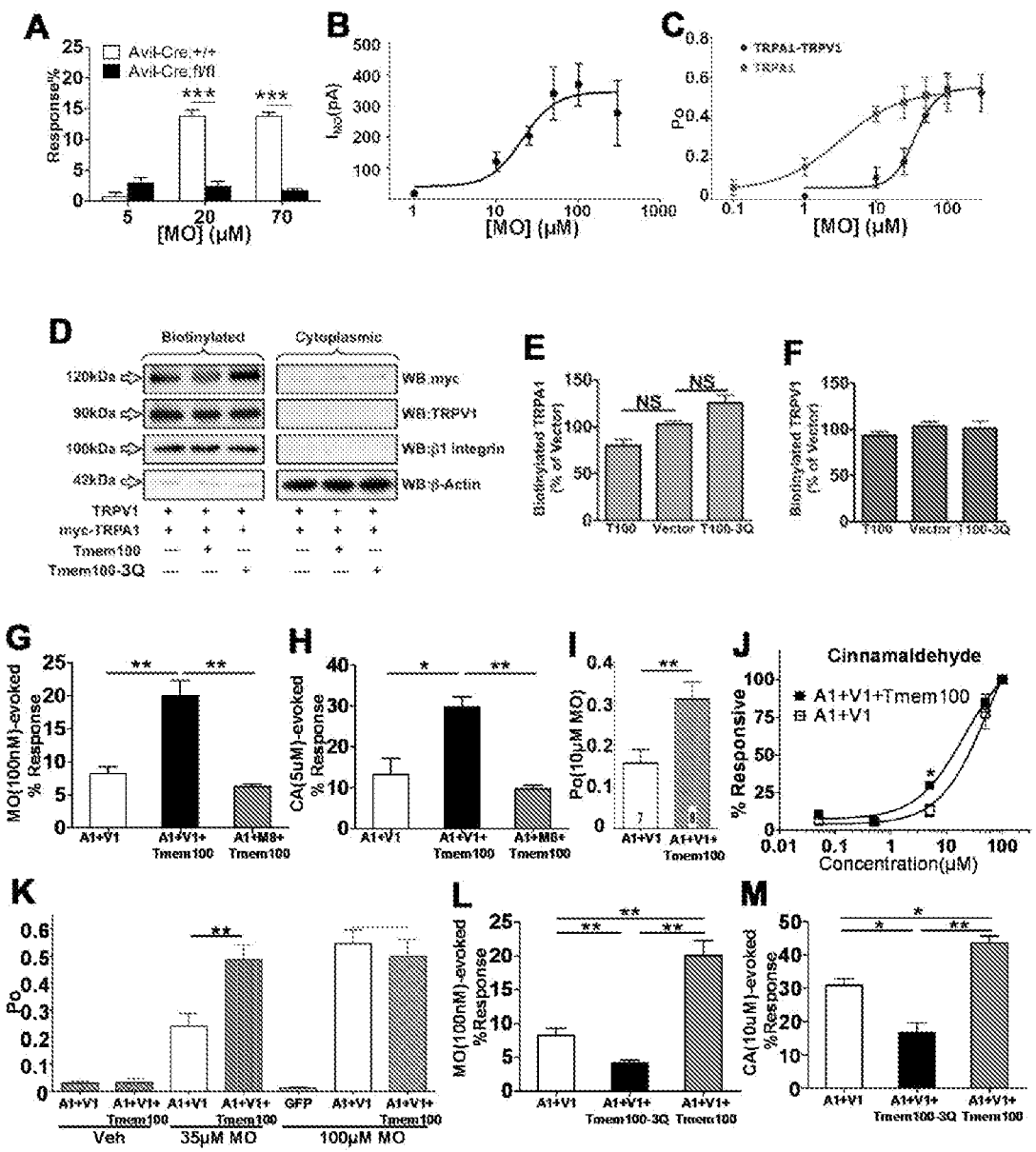
FIG. 11A-FIG. 11M are related to FIG. 3A-FIG. 3G.

Example 4: TRPA1-Mediated Responses are Selectively Attenuated in DRG Neurons from Tmem100 CKO Mice To investigate the function of Tmem100 at a cellular level, cultured DRG neurons from Tmem100 CKO mice were examined with calcium imaging and whole-cell electrophysiology recording. The results showed a selective reduction in TRPA1- but not TRPV1- or TRPM8-mediated activities in the DRG neurons when Tmem100 was deleted. In calcium imaging, only IB4-negative DRG neurons were analyzed since the majority of IB4$^+$ neurons do not express Tmem100 (in cultured conditions, only 4.8±0.8% IB4$^+$ neurons expressed Tmem100, and 5.2±0.5% of Tmem100$^+$ neurons were IB4$^+$; >900 neurons from 3 mice were analyzed for each marker). The percentage of DRG neurons responsive to MO and the alternative TRPA1-specific agonist cinnamaldehyde (CA) was significantly lower when Tmem100 was eliminated (Bandell et al., 2004) (FIGS. 3A and 11A). Fourteen and 17% of DRG neurons from Avil-Cre;Tmem100$^{+/+}$ mice (i.e. controls) showed responses to MO and CA, respectively, and the percentages dropped to 6% and 8% in the Tmem100 CKO group. Conversely, the percentage of DRG neurons with TRPV1 activity remained unchanged as 31% of IB4-negative DRG neurons responded to capsaicin in both Avil-Cre;Tmem100$^{+/+}$ and Tmem100 CKO mice. Menthol was also used as a control and observed no difference in the percentage of neurons responsive to menthol, which is mostly mediated by TRPM8 at this concentration (Bautista et al., 2006; Dhaka et al., 2007), between the control and Tmem100 CKO neurons (FIG. 3A).

Whole-cell patch clamp recording of DRG neurons was carried out to investigate regulation of TRPA1 and TRPV1-mediated currents by Tmem100. The currents evoked by 7 and 25 μM MO (based on the dose-response curve in FIG. 11B) in capsaicin (CAP)-responsive neurons were significantly smaller in DRG neurons from Tmem100 CKO mice compared to Avil-Cre;Tmem100$^{+/+}$ neurons (FIGS. 3B,C). This finding also showed that Tmem100 enhances TRPA1 activity.

The effect of Tmem100 on TRPV1-mediated responses was also examined. CAP (100 nM)-evoked currents in DRG neurons were not significantly different between Avil-Cre;Tmem100$^{+/+}$ and Tmem100 CKO mice (FIGS. 3D,E). Therefore, Tmem100 shows no modulatory effect on TRPV1 activity.

Example 5: Tmem100 Enhances TRPA1 Activity in Heterologous Expression Systems

Since both behavioral and cellular analyses suggest native Tmem100 positively regulates TRPA1, next it was asked if it was possible to reproduce a similar effect in a heterologous system. To mimic the situations in wild-type and Tmem100$^{-/-}$ DRG neurons, co-expression of TRPA1 and TRPV1 in CHO cells in the presence or absence of Tmem100 was performed. MO-evoked whole-cell current density and intracellular calcium accumulation were significantly higher when Tmem100 was present with TRPA1 and TRPV1 (FIGS. 3F,G). A biotinylation assay revealed a trend of decreasing TRPA1 levels (not statistically significant) on the plasma membrane when wild-type Tmem100 was co-expressed with both TRPV1 and TRPA1, whereas TRPV1 levels on the plasma membrane remained unchanged (FIGS. 11D-F). Because the effect of Tmem100 on TRPA1 trafficking to the plasma membrane is opposite that of its enhancement of channel activity, the true effect of Tmem100 on the whole cell are even stronger if the lowering effect on membrane trafficking of the TRPA1 channel is taken into account.

To demonstrate that Tmem100's actions can be reproduced in an alternative heterologous expression system, co-expression TRPA1 and TRPV1 in HEK293T cells was performed. Tmem100 rendered 30% and 20% of cells responsive to CA and MO, respectively, whereas only 13% and 8% of cells responded to the same agonist in the control group without Tmem100. Interestingly, this enhancement was abolished when TRPV1 was replaced by TRPM8 (FIGS. 11G,H), suggesting TRPM8 does not have an inhibitory effect on TRPA1 as TRPV1 does. Moreover, Tmem100 also lowered the EC$_{50}$ to CA by almost threefold compared to the control group (FIG. 11J). These results suggest that Tmem100 selectively enhances TRPA1 activity at the whole cell level. Importantly, this positive effect requires the presence of TRPV1.

Figure 12:
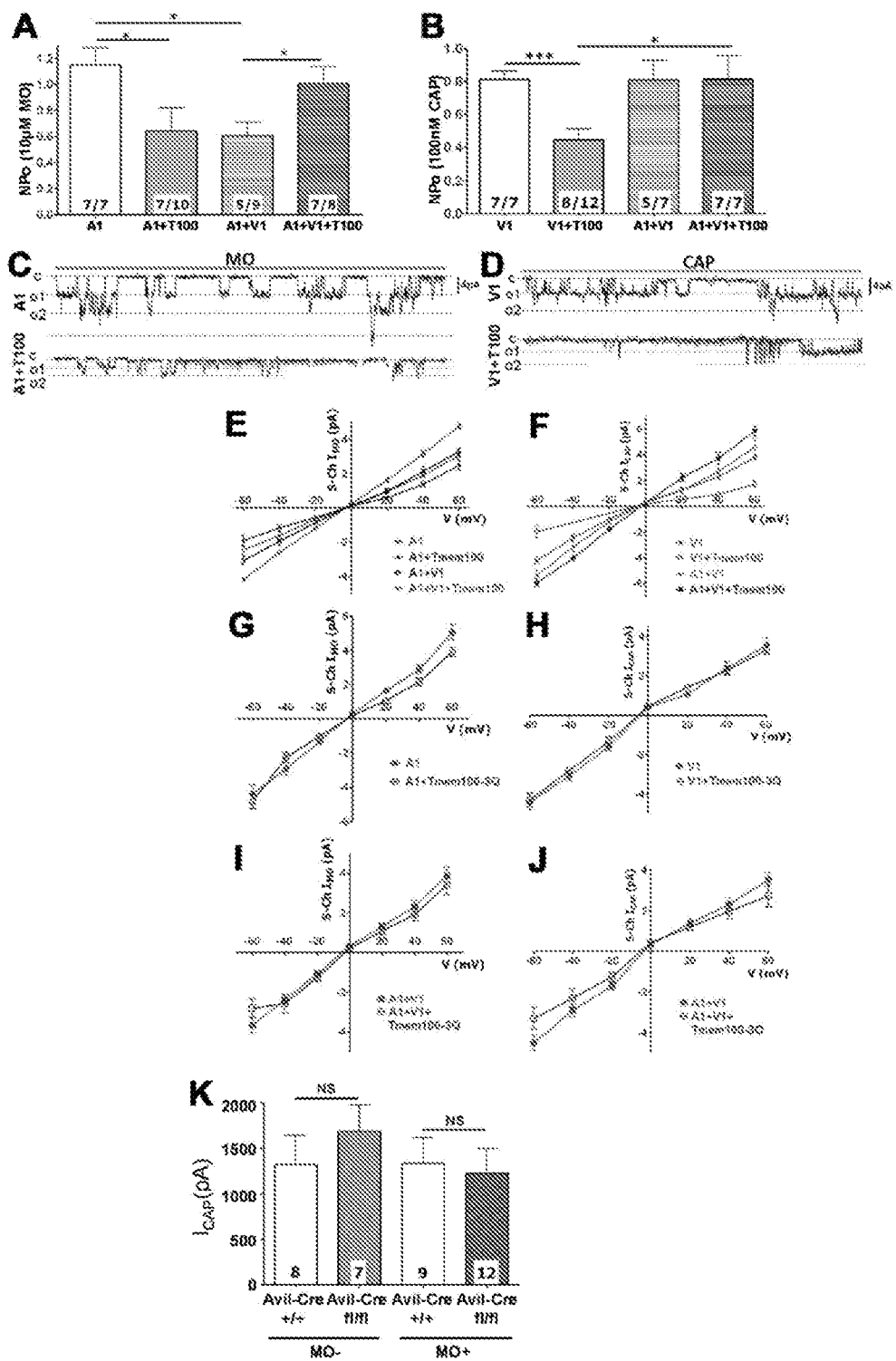
FIG. 12A-FIG. 12K are related to FIG. 4A-4E.

Example 6: Tmem100 Selectively Increases the Single-Channel Open Probability of the TRPA1-V1 Complex to Mustard Oil but not Capsaicin To analyze the effect of Tmem100 on TRPA1 and TRPV1 channel properties, cell-attached single-channel recordings were performed. Using CHO cells expressing various combinations of Tmem100, TRPA1, and TRPV1, open probabilities (Po), single-channel activity (NPo), and conductance in response to MO and CAP were investigated. The presence of TRPA1-V1 in the recording patch was confirmed with single-channel responses to both CAP and MO. When Tmem100 was co-expressed with TRPA1 and TRPV1, a substantial increase was seen in the TRPA1 Po; there was no increase in TRPA1 unitary single-channel conductance (FIGS. 4A,E 11K, and 12E). The presence of Tmem100 also caused a higher percentage of cells to respond to MO and CA (FIG. 11L,M). This modulation is not a dose-dependent effect based on the ratio of Tmem100 to TRPA1 or TRPV1 since the experiments with a different transfection ratio of Tmem100 still yielded similar results (FIG. 11I). Interestingly, co-expression of Tmem100 with TRPA1 in the absence of TRPV1 significantly reduced the TRPA1 Po for both the main conductance and unitary single-channel conductance (FIGS. 4A,E, 12C, and 12E). Recordings of TRPV1 and TRPA1, in both heterologous expression systems and sensory neurons, exhibit multiple single-channel sub-conductance states (Nagata et al., 2005; Premkumar et al., 2002; Staruschenko et al., 2010). This sub-conductance will influence the whole-cell response; therefore, to examine the sub-conductance contributions, the effects of Tmem100 on single-channel activity (NPo) of TRPA1 and TRPV1 were also analyzed. FIG. 12A illustrates that Tmem100 regulates TRPA1 NPo in the same way it affects Po, i.e., Tmem100 increases the TRPA1 NPo in the presence of TRPV1 and reduces its activity when TRPV1 is absent.

TRPV1 single-channel Po and unitary conductance, as assessed by the application of CAP, was relatively unaffected by Tmem100 when TRPA1 was also present in patches (FIGS. 4B,E, and 12F). However, Tmem100 reduced single-channel CAP responses in CHO cells expressing TRPV1 alone; this effect was much weaker in DRG neurons (FIG. 12K). Taken together, these results suggest that Tmem100 requires TRPV1 to increase intrinsic activity of TRPA1. Tmem100 inhibits the intrinsic activity of individual TRPA1 and TRPV1 channels when the two are not co-expressed.

Example 7: Tmem100 Binds Both TRPA1 and TRPV1

To test the possibility that the functional interaction of Tmem100 with TRPA1 and TRPV1 is due to a complex assembled in sensory neurons, co-immunoprecipitation (co-IP) experiments from DRG lysates were performed. The results show that Tmem100 forms complexes with endogenous TRPA1 and TRPV1 in mouse DRG (FIG. 5A). Furthermore, to investigate the contribution of each protein to complex formation, co-IP experiments using heterologous cells co-expressing Tmem100 with either TRPA1 or TRPV1 were carried out. Co-IP with full-length Tmem100-myc suggested that Tmem100 forms complexes with TRPV1 and TRPA1 individually (FIGS. 5B,C). Glutathione S-tranferase (GST) pull-down studies using different fragments of Tmem100 further characterized the distinct binding properties of its N- and C-termini. Both TRPA1 and TRPV1 separately could be pulled down with the C-terminal fragment of Tmem100; however, the same conditions with the N-terminus of Tmem100 only pulled down TRPV1 (FIG. 5D). These results indicate that Tmem100 can physically interact with TRPA1 and TRPV1.

Figure 13:
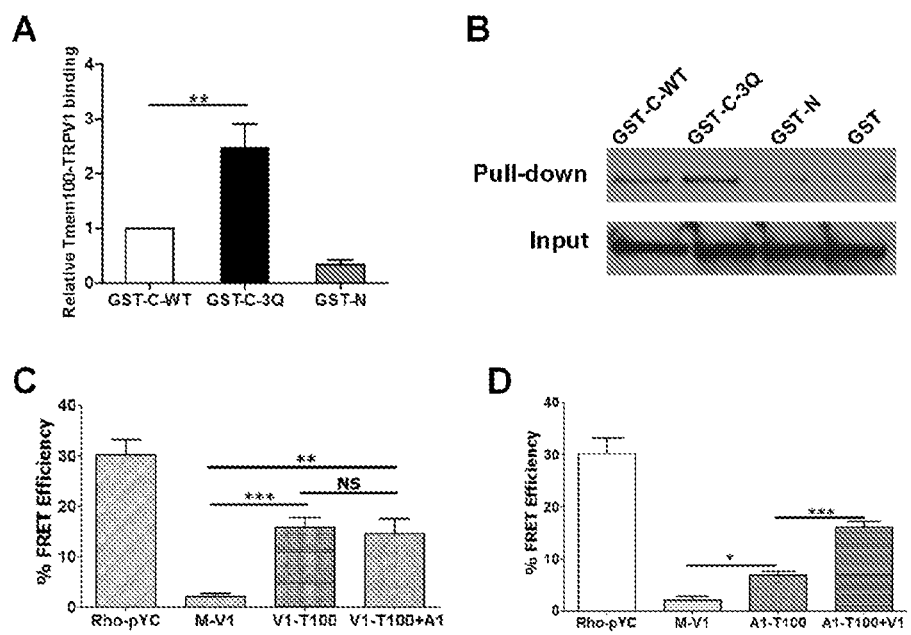
FIG. 13A-FIG. 13D are related to FIG. 5A-FIG. 5F and demonstrate the interaction among Tmem100, TRPA1, and TRPV1.

The K-R-R sequence in the C-terminus of Tmem100 was targeted because of its positive charges and conservation in vertebrates (Moon et al., 2010). To investigate the functional significance of this sequence, it was mutated to an uncharged Q-Q-Q sequence (Tmem100-3Q mutant). Interestingly, the Q-Q-Q mutation appeared to exert different effects on TRPA1 and TRPV1 binding. For TRPA1, the binding was abolished when the Q-Q-Q mutation was introduced to the C-terminus (GST-C-3Q). For TRPV1, this mutation did not appear to weaken binding but instead enhanced it (FIGS. 5D and 13A,B). These data show that although the C-terminus of Tmem100 binds to both TRPA1 and TRPV1, its binding sites to these two channels are different. Therefore, Tmem100-3Q can exert distinct modulatory effects on TRPA1 and TRPV1 compared to wild-type Tmem100.

Example 8: Wild-Type Tmem100 Weakens the Physical Association of TRPA1-V1 Whereas Tmem100-30 Enhances it Förster resonance energy transfer (FRET) and total internal reflection fluorescence (TIRF) microscopy were used to search for physical evidence of the modulatory mechanisms of Tmem100 on the TRPA1-V1 complex. Cells co-expressing TRPV1-CFP and TRPA1-YFP exhibited a significantly higher FRET efficiency than cells co-expressing TRPV1-CFP and membrane-tethered YFP ("A1-V1" versus "M-V1" in FIG. 5E). This implies that TRPA1 and TRPV1 form a complex in the plasma membrane. Strikingly, wild-type Tmem100 weakened the surface TRPA1-V1 interaction, decreasing the FRET efficiency by 34% compared to the efficiency of cells expressing only TRPA1-V1. By contrast, the Tmem100-3Q mutant enhanced the TRPA1-TRPV1 interaction by 43% (FIGS. 5E,F). These data suggest that Tmem100 modulates the physical interaction of the TRPA1/TRPV1 complex, with wild-type Tmem100 and Tmem100-3Q exerting opposite effects on these interactions. In a separate FRET-TIRF experiment, the physical interaction between TRPA1 and Tmem100 were found to be further augmented in the presence of TRPV1 whereas that of TRPV1 and Tmem100 is unaffected by TRPA1 (FIGS. 13C,D). In addition, the interaction of TRPA1 and Tmem100 is weaker than that of TRPV1 and Tmem100 (comparing "V1-T100" and "A1-T100" columns in FIG. 13C,D). The FRET data suggest preferential interactions between the three components. This result also shows that the physical interaction among the three proteins is not allosteric interaction, but occurs via specific interaction domains.

Figure 6:
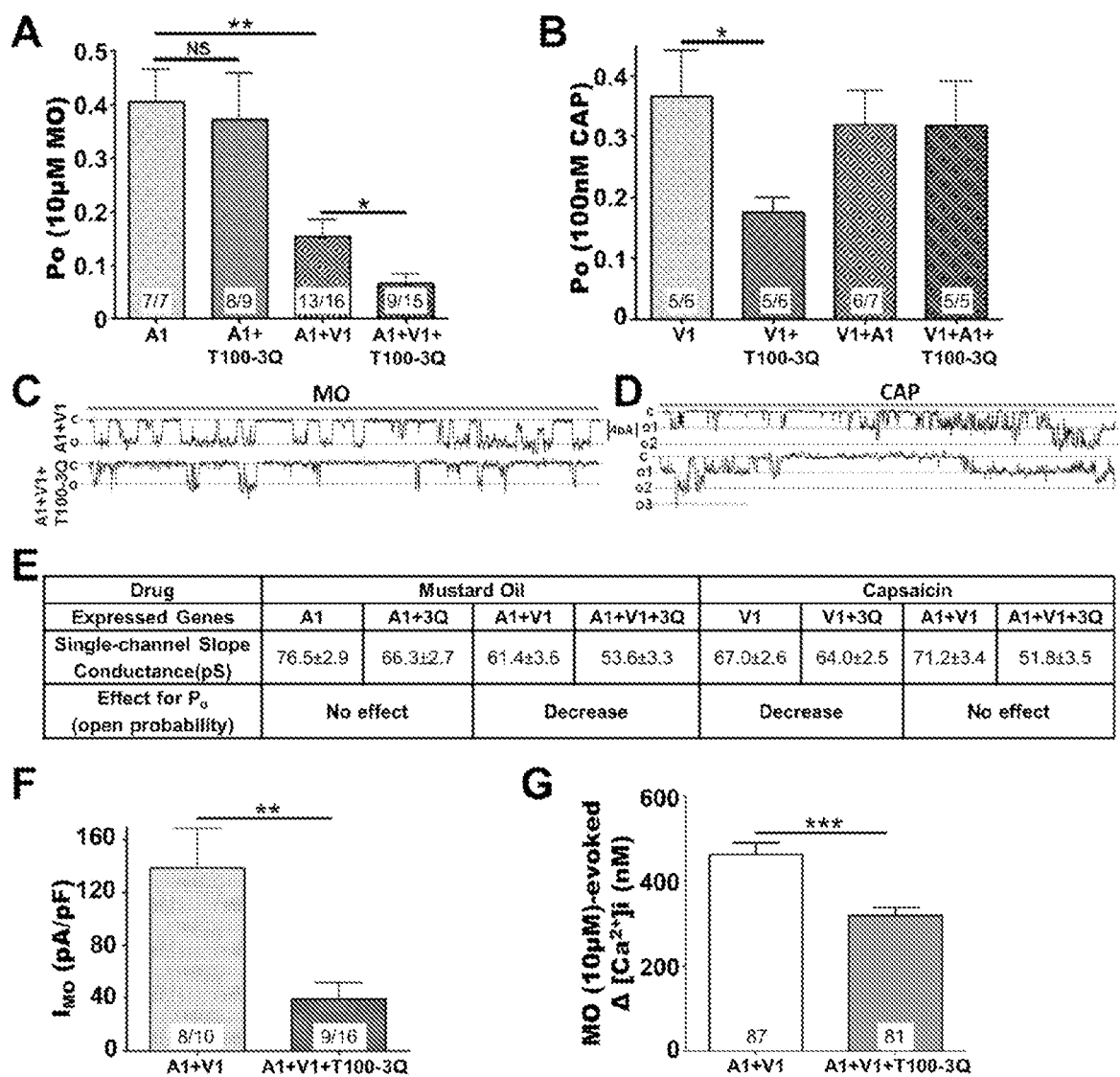
FIG. 6A-FIG. 6G demonstrate context-dependent regulation of Tmem100-3Q mutant in the TRPA1-V1 complex.

Example 9: Tmem100-3Q Selectively Inhibits TRPA1-Mediated Single Channel Activity in the TRPA1-V1 Complex Further functional investigation of Tmem100-3Q revealed that mutant Tmem100 has the opposite effect of wild-type Tmem100 on TRPA1-mediated single-channel properties at −60 mV (FIGS. 6A-E and 14A-D). It was found that in TRPA1-V1 co-expressing cells, Tmem100-3Q significantly decreased single-channel MO-evoked Po with modest alterations in unitary conductance (FIGS. 6A,E, and 14). Similarly, whole-cell MO-activated current density was significantly lower in TRPA1-V1 co-expressing cells containing Tmem100-3Q than control cells without Tmem100-3Q (FIG. 6F). Similar results were obtained by calcium imaging assay (FIG. 6G). Tmem100-3Q also lowered the percentage of cells that responded to MO and CA in HEK293T cells expressing both TRPA1 and TRPV1 (FIGS. 11L,M). Unlike MO responses in TRPA1-V1 cells, TRPV1-mediated single-channel activity induced by CAP in TRPA1-V1 cells was relatively unchanged in the presence of Tmem100-3Q (FIGS. 6B,D,E).

Figure 14:
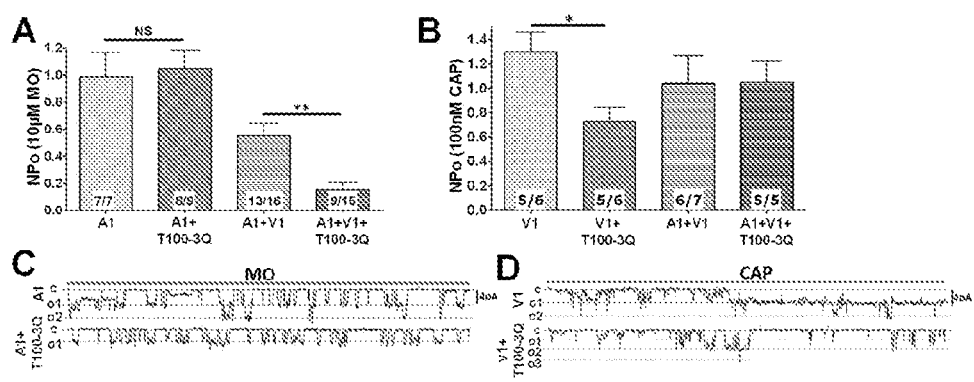
FIGS. 14 C and D show representative single-channel recording traces at Vh=−60 mV for MO-gated current in TRPA1 and TRPA1+Tmem100-3Q-expressing CHO cells (FIG. 14C) and CAP-gated current in TRPV1 and TRPV1+Tmem100-3Q-expressing CHO cells (FIG. 14D). Traces are 4 sec long, and protein expression is indicated below the traces. Vertical bars on the right side of the traces represent 4 pA; c is the closed state; o1, o2, and o3 show open states for 3 independent channels in the patch.

Like wild-type Tmem100, Tmem100-3Q also exerts context-dependent modulatory effects on TRPA1 and TRPV1 homomers. Tmem100-3Q reduced single-channel responses of cells expressing TRPV1 alone whereas it had no effect on TRPA1 responses in cells containing only TRPA1 (FIG. 6A,B). CAP responses from TRPV1-expressing CHO cells showed that the addition of Tmem100-3Q lowered its Po as well as NPo (FIGS. 6B, 14B,D). In contrast, no modulatory effect of Tmem100-3Q on TRPA1-mediated single-channel open probability (Po) or activity (NPo) was observed in TRPA1-expressing cells (FIGS. 6A, 14A,C). In summary, these data suggest that Tmem100-3Q affects intrinsic and whole-cell TRPA1 activity only in the presence of TRPV1.

Example 10: Cell-Permeable Peptides Mimicking Tmem100-3Q Attenuate TRPA1 Activity and Block Pain To selectively attenuate TRPA1-mediated activity in both cellular and behavioral studies, a cell-permeable peptide was utilized, an approach that has been employed to effectively modulate intracellular protein activity (Koren and Torchilin, 2012). A T100-Mut, a peptide that shares sequence with the C-terminus of Tmem100-3Q (FIG. 7A) was designed and synthesized. In addition, the N-terminus of this peptide was conjugated with a myristoylated group, which allows peptides to penetrate and localize to the intracellular side of the plasma membrane (Nelson et al., 2007), thereby mimicking the topology of Tmem100-3Q (FIG. 8D).

Figure 7:
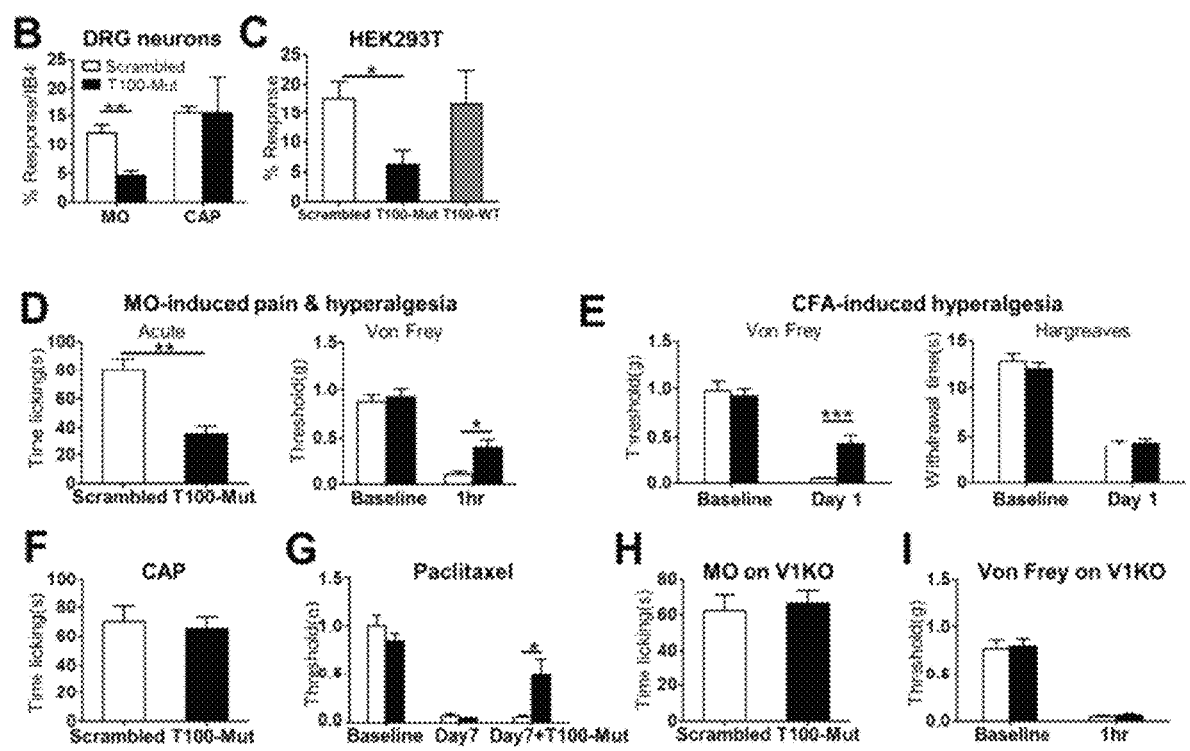
FIG. 7A-FIG. 7I demonstrate that T100-Mut cell-permeable peptide (T100-Mut) alleviates TRPA1-associated pain.

At the cellular level, T100-Mut mimicked the effect of full-length Tmem100-3Q by lowering TRPA1-mediated activity in the TRPA1-V1 complex. T100-Mut pretreatment selectively decreased responses to 10 µM MO in IB4-negative DRG neurons (FIG. 7B). However, the peptide had no effect on responses to 100 nM CAP in the same population (FIG. 7B). The results were largely consistent in a heterologous system. T100-Mut treatment produced a 65% reduction in the percentage of cells responding to MO (FIG. 7C). These results suggest that T100-Mut mainly reduced TRPA1- but not TRPV1-associated activity. A CPP that shares sequence with the wild-type C terminus (T100-WT) was also tested. The result shows that T100-WT does not have a modulatory effect on TRPA1-V1 complexes (FIG. 7C).

Figure 15:
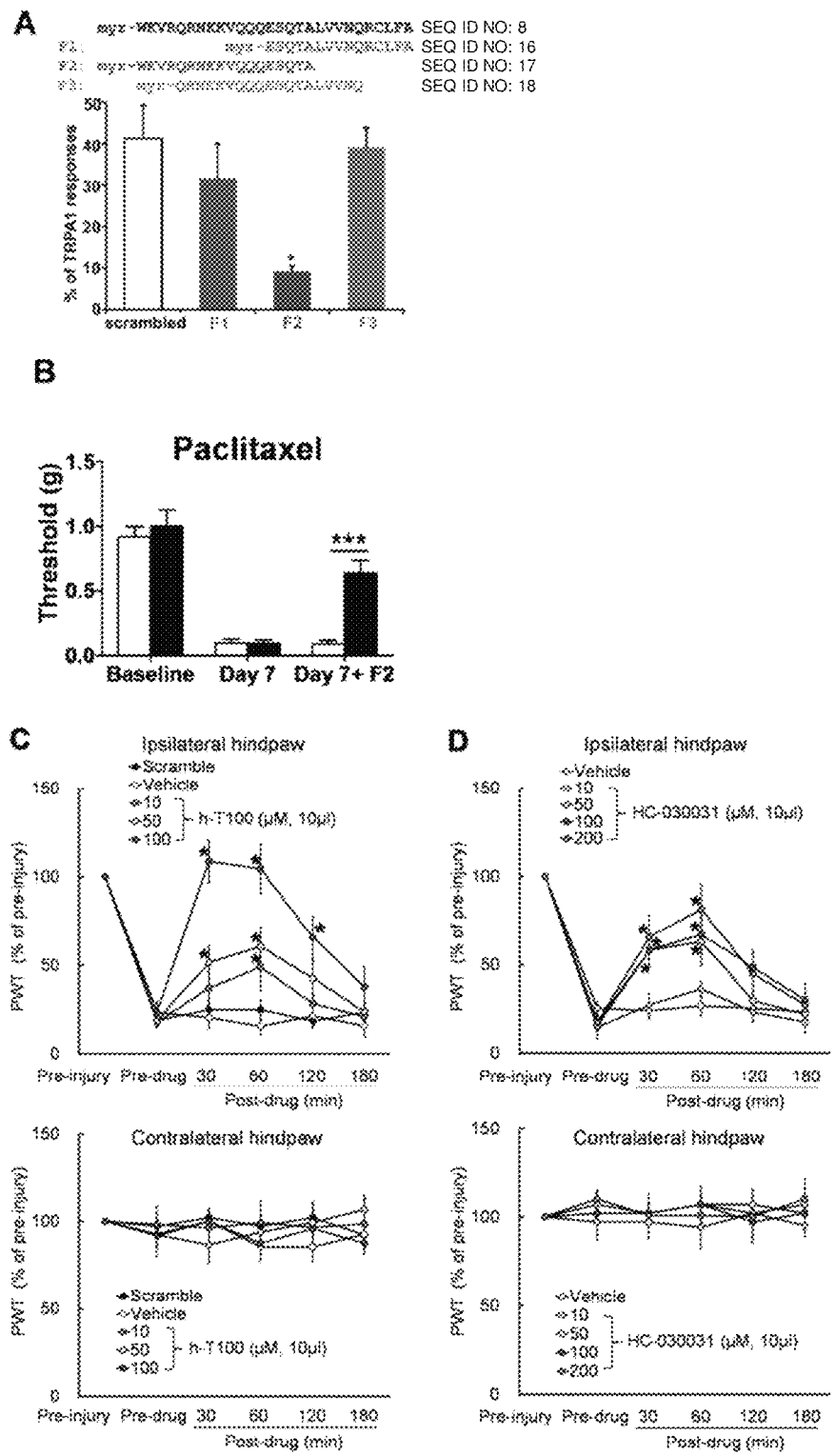
FIG. 15A-FIG. 15D are related to FIG. 7A-7I and demonstrate a shortened version of cell-permeable peptide (CPP) derived from T100-Mut, F2, is also effective for inhibiting TRPA1 activities in the heterologous system and painful behavioral models.

Next, it was tested whether T100-Mut has a corresponding inhibitory effect on pain behaviors. T100-Mut-injected wild-type animals showed reduced MO-induced pain behavior (FIG. 7D). T100-Mut treatment significantly decreased acute nocifensive behavior (36±6 s) compared to the scrambled peptide-treated group (80±9 s). Mechanical hyperalgesia was also significantly attenuated by T100-Mut (FIG. 7D). However, T100-Mut did not alter acute nocifensive behavior induced by CAP (FIG. 7F). Similar results were obtained in the CFA model: 3 hours after T100-Mut treatment, mice showed attenuated mechanical but not thermal hyperalgesia (FIG. 7E). The mechanical thresholds were significantly higher in the T100-Mut-treated group. The level of thermal hyperalgesia remained similar between these two groups. T100-Mut also alleviated mechanical hyperalgesia induced by paclitaxel (Taxol), a commonly used chemotherapeutic agent that produces TRPA1-dependent neuropathy as a side effect (Materazzi et al., 2012) (FIG. 7G). Furthermore, a shortened CPP (called F2) consisting of the first 18 amino acids of the T100-Mut could produce the same inhibitory effects whereas two other shortened CPPs that spanned different regions of the T100-Mut C-terminus had no effect (FIG. 15A,B). Together, these data suggest that the first 4 amino acids of the Tmem100 C-terminus, i.e. "WKVR", and the 3Q mutations are essential for the inhibitory effect of TMEM100-3Q on TRPA1 in the TRPA1/V1 complex and that this effect is likely caused by an enhanced interaction of TMEM100-3Q with TRPV1. Furthermore, there was no effect of T100-Mut on MO-induced acute pain and mechanical hyperalgesia in Trpv1$^{-/-}$ mice (FIGS. 7H,I). The effects of T100-Mut and HC-030031, a direct TRPA1 antagonist (Eid et al., 2008), were also compared and it was found that T100-Mut showed comparable or better efficacy and potency of inhibiting neuropathic pain as the TRPA1 antagonist (FIG. 15C,D). These behavioral data demonstrate that T100-Mut selectively alleviates TRPA1-associated pain and that this effect is TRPV1-dependent.

Example 11: Tmem100 Mutant Peptide Blocks Ongoing Pain

Ongoing, or spontaneous, pain, which is most bothersome to patients, is difficult to treat and difficult to study in animals. The conditioned place preference test has been successfully developed to reveal the presence of non-evoked, ongoing pain and pain relief based on the preference of an animal for the context paired with a pain-relief treatment. The conditioned place preference can also capture the aversive aspects of pain. Strikingly, many studies have shown that the rodent conditioned place preference test accurately reflects the effectiveness of human clinical treatments. Therefore, this test is a powerful approach to investigate the potential effectiveness of new treatments and mechanisms for relief of ongoing pain. Two previous studies have examined the role of TRPA1 in ongoing pain by the conditioned place preference test. However, in both studies, inhibition of TRPA1 by antagonists strongly blocked evoked mechanical hyperalgesia but did not block ongoing pain induced by chronic pain models. These results highlight differential mechanisms of evoked and ongoing pain. Because the antagonists used in those studies (HC030031 and Chem5861528) target TRPA1 monomers, it is possible that T100-Mut can inhibit ongoing pain by modulating the TRPA1/V1 complex. This possibility was tested in rodents with SNL-induced ongoing pain using the conditioned place preference test. Data showed that one 10-µl dose of 50 µM human T100-Mut peptide (also called P2-Mut) intrathecally injected into SNL rats induced robust the conditioned place preference, suggesting that T100-Mut indeed blocked ongoing pain; the scrambled peptide had no effect (FIG. 16A). Systemic administration of gabapentin, an analgesic that is known to alleviate neuropathic pain, was used as a positive control (FIG. 16B).

Example 12. Tmem100 and Itch in Conditional Knockout Mouse Model

Figure 16:
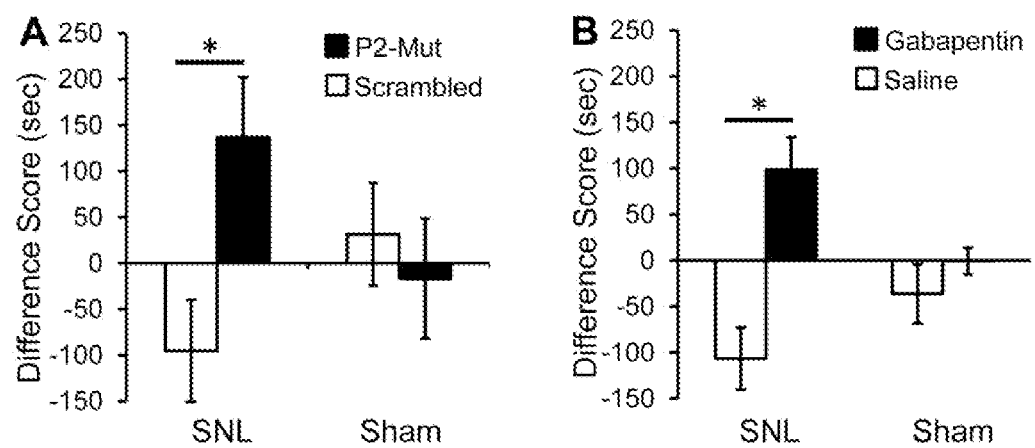
FIG. 16A-FIG. 16B demonstrate that P2-Mut (T100-Mut; SEQ ID NO: 7) inhibits ongoing pain.

The current evidence suggest that Tmem100 plays a role in itch. There are itch phenotypes in Tmem100 conditional knockout mice: they have deficits for the scratching responses by histamine injection on the back (FIG. 16). A wide array of pruritogens will be tested in calcium imaging on Tmem100-deficient DRG neurons and by behavioral assays on Tmem100 conditional knockout mice to interrogate the extent of itch phenotype.

Figure 17:
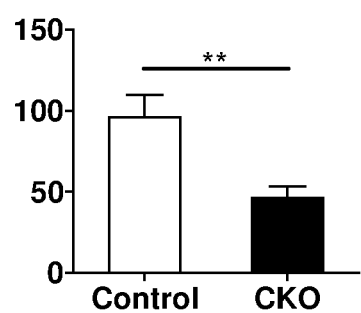
FIG. 17 is a graph that shows deceased itch behavior in Pirt2-CKO (Tmem100-CKO) mice. The Y axis represents the numbers of scratches in the first 30 minutes after histamine back injection. The Pirt2-CKO (Tmem100 CKO) mice showed robust decreased itch behavior. (n=10 and 11 for control and CKO).
Figure 18:
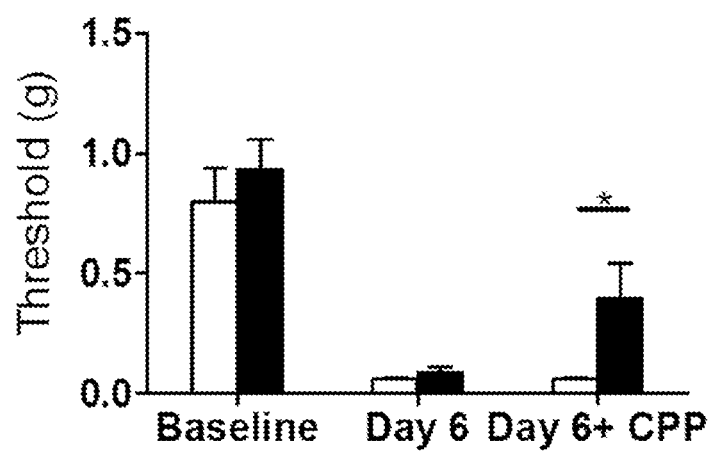
FIG. 18 is a graph that shows in the wild-type mice with spinal nerve ligation (SNL), mechanical hyperalgesia is observed 6 days post ligation. Intradermal injection of Tmem 100 peptide (CPP) SEQ ID NO: 17 blocked SNL-induced mechanical hyperalgesia.

Example 13. Human Tmem100-30 CPP Alleviates Neuropathic Pain by Nerve Injury In the wild-type mice with spinal nerve ligation (SNL), mechanical hyperalgesia is observed 6 days post ligation. Palmitoylated (Pal) CPP tailored to the C-terminus of human Tmem100-3Q alleviates neuropathic pain/mechanical allodynia in SNL. n=6, *p<0.05 at Day 6 4 hrs post CPP treatment. Scrambled: open bar; human P2-Mut (T100-Mut): black bar (FIG. 17). Peptides (5 µl of 2 mM) were injected intradermally in the hindpaws. Sequences for CPP used in the SNL experiment:
Human P2-Mut (T100-Mut) Pal-WKVRQRSK-KAQQQESQTALVANQRSLFA-OH (SEQ ID NO: 7); Scrambled Pal-QRALEQVLQNWSR-RANVKQAQKFQVKST-OH (SEQ ID NO: 19). Pal-palmitoylated in the N termini for each CPP.

Example 14: Functional Interaction Between TRPV1 and TRPA1

Functional interaction between TRPV1 and TRPA1 can occur in several ways (Julius, 2013) and TRPV1 and TRPA1 can modulate each other's activity by activating intracellular pathways. For example, activation of TRPA1 can cause $Ca^{2+}$ influx, triggering $Ca^{2+}$-dependent phosphatases, which in turn, desensitize TRPV1 activity (Akopian et al., 2007). Alternatively, TRPA1-initiated $Ca^{2+}$ influx could promote protein kinase A activity, sensitizing TRPV1 channels (Spahn et al., 2014). Behavioral experiments demonstrated that TRPA1 activation by MO leads to functional desensitization of TRPV1 responses in vivo (Jacquot et al., 2005; Ruparel et al., 2008). Similarly, activation of TRPV1 can lead to reduction of TRPA1 activity in vitro and in vivo (Akopian et al., 2007; Jacquot et al., 2005; Ruparel et al., 2008). An important element of these functional TRPV1-TRPA1 interactions is that the channels need to be activated sequentially.

As described herein, an alternative mechanism could be the interaction of TRPV1 and TRPA1 within a complex. Indeed, evidence indicates that TRP channels are capable of assembling into channel complexes (Schaefer, 2005; Strubing et al., 2003). Physical interaction within TRP complexes alter the conformation of channels and thus influence the biophysical and regulatory properties of each TRP channel (Xu et al., 1997). It was demonstrated that TRPV1 and TRPA1 can form a complex in heterologous expression systems and sensory neurons (Akopian et al., 2007; Fischer et al., 2014; Staruschenko et al., 2010). Formation of such a complex can strongly influence the properties of TRPA1 (Patil et al., 2011; Salas et al., 2009). Thus, as described herein, the composition and function of TRPV1-TRPA1 complexes in sensory neurons is elucidated, as well as the requirement of TRPV1 activity for regulation within the complex.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating or preventing a condition associated with TRPA1 function or for which reduced TRPA1 activity can reduce the severity, comprising administering an effective amount of a Tmem100 mutant polypeptide, comprising administering to the cell an effective amount of a Tmem100 mutant polypeptide, wherein the Tmem100 mutant polypeptide comprises an amino acid sequence selected from the group consisting of: SEQ ID NO: 5, SEQ ID NO: 6, SEQ ID NO: 7, SEQ ID NO: 8, and SEQ ID NO: 17, thereby inhibiting TRPA1 function in the cell; or
  a method of preventing, treating, or alleviating symptoms of a disease or condition associated with TRPA1 function or for which reduced TRPA1 activity can reduce the severity, comprising administering to a subject in need thereof a Tmem100 mutant polypeptide, wherein the Tmem100 mutant polypeptide comprises an amino acid sequence selected from the group consisting of: SEQ ID NO: 5, SEQ ID NO: 6, SEQ ID NO: 7, SEQ ID NO: 8, and SEQ ID NO: 17, thereby inhibiting TRPA1 function in the cell; or
  a method of inhibiting TRPA1 function in a cell, comprising administering to the cell an effective amount of a Tmem100 mutant polypeptide, wherein the Tmem100 mutant polypeptide comprises an amino acid sequence selected from the group consisting of: SEQ ID NO: 5, SEQ ID NO: 6, SEQ ID NO: 7, SEQ ID NO: 8, and SEQ ID NO: 17, thereby inhibiting TRPA1 function in the cell.

2. The method of claim 1 wherein the TRPA1 function is an association with TRPV1.

3. The method of claim 2, wherein the Tmem100 mutant polypeptide enhances the association of TRPA1 with TRPV1.

4. The method of claim 1, wherein said TRPA1 function is an inward TRPA1-mediated current, an outward TRPA1-mediated current, TRPA1-mediated ion flux or TRPA1-mediated neuronal hyperexcitability.

5. The method of claim 1, wherein the Tmem100 mutant polypeptide comprises a polypeptide with one or more alterations in the amino acid sequence of SEQ ID NO: 1 or SEQ ID NO: 2 wherein the one or more alterations in the amino acid sequences enhance association of TRPA1 and TRPV1 and inhibit TRPA 1.

6. The method of claim 1, wherein the Tmem100 mutant polypeptide is provided to a cell and the cell is a sensory neuron.

7. The method of claim 6, wherein the cell body of the sensory neuron resides in the dorsal root ganglia (DRG).

8. The method of claim 1, used to prevent, treat, or alleviate symptoms of pain.

9. The method of claim 1, used to prevent, treat, or alleviate symptoms of itch.

10. The method of claim 8, wherein the pain is acute pain or chronic pain.

11. The method of claim 1, wherein the Tmem100 mutant polypeptide is administered in combination with one or more agents.

12. The method of claim 1, wherein the Tmem100 mutant polypeptide is administered in combination with one or more of a TRPV1 inhibitor, a TRPV3 inhibitor, a TRPV4 inhibitor, or a TRPM8 inhibitor.

13. A pharmaceutical composition for treating or preventing a condition involving activation of TRPA1 or for which reduced TRPA1 activity can reduce the severity, comprising an effective amount of a Tmem100 mutant polypeptide, wherein the Tmem100 mutant polypeptide comprises an amino acid sequence selected from the group consisting of: SEQ ID NO: 5, SEQ ID NO: 6, SEQ ID NO: 7 and SEQ ID NO: 8.

14. The pharmaceutical composition of claim 13, wherein the Tmem100 mutant polypeptide comprises a polypeptide with one or more alterations in the amino acid sequence of SEQ ID NO: 1 or SEQ ID NO: 2 wherein the one or more alterations in the amino acid sequences enhance association of TRPA1 and TRPV1 and inhibit TRPA1.

15. An isolated cell-permeable polypeptide comprising an amino acid sequence selected from the group consisting of: SEQ ID NO: 5, SEQ ID NO: 6, SEQ ID NO: 7 and SEQ ID NO: 8, wherein the polypeptide is myristoylated or palmitoylated at each N-terminus.

16. An expression vector, which replicates in at least one of a prokaryotic cell and eukaryotic cell, comprising:
  an isolated nucleic acid comprising a nucleotide sequence selected from the group consisting of: SEQ ID NO: 9, SEQ ID NO: 10, SEQ ID NO: 11 and SEQ ID NO: 12; or
  expresses a polypeptide comprising an amino acid sequence selected from the group consisting of: SEQ ID NO: 5, SEQ ID NO: 6, SEQ ID NO: 7 and SEQ ID NO: 8.

17. A cell comprising an expression vector which replicates in at least one of a prokaryotic cell and eukaryotic cell, comprising:

an isolated nucleic acid comprising a nucleotide sequence selected from the group consisting of: SEQ ID NO: 9, SEQ ID NO: 10, SEQ ID NO: 11 and SEQ ID NO: 12; or wherein the expression vector expresses a polypeptide comprising an amino acid sequence selected from the group consisting of: SEQ ID NO: 5, SEQ ID NO: 6, SEQ ID NO: 7 and SEQ ID NO: 8.

18. A method comprising culturing a cell in a cell culture medium, the cell comprising an expression vector which replicates in at least one of a prokaryotic cell and eukaryotic cell, wherein the expression vector comprises: an isolated nucleic acid comprising a nucleotide sequence selected from the group consisting of: SEQ ID NO: 9, SEQ ID NO: 10, SEQ ID NO: 11 and SEQ ID NO: 12; or comprises a nucleotide sequence encoding a polypeptide comprising an amino acid sequence selected from the group consisting of: SEQ ID NO: 5, SEQ ID NO: 6, SEQ ID NO: 7 and SEQ ID NO: 8.

* * * * *